United States Patent
Bourrain et al.

(10) Patent No.: US 7,101,892 B2
(45) Date of Patent: Sep. 5, 2006

(54) SULFONE DERIVATIVES AS 5-HT7 RECEPTOR LIGANDS

(75) Inventors: Sylvie Bourrain, High Easter (GB); Peter Alan Hunt, Saffron Walden (GB); Ian Thomas Huscroft, Bishops Stortford (GB); Janusz Jozef Kulagowski, Sawbridgeworth (GB); Clare London, Sawbridgeworth (GB); Elizabeth Mary Naylor, Saffron Walden (GB); Piotr Antoni Raubo, Bishops Stortford (GB); Eileen Mary Seward, Bishops Stortford (GB)

(73) Assignee: Merck Sharp & Dohme Ltd., Hoddesdon ( * ) Notice: Subject to any disclaimer, the term of this patent is extended or adjusted under 35 U.S.C. 154(b) by 31 days.

(21) Appl. No.: 10/845,847

(22) Filed: May 14, 2004

(65) Prior Publication Data

US 2004/0229864 A1    Nov. 18, 2004

(30) Foreign Application Priority Data

May 15, 2003  (GB)  ................................ 0311201.8

(51) Int. Cl.
*A61K 31/44* (2006.01)

(52) U.S. Cl. ........................ 514/299; 546/112
(58) Field of Classification Search ........ 546/112; 514/299
See application file for complete search history.

(56) References Cited

U.S. PATENT DOCUMENTS 6,559,171 B1 * 5/2003 Mitch et al. ............... 514/362

6,635,645 B1 * 10/2003 Lochead et al. ......... 514/252.01

FOREIGN PATENT DOCUMENTS

| WO | WO 97/29097 | 8/1997 |
|---|---|---|
| WO | WO 97/48681 | 12/1997 |
| WO | WO 97/49695 | 12/1997 |
| WO | WO 99/24022 | 5/1999 |
| WO | WO 99/31062 | 6/1999 |
| WO | WO 00/00472 | 1/2000 |
| WO | WO 00/56712 | 9/2000 |
| WO | WO 00/73299 | 12/2000 |

OTHER PUBLICATIONS

Thomas, DR et al 'SB-656104-A, a novel selective 5-HT7 receptor antagonist, modulates REM sleep in rats' British Journal of Pharmacology (2003) 139, 705-714.*
Stam, NJ et al 'Human serotonin 5-HT7 receptor: cloning and pharmacological characterisation of two receptor variants' FEBS Letters 143 (1997), 489-494.*
Wolff, MC et al 'The discriminative stimulus properties of LY233708, a selective serotonin reuptake inhibitior, in the pigeon' Psychopharmacology (1999) 146:275-279.*

* cited by examiner

*Primary Examiner*—Amelia A. Owens
(74) *Attorney, Agent, or Firm*—J. Eric Thies; Melvin Winokur

(57) ABSTRACT

The present invention relates to sulfone derivatives of formula (I):

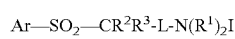

Ar—SO$_2$—CR$^2$R$^3$-L-N(R$^1$)$_2$I wherein Ar, L, R$^1$, R$^2$ and R$^3$ are as defined herein, and pharmaceutically acceptable salts and N-oxides thereof, useful in the treatment of a condition which is susceptible to treatment by modulation of 5-HT$_7$ receptor activity, such as depression or a sleep disorder.

11 Claims, No Drawings

SULFONE DERIVATIVES AS 5-HT7 RECEPTOR LIGANDS

CROSS REFERENCE TO RELATED APPLICATIONS

This application claims priority under 35 U.S.C. § 119 from GB Application No. 0311201.8, filed May 15, 2003.

The present invention lies in the field of therapeutic treatments of the human body, and in particular relates to a class of sulphone derivatives which act on serotonin receptors (also known as 5-hydroxytryptamine or 5-HT receptors). More particularly, the invention concerns aryl- and heteroarylsulphones wherein the sulphone group is linked to a cyclic amino functionality. These compounds are selective ligands for the human $5\text{-HT}_7$ receptor and are therefore useful as pharmaceutical agents, especially in the treatment and/or prevention of adverse conditions of the central nervous system, such as depression, anxiety, sleep disorders and psychotic disorders such as schizophrenia.

The compounds according to the present invention are potent and selective $5\text{-HT}_7$ receptor ligands having a human $5\text{-HT}_7$ receptor binding affinity ($K_i$) of 500 nM or less, typically of 100 nM or less, and in preferred examples, of 50 nM or less. The compounds of the invention may possess at least a 10-fold selective affinity, suitably at least a 20-fold selective affinity and preferably at least a 50-fold selective affinity, for the human $5\text{-HT}_7$ receptor relative to the other human 5-HT receptors (in particular the $5\text{-HT}_{1A}$, $5\text{-HT}_{1B}$ and $5\text{-HT}_{2A}$ receptors) and to the human dopamine $D_2$ receptor. By virtue of this selectivity, it is possible to provide treatments for the above-mentioned disorders having fewer or different side effects in comparison to known treatments for these disorders.

WO97/29097, WO97/48681, WO97/49695, WO00/00472, WO99/24022, WO99/31062, WO00/56712 and WO00/73299 disclose various classes of compounds to be $5\text{-HT}_7$ receptor ligands, but do not disclose or suggest compounds in accordance with the present invention.

According to the invention there is provided a compound of formula I or a pharmaceutically acceptable salt or N-oxide thereof:

$$\text{Ar}-\text{SO}_2-\text{CR}^2\text{R}^3-\text{L}-\text{N}(\text{R}^1)_2 \qquad \text{I}$$

wherein the $R^1$ groups complete a heterocyclic ring system comprising up to 3 fused rings, each containing up to 7 ring atoms, said system optionally bearing up to 3 substituents selected from halogen, CN, $NO_2$, $CF_3$, $R^4$, $OR^5$, $SR^5$, $N(R^6)R^5$, $CO_2R^5$, $OCOR^4$, $COR^5$, $CON(R^6)R^5$, $N(R^6)COR^4$, $N(R^6)SO_2R^4$, $CON(R^6)OR^6$, $C(R^5)=NOR^6$ and =X;

X represents $N-OR^6$, or $CR^7R^8$;

$R^4$ represents phenyl, naphthyl or heterocyclyl, any of which optionally bears up to 3 substituents selected from halogen, CN, $NO_2$, $CF_3$, OH, $OCF_3$, $C_{1-6}$alkyl, $C_{1-6}$alkoxy, $C_{1-6}$alkoxycarbonyl, $C_{2-6}$acyl and $C_{2-6}$acyloxy; or $R^4$ represents a nonaromatic hydrocarbon group of up to 10 carbon atoms optionally substituted with up to 3 halogen atoms or with one substituent selected from CN, $NO_2$, $CF_3$, $OCF_3$, $C_{1-6}$alkoxy, $C_{1-6}$alkoxycarbonyl, $C_{2-6}$acyl, $C_{2-6}$acyloxy, $N(R^9)_2$ and phenyl, phenoxy, phenylthio, naphthyl or heterocyclyl, any of which optionally bears up to 3 substituents selected from halogen, CN, $NO_2$, $CF_3$, OH, $OCF_3$, $C_{1-6}$alkyl, $C_{1-6}$alkoxy, $C_{1-6}$alkoxycarbonyl, $C_{2-6}$acyl and $C_{2-6}$acyloxy;

$R^5$ represents H or $R^4$;

$R^6$ represents H or $C_{1-6}$alkyl;

or $R^5$ and $R^6$ bonded to the same nitrogen atom may complete a ring of up to 7 members selected from C, N, O and S;

$R^7$ and $R^8$ independently represent H or a hydrocarbon group of up to 10 carbon atoms, or together complete a hydrocarbon ring of up to 14 members;

$R^2$ and $R^3$ independently represent H, hydrocarbon of up to 6 carbon atoms, $C_{2-6}$acyl, $C_{1-6}$alkoxycarbonyl or hydroxy$C_{1-6}$alkyl, or together complete a hydrocarbon ring of up to 6 carbon atoms;

L is a linking group selected from:

(a) $-CR^{2a}R^{3a}-(CH_2)_n-$;
(b) $-O-CH_2CH_2-$;
(c) $-CH_2CH(OH)CH_2-$;
(d) $-CH=CH-CH_2-$; and
(e) $-C\equiv C-CH_2-$;

$R^{2a}$ and $R^{3a}$ have the same definition as $R^2$ and $R^3$;

n is 1, 2 or 3;

Ar represents phenyl, naphthyl or heteroaryl, any of which optionally bears up to 3 substituents selected from halogen, CN, $NO_2$, $CF_3$, $OCF_3$, $R^9$, $OR^9$, $CO_2R^9$ and $COR^9$; and $R^9$ represents H or a hydrocarbon group of up to 7 carbon atoms.

Where a variable occurs more than once in formula I or in a substituent thereof, the individual occurrences of that variable are independent of each other, unless otherwise specified.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

As used herein, the expression "$C_{2-6}$acyl" refers to keto groups comprising from 2 to 6 carbon atoms in total. Examples include acetyl, propanoyl, butanoyl, propenoyl and cyclopentanoyl.

Unless otherwise specified, the term "heterocyclyl" as used herein refers to monocyclic ring systems of up to 7 skeletal atoms or bicyclic ring systems of up to 10 skeletal atoms wherein at least one of the skeletal atoms is N, O or S, the remainder being carbon. Preferably not more than four, and most preferably not more than three, skeletal atoms are other than carbon. Each constituent ring may be fully saturated, partially unsaturated or fully unsaturated, including aromatic. Bicyclic ring systems may be spiro-linked, ortho-fused or bridged. Heterocyclyl groups may be attached via a ring carbon or a ring nitrogen, if present.

As used herein, the expression "heteroaryl" refers to heterocyclyl groups in which the constituent rings are aromatic. The expression thus includes 5-membered monocyclic systems such as pyrrole, furan, thiophene, pyrazole, imidazole, triazole, tetrazole, oxazole, isoxazole, thiazole, isothiazole, oxadiazole and thiadiazole, 6-membered monocyclic systems such as pyridine, pyridazine, pyrimidine, pyrazine and triazine, as well as benzo-fused derivatives thereof (where such derivatives are possible) such as quinoline, isoquinoline, indole, benzofuran and benzothiazole.

The term "halogen" as used herein includes fluorine, chlorine, bromine and iodine, of which fluorine and chlorine are preferred.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In formula I, the $R^1$ groups complete a heterocyclic ring system comprising up to 3 fused rings, each containing up to 7 ring atoms, which is optionally substituted as defined previously. Preferably, not more than one ring contains more than 6 ring atoms. In addition to the nitrogen atom in formula I to which the $R^1$ groups are attached, the ring system completed by the $R^1$ groups preferably contains at most one ring atom that is other than carbon, selected from N, O and S, of which N and O (especially N) are preferred.

Monocyclic ring systems completed by the $R^1$ groups typically comprise 5, 6 or 7 ring atoms. Examples include pyrrolidine, piperidine, tetrahydropyridine, piperazine, morpholine, thiomorpholine and homopiperidine.

In bicyclic or tricyclic ring systems completed by the $R^1$ groups, the additional ring(s) may be spiro-linked or ortho-fused or may form a bridged system, but ortho-fused and bridged systems are preferred. Additional ortho-fused rings may be fully saturated, partially-unsaturated or aromatic. Examples of suitable bicyclic and tricyclic systems include tetrahydroquinoline, tetrahydroisoquinoline, octahydroisoquinoline, decahydroquinoline, decahydroisoquinoline, isoindoline, 2,3,3a,4,5,9b-hexahydro-1H-benzo[e]isoindole, tetrahydrocarboline, 2-azabicyclo[2,2,1]heptane and 7-azabicyclo[2,2,1]heptane.

The ring system completed by the $R^1$ groups may bear up to 3 substituents selected from halogen, CN, $NO_2$, $CF_3$, $R^4$, $OR^5$, $SR^5$, $N(R^6)R^5$, $CO_2R^5$, $OCOR^5$, $COR^5$, $CON(R^6)R^5$, $N(R^6)COR^5$, $N(R^6)SO_2R^5$, $CON(R^6)OR^6$, $C(R^5)$=$NOR^6$ and =X, where $R^4$, $R^5$, $R^6$ and X are as defined previously. Typically, if more than one substituent is present, not more than one of said substituents is other than halogen, $C_{1-4}$alkyl or $C_{1-4}$alkoxy.

Preferred substituents include CN, $CF_3$, $R^4$, $OR^5$, $SR^5$, $N(R^6)R^5$, $CO_2R^4$, $COR^4$, $CON(R^6)R^5$, $N(R^6)COR^5$, $N(R^6)SO_2R^5$, $CON(R^6)OR^6$, $C(R^5)$=$NOR^6$ and =X.

In one embodiment, $R^4$ is phenyl, naphthyl or heterocyclyl, any of which may itself bear up to 3 substituents selected from halogen, CN, $NO_2$, $CF_3$, OH, $OCF_3$, $C_{1-6}$alkyl, $C_{1-6}$alkoxy, $C_{1-6}$alkoxycarbonyl, $C_{2-6}$acyl and $C_{2-6}$acyloxy, but preferably not more than one such substituent is other than halogen or alkyl. Heterocyclyl groups represented by $R^4$ are typically heteroaromatic, for example pyridine, quinoline, furan, thiophene, oxazole, imidazole, benzimidazole, benzisoxazole, indole, tetrazole or quinazoline. Examples of groups represented by $R^4$ within this embodiment include 2-naphthyl; phenyl which is optionally substituted with up to 2 fluorine atoms or chlorine atoms, or with OH, Me, OMe, t-butoxy, CN, $NO_2$ or $CF_3$; 2-, 3- or 4-pyridyl which is optionally substituted with up to 2 fluorine atoms or chlorine atoms, or with Me, OMe, CN, or $CF_3$; 2-furyl; 3-furyl; 2-thienyl; 3-thienyl; 3-methylisoxazol-5-yl; 5-methylisoxazol-3-yl; 3,5-dimethylisoxazol-4-yl; oxazol-5-yl; 4-methyloxazol-2-yl; indol-3-yl; 2-methyltetrazol-5-yl; imidazol-2-yl; benzimidazol-2-yl; benzisothiazol-3-yl; 2-quinolinyl; and 2-quinoxalinyl.

Alternatively, $R^4$ represents a nonaromatic hydrocarbon group of up to 10 carbon atoms, optionally substituted as defined previously. Suitable hydrocarbon groups include linear and branched alkyl groups (such as methyl, ethyl, n-propyl, isopropyl, n-butyl and t-butyl), cycloalkyl groups (such as cyclopentyl and cyclohexyl), cycloalkylalkyl groups (such as cyclohexylethyl), alkenyl groups (such as vinyl, allyl and 2-propenyl), and alkynyl groups (such as ethynyl, propynyl and propargyl). Hydrocarbon groups represented by $R^4$ are preferably unsubstituted or substituted with halogen, OH, CN, alkoxy, acyl, alkoxycarbonyl, $N(R^9)_2$, phenyl or heteroaryl (such as pyridyl), the phenyl or heteroaryl substituent being itself optionally substituted as defined previously, but preferably being unsubstituted or substituted with methyl, methoxy, F, Cl or $CF_3$. Examples of $N(R^9)_2$ substituents include N(Me)Ph and $N(Me)CH_2Ph$.

$R^5$ represents H or has the definition as $R^4$; or $R^5$ may combine with $R^6$ to complete a ring when $R^5$ and $R^6$ are attached to the same nitrogen atom. Typically, $R^5$ represents H, optionally-substituted $C_{1-6}$alkyl, optionally-substituted phenyl or heteroaryl, or completes a ring with $R^6$. When $R^5$ represents $C_{1-6}$alkyl, said alkyl group is preferably unsubstituted (e.g. methyl, ethyl, n-propyl, isopropyl, n-butyl, and t-butyl) or is substituted with phenyl which is itself unsubstituted or substituted with methyl, methoxy, F, Cl or $CF_3$ (e.g. benzyl and phenylethyl). When $R^5$ represents phenyl or heteroaryl (such as pyridyl), said phenyl or heteroaryl is preferably unsubstituted or substituted with methyl, methoxy, F, Cl or $CF_3$. When $R^5$ completes a ring with $R^6$, typical examples include pyrrolidine, piperidine, morpholine, piperazine and tetrahydropyridine.

$R^6$ represents H or $C_{1-6}$alkyl (such as methyl, ethyl, n-propyl, isopropyl, n-butyl, and t-butyl), or completes a ring with $R^5$ as described above.

In the context of the substituents $OR^5$, $SR^5$, $N(R^6)R^5$, $COR^5$, and $CON(R^6)R^5$, $R^5$ is preferably other than H. In the context of the substituent $C(R^5)$=$NOR^6$, $R^5$ is preferably H or $C_{1-6}$alkyl, most preferably H.

In the context of the substituents $N(R^6)R^5$, $CON(R^6)R^5$, $CON(R^6)OR^6$ and $C(R^5)$=$NOR^6$, $R^6$ is preferably $C_{1-6}$alkyl.

X represents N—$OR^6$ or $CR^7R^8$ where $R^7$ and $R^8$ independently represent H or hydrocarbon of up to 10 carbons, or together complete a hydrocarbon ring of up to 14 members. In this context, $R^6$ is preferably $C_{1-6}$alkyl. Preferably $R^7$ and $R^8$ represent H or hydrocarbon of up to 7 members (e.g. methyl, ethyl, phenyl or benzyl), or complete a ring. An example of a ring completed by $R^7$ and $R^8$ is fluorene. Particular embodiments of X include N—OMe, CHPh and 9-fluorenylidene.

$R^2$ and $R^3$ independently represent H, hydrocarbon of up to 6 carbon atoms, $C_{2-6}$acyl, $C_{1-6}$alkoxycarbonyl or hydroxy$C_{1-6}$alkyl, or together complete a hydrocarbon ring of up to 6 carbon atoms. When one of $R^2$ and $R^3$ is $C_{2-6}$acyl (such as acetyl), $C_{1-6}$alkoxycarbonyl (such as $CO_2Et$) or hydroxy$C_{1-6}$alkyl (such as $CH_2OH$), the other is preferably H or hydrocarbon, most preferably $C_{1-6}$alkyl such as methyl. Preferred hydrocarbon groups represented by $R^2$ and/or $R^3$ include $C_{1-6}$alkyl groups (especially methyl or ethyl) and $C_{2-6}$alkenyl groups (especially allyl). When $R^2$ and $R^3$ complete a hydrocarbon ring, said ring may be saturated (such as cyclopropane, cyclobutane, cyclopentane and cyclohexane) or unsaturated (such as cyclopentene). Rings of up to 5 carbon atoms are preferred, and cyclopropane and cyclobutane are particularly preferred. In one preferred embodiment, $R^2$ and $R^3$ represent identical $C_{1-6}$alkyl groups (preferably methyl), and in another preferred embodiment $R^2$ and $R^3$ complete a cyclopropane or cyclobutane ring.

L represents a linking group selected from —$CR^{2a}R^{3a}$—$(CH_2)_n$—; —O—$CH_2CH_2$—; —$CH_2CH(OH)CH_2$—; —CH=CH—$CH_2$—; and —C≡C—$CH_2$—; where $R^{2a}$ and $R^{3a}$ have the same definition as $R^2$ and $R^3$, and n is 1, 2 or 3. Preferably, $R^{2a}$ and $R^{3a}$ are independently selected from H and $C_{1-6}$alkyl such as methyl. In one preferred embodiment, $R^{2a}$ and $R^{3a}$ are both H. In another preferred embodiment, n is 2. Examples of linking groups represented by L include —$(CH_2)_2$—; —$(CH_2)_3$—; —$(CH_2)_4$—; CH(Me)—$(CH_2)_2$—; —$C(Me)_2$—$(CH_2)_2$—; —O—$CH_2CH_2$—; —$CH_2CH(OH)CH_2$—; —CH=CH—$CH_2$—; and —C≡C—$CH_2$—; of which —$(CH_2)_3$— is particularly preferred.

When L represents —$(CH_2)_{(n+1)}$—; —O—$CH_2CH_2$—; —$CH_2CH(OH)CH_2$—; —CH=CH—$CH_2$—; or —C≡C—$CH_2$—; preferably at least one $R^2$ and $R^3$ is other than H.

Ar represents phenyl, naphthyl or heteroaryl, any of which optionally bears up to 3 substituents selected from halogen, CN, $NO_2$, $CF_3$, $OCF_3$, $R^9$, $OR^9$, $CO_2R^9$ and $COR^9$; and $R^9$ represents H or a hydrocarbon group of up to 7 carbon atoms. Suitable hydrocarbon groups represented by $R^9$ include $C_{1-4}$alkyl, especially methyl or ethyl, and benzyl. Ar typically represents optionally-substituted phenyl, naphthyl, pyridyl or thiophenyl, of which phenyl and naphthyl are preferred. Preferred substituents include halogen, $CF_3$ and $C_{1-6}$alkyl (especially methyl). If more than one substituent is present, preferably not more than one of the substituents is other than halogen or alkyl. Specific examples of groups represented by Ar include, phenyl, 1-naphthyl, 2-methylphenyl, 3-methylphenyl, 4-methylphenyl, 3-trifluoromethylphenyl, 4-chlorophenyl, 2,4,5-trichlorophenyl and 4-pyridyl.

Examples of compounds in accordance with the invention include:

2-(4-benzenesulfonyl-4-methyl-pentyl)-5-phenyl-2-aza-bicyclo[2.2.1]heptane;
1-(4-benzenesulfonyl-4-methyl-pentyl)-3-thiophen-3-yl-piperidine;
2-(4-benzenesulfonyl-4-methyl-pentyl)-5-(4-fluoro-phenyl)-2-aza-bicyclo[2.2.1]heptane;
2-(4-benzenesulfonyl-4-methyl-pentyl)-5-phenyl-2-aza-bicyclo[2.2.1]heptane;
1-(4-benzenesulfonyl-4-methyl-pentyl)-5-thiophen-2-yl-1,2,3,6-tetrahydro-pyridine;
2-[3-(1-benzenesulfonyl-cyclobutyl)-propyl]-decahydro-isoquinoline;
1-(4-benzenesulfonyl-4-methyl-pentyl)-4,5-dimethyl-1,2,3,6-tetrahydro-pyridine;
1-[3-(1-benzenesulfonyl-cyclobutyl)-propyl]-4-(4-chloro-phenyl)-1,2,3,6-tetrahydro-pyridine;
2-(4-benzenesulfonyl-4-methyl-pentyl)-1,2,3,4-tetrahydro-isoquinoline;
(+/−)-1-(4-benzenesulfonyl-4-methyl-pentyl)-3-thiophen-3-yl-piperidine;
2-(4-benzenesulfonyl-4-methyl-pentyl)-6-furan-2-yl-2-aza-bicyclo[2.2.1]heptane;
2-[4-(4-chloro-benzenesulfonyl)-4-methyl-pentyl]-5-phenyl-2-aza-bicyclo[2.2.1]heptane;
1-(4-benzenesulfonyl-4-methyl-pentyl)-5-furan-2-yl-1,2,3,6-tetrahydro-pyridine;
1-(4-benzenesulfonyl-4-methyl-pentyl)-4-(4-fluoro-phenyl)-1,2,3,6-tetrahydro-pyridine;
2-[3-(1-benzenesulfonyl-cyclopropyl)-propyl]-1,2,3,4-tetrahydro-isoquinoline;
(+/−)-2-[3-(1-benzenesulfonyl-cyclobutyl)-propyl]-decahydro-isoquinoline;
1-(4-benzenesulfonyl-4-methyl-pentyl)-3-thiophen-2-yl-piperidine;
1-(4-benzenesulfonyl-4-methyl-pentyl)-5-furan-3-yl-1,2,3,6-tetrahydro-pyridine;
2-[3-methyl-4-(toluene-3-sulfonyl)-butyl]-1,2,3,4-tetrahydro-isoquinoline;
1-(4-benzenesulfonyl-4-methyl-pentyl)-5-phenyl-1,2,3,6-tetrahydro-pyridine;
1-(4-benzenesulfonyl-4-methyl-pentyl)-3-furan-3-yl-piperidine;
1-[3-(1-benzenesulfonyl-cyclobutyl)-propyl]-4-(4-fluoro-phenyl)-1,2,3,6-tetrahydro-pyridine;
1-[3-(1-benzenesulfonyl-cyclobutyl)-propyl]-4-pyridin-2-yl-piperazine;
2-[3-(1-benzenesulfonyl-cyclobutyl)-propyl]-2,3,3a,4,5,9b-hexahydro-1H-benzo[e]isoindole;
1-[3-(1-benzenesulfonyl-cyclobutyl)-propyl]-3-phenyl-pyrrolidine;
1-(4-benzenesulfonyl-4-methyl-pentyl)-3-furan-2-yl-piperidine;
3-phenyl-1-{3-[1-(2,4,5-trichloro-benzenesulfonyl)-cyclobutyl]-propyl}-pyrrolidine;
2-[3-(1-benzenesulfonyl-cyclobutyl)-propyl]-1,2,3,4-tetrahydro-isoquinoline;
1-(4-benzenesulfonyl-4-methyl-pentyl)-3-phenyl-pyrrolidine;
2-[3-(1-benzenesulfonyl-cyclopropyl)-propyl]-1,2,3,4,5,6,7,8-octahydro-isoquinoline;
2-{3-[1-(toluene-3-sulfonyl)-cyclobutyl]-propyl}-1,2,3,4-tetrahydro-isoquinoline;
2-(4-benzenesulfonyl-4-methyl-pentyl)-decahydro-isoquinoline;
[1-(4-benzenesulfonyl-4-methyl-pentyl)-piperidin-3-yl]-benzyl-methyl-amine;
1-{3-[1-(naphthalene-1-sulfonyl)-cyclobutyl]-propyl}-3-phenyl-pyrrolidine;
2-[4-methyl-4-(toluene-3-sulfonyl)-pentyl]-decahydro-isoquinoline;
2-(4-benzenesulfonyl-4-methyl-pentyl)-5-furan-2-yl-2-aza-bicyclo[2.2.1]heptane;
[1-(4-benzenesulfonyl-4-methyl-pentyl)-piperidin-3-ylmethyl]-methyl-phenyl-amine;
2-[4-methyl-4-(toluene-3-sulfonyl)-pentyl]-1,2,3,4-tetrahydro-isoquinoline;

1-(4-benzenesulfonyl-4-methyl-pentyl)-5-(3-methoxy-phenyl)-1,2,3,6-tetrahydro-pyridine;

4-[1-(4-benzenesulfonyl-4-methyl-pentyl)-1,2,5,6-tetrahydro-pyridin-3-yl]-benzonitrile;

2-(4-benzenesulfonyl-4-methyl-pentyl)-2,3,3a,4,5,9b-hexahydro-1H-benzo[e]isoindole;

3-[1-(4-benzenesulfonyl-4-methyl-pentyl)-piperidin-3-ylmethyl]-1H-indole; and

2-[4-methyl-4-(toluene-2-sulfonyl)-pentyl]-decahydro-isoquinoline;

and the pharmaceutically acceptable salts thereof.

Further examples of compounds in accordance with the invention are provided in the Examples section below.

The invention also provides pharmaceutical compositions comprising one or more of the compounds according to this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, gel-filled capsules, and flavoured emulsions with edible oils such as cottonseed oil, sesame oil or coconut oil, as well as elixirs and similar pharmaceutical vehicles. Suitable dispersing or suspending agents for aqueous gels and suspensions include synthetic and natural gums such as tragacanth, acacia, alginate, dextran, sodium carboxymethylcellulose, methylcellulose, poly(vinyl pyrrolidone), poly(ethylene glycol) and gelatin.

In the treatment of adverse conditions of the central nervous system such as depression or sleep disorders, a suitable dosage level is about 0.01 to 250 mg/kg per day, preferably about 0.05 to 100 mg/kg per day, and especially about 0.05 to 5 mg/kg per day. The compounds may be administered on any suitable regimen, e.g 1 to 4 times per day.

The invention further provides a compound of formula I as defined above, or a pharmaceutically acceptable salt thereof, for use in treatment of the human or animal body. Preferably, said treatment is for a condition which is susceptible to treatment by modulation of $5\text{-HT}_7$ receptor activity, in particular by antagonism of the $5\text{-HT}_7$ receptors, such as depression or a sleep disorder.

The invention further provides the use of a compound of formula I as defined above, or a pharmaceutically acceptable salt thereof, in the manufacture of a medicament for treatment or prevention of a condition which is susceptible to treatment by modulation of $5\text{-HT}_7$ receptor activity, in particular by antagonism of the $5\text{-HT}_7$ receptors, such as depression or a sleep disorder.

There is also disclosed a method of treating a subject suffering from or prone to a condition which is susceptible to treatment by modulation of $5\text{-HT}_7$ receptor activity, in particular by antagonism of the $5\text{-HT}_7$ receptors comprising administering to that subject a therapeutically effective amount of a compound of formula I or a pharmaceutically acceptable salt thereof. Preferably said condition is depression or a sleep disorder.

Compounds of formula I may be prepared by reaction of $(R^1)_2NH$ with compounds of formula (1):

$$Ar\text{---}SO_2\text{---}CR^2R^3\text{-L-X} \qquad (1)$$

where X is leaving group such as halogen (especially bromine or iodine) or alkyl- or arylsulphonate (especially mesylate or tosylate), and $R^1$, $R^2$, $R^3$, Ar and L have the same meanings as before. The reaction may be carried out in refluxing acetonitrile in the presence of a base such as potassium carbonate.

Compounds of formula I in which the $R^1$ groups complete an optionally-substituted tetrahydropyridine ring may alternatively be prepared by reacting a compound of formula (1) with an appropriately-substituted pyridine and reducing the resulting pyridinium salt with sodium borohydride (e.g. in methanol solution at ambient temperature).

Compounds of formula I in which L represents $-CR^{2a}R^{3a}-(CH_2)_n-$ or $-O-CH_2CH_2-$ may alternatively be prepared by reaction of compounds of formula (2) with $(R^1)_2NH$ and sodium triacetoxyborohydride or sodium cyanoborohydride:

$$Ar\text{---}SO_2\text{---}CR^2R^3\text{-L}^1\text{-CHO} \qquad (2)$$

where $L^1$ represents $-CR^{2a}R^{3a}-(CH_2)_{(n-1)}-$ or $-O-CH_2-$, and $R^1$, $R^2$, $R^3$, $R^{2a}$, $R^{3a}$ and Ar have the same meanings as before. The reaction may be carried out in dichloromethane or methanol at ambient temperature.

Compounds of formula I in which L represents —CH$_2$CH(OH)CH$_2$— may alternatively be prepared by reaction of compounds of formula (3) with (R$^1$)$_2$NH:

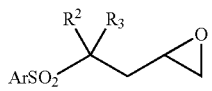

(3)

where R$^1$, R$^2$, R$^3$ and Ar have the same meanings as before. The reaction may be carried out in refluxing acetonitrile in the presence of a base such as potassium carbonate.

Compounds of formula I in which L represents —C≡C—CH$_2$— may alternatively be prepared by reaction of compounds of formula (4) with (R$^1$)$_2$NH and formaldehyde:

(4)

where R$^1$, R$^2$, R$^3$ and Ar have the same meanings as before. The reaction may be carried out in refluxing dioxan in the presence of cuprous chloride.

The compounds of formulae (1), (2), (3) and (4) may be prepared by standard routes, as described in the Examples below.

It will be apparent to those skilled in the art that individual compounds of formula I prepared by the above routes may be converted into other compounds in accordance with formula I by means of well known synthetic techniques such as alkylation, esterification, amide coupling, hydrolysis, coupling mediated by organometallic species, oxidation and reduction. Such techniques may likewise be carried out on precursors of the compounds of formula I.

For example, compounds of formula I (or their precursors) in which one or both of R$^2$ and R$^3$ are H may be converted into the corresponding compounds in which R$^2$ and/or R$^3$ is alkyl by treatment with an alkyl halide in the presence of base.

In a further example of this protocol, compounds of formula I (or their precursors) in which N(R$^1$)$_2$ represents a 5-bromo-1,2,3,5,6-tetrahydropyridine ring may be reacted with R$^4$—B(OH)$_2$ to provide the corresponding 5-R$^4$-substituted 1,2,3,5,6-tetrahydropyridines, where R$^4$ has the same meaning as before. Advantageously, in this context R$^4$ represents optionally-substituted phenyl or heteroaryl. The reaction takes place in dioxan at 80° C. in the presence of a base such as potassium carbonate and a Pd catalyst such as (Ph$_3$P)$_4$Pd(0). If desired, the 5-R$^4$-substituted 1,2,3,5,6-tetrahydropyridines may be hydrogenated (e.g. in ethanol over a Pd catalyst) to provide the corresponding 3-R$^4$-substituted piperidine derivatives.

It will be appreciated that many of the above-described synthetic schemes may give rise to mixtures of stereoisomers. Such mixtures may be separated by conventional means such as fractional crystallisation and preparative chromatography.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC or the formation of diastereomeric pairs by salt formation with an optically active acid, such as (-)-di-p-toluoyl-d-tartaric acid and/or (+)-di-p-toluoyl-1-tartaric acid, followed by fractional crystallisation and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 3$^{rd}$ ed., 1999. The protecting groups may be removed at a convenient subsequent stage using methods known from the art.

The ability of the compounds according to the invention to bind to 5-HT$_7$ receptor sites may be measured as described in WO 97/29097 or by analogous methods.

EXAMPLES

Description 1

1,1-Bis(phenylsulfonyl)cyclobutane

A mixture of bis(phenylsulfonyl)methane (30 g, 100 mmol), tetra-n-butylammonium bromide (3 g, 9.3 mmol), 1,3-dibromopropane (30 ml), dichloromethane (600 ml) and 50% aqueous sodium hydroxide (150 ml) was stirred at room temperature for 3 days. The mixture was poured onto saturated aqueous ammonium chloride solution and extracted into dichloromethane. The combined organic extracts were dried (Na$_2$SO$_4$) and concentrated. The residue was crystallised from i-hexane:diethyl ether to give the title product as a white solid. Yield–24 g (71%).

$\delta_H$ (360 MHz, CDCl$_3$): 8.03 (4H, m), 7.71 (2H, m), 7.57 (4H, m), 2.95 (4H, t, J 8.4 Hz), 2.14 (2H, pentet, J 8.4 Hz).

Description 2

Cyclopropanesulphonylbenzene

A solution of cyclopropyl phenyl sulfide (10.5 g, 70 mmol) and Oxone™ (55.13 g, 175 mmol) in methanol (30 ml) was stirred at room temperature for 5 hours. The mixture was diluted was water and extracted with ethyl acetate. The combined organic layers were dried (MgSO$_4$) and concentrated in vacuo.

$\delta_H$ (400 MHz, CDCl$_3$): 7.95–7.90 (2H, m), 7.76–7.62 (1H, m), 7.59–7.54 (2H, m), 2.50–2.44 (1H, m), 1.38–1.1.33 (2H, m), 1.06–1.01 (2H, m).

Description 3

1-Methyl-2-(propane-2-sulphonyl)benzene

A mixture of 2-methylbenzenethiol (2.37 ml, 20 mmol), potassium carbonate (6.91 g, 50 mmol) and 2-iodopropane (6.00 ml, 60 mmol) in acetonitrile (20 ml) was stirred at 60° C. for 3 days. The mixture was diluted with water and extracted with ethyl acetate. The combined organic layers were dried (MgSO$_4$) and concentrated in vacuo. The residue was dissolved in methanol (10 ml) and water (2 ml), treated with Oxone™ (18.51 g, 30 mmol) and stirred at room temperature for 3 hours. The mixture was concentrated in vacuo and the residue partitioned between ethyl acetate and water. The organic layer was dried (MgSO$_4$) and concentrated in vacuo to give the title compound (3.44 g, 87%).

δ$_H$ (400 MHz, CDCl$_3$): 7.97 (1H, dd, J 1.3, 7.9 Hz), 7.51 (1H, dt, J 1.4, 7.5 Hz), 7.39–7.32 (2H, m), 3.31–3.21 (1H, m), 2.69 (3H, s), 1.30 (6H, d, J 6.8 Hz).

Description 4

1-Cyclobutanesulfonyl-naphthalene

A mixture of naphthalene-1-thiol (1.17 g, 7.3 mmol), cyclobutyl bromide (1.45 g, 10.7 mmol), potassium carbonate (1.06 g, 7.7 mmol) and acetonitrile (20 ml) was stirred at 70° C. for 40 hours. the mixture was poured into water and extracted into ethyl acetate. The combined organic extracts were dried (Na$_2$SO$_4$) and concentrated. The residue was treated with dichloromethane (30 ml), acetone (5 ml), 10% aqueous potassium bicarbonate and 18-crown-6 (100 mg, 0.4 mmol) and a solution of Oxone™ (10 g) in water (100 ml) was added. After completion, the layers were separated and the aqueous phase was extracted with dichloromethane. The combined organic extracts were dried (Na$_2$SO$_4$) and concentrated. The residue was purified on silica (i-hexane-ethyl acetate) to give the title product (257 mg, 14%).

δ$_H$ (360 MHz, CDCl$_3$): 8.79 (1H, m), 8.40 (1H, m), 8.12 (1H, d, J 7.2 Hz), 8.12 (1H, d, J 8.6 Hz), 7.72 (3H, m), 4.06 (1H, pentet, J 8.1 Hz), 2.59 (2H, m), 2.20–1.87 (4H, m).

Description 5

1-Cyclobutanesulfonyl-3-methylbenzene

The title compound was prepared as described in Description 4 from 3-methylbenzenethiol.

δ$_H$ (360 MHz, CDCl$_3$): 7.68 (2H, m), 7.44 (2H, m), 3.81 (1H, pentet, J 8.1 Hz), 2.56 (2H, m), 2.34 (3H, s), 2.18 (2H, m), 1.99 (2H, m).

Description 6

1-Cyclobutanesulfonyl-2,4,5-trichlorobenzene

The title compound was prepared as described in Description 4 from 2,4,5-trichlorobenzenethiol.

δ$_H$ (360 MHz, CDCl$_3$): 8.20 (1H, s), 7.64 (1H, s), 4.32 (1H, pentet, J 8.1 Hz), 2.57 (2H, m), 2.23 (2H, m), 1.89 (2H, m).

Description 7

[1-(3-Bromopropyl)-cyclobutanesulfonyl]benzene

A solution of lithium napthtalenide in tetrahydrofuran (4.3M, 60 ml) was added to a stirred solution of 1,1-bis(phenylsulfonyl)cyclobutane (4.15 g, 12.35 mmol) at −78° C. over 20 min. The mixture was stirred for 15 min. and 1,3-dibromopropane (10 ml) was added in one portion. The cold bath was removed and the mixture was stirred at ambient temperature for 2 hours. The reaction mixture was treated with saturated aqueous ammonium chloride solution and extracted into ethyl acetate. The combined organic extracts were washed with brine, dried (Na$_2$SO$_4$) and concentrated. The residue was purified on silica gel to give the title product (2.55 g, 65%).

δ$_H$ (360 MHz, CDCl$_3$): 7.88 (2H, m), 7.67 (1H, m), 7.57 (2H, m), 7.29 (2H, m), 3.39 (2H, t, J 6.3 Hz), 2.86 (2H, m), 2.12 (2H, m), 1.97 (2H, m), 1.84 (2H, m).

Description 8

(4-Bromobutane-1-sulfonyl)benzene

A mixture of benzenethiol sodium salt (10 g, 75 mmol), 1,4-dibromobutane (20 ml) and tetrahydrofuran (100 ml) was stirred at room temperature. After 20 hours, the mixture was poured into water and extracted into i-hexane. The combined organic extracts were dried (Na$_2$SO$_4$) and concentrated. The residue was treated with methanol (300 ml) and a solution of Oxone™ (70 g) in water (300 ml) was added in 50-ml portions. After completion, the mixture was diluted with water and extracted into ethyl acetate. The combined organic extracts were dried (Na$_2$SO$_4$) and concentrated. The residue was purified on silica to give the title product.

δ$_H$ (400 MHz, CDCl$_3$): 7.92 (2H, m), 7.68 (1H, m), 7.59 (2H, m), 3.37 (2H, t, J 6.3 Hz), 3.12 (2H, m), 2.03–1.84 (4H, m).

Description 9

[1-(4-Bromobutyl)-cyclobutanesulfonyl]benzene

The title compound was prepared as described in Description 7 from 1,1-bis(phenylsulfonyl)cyclobutane and 1,4-dibromobutane.

δ$_H$ (400 MHz, CDCl$_3$): 7.87 (2H, m), 7.66 (1H, m), 7.56 (2H, m), 3.39 (2H, t, J 6.6 Hz), 2.85 (2H, m), 2.05–1.78 (6H, m), 1.71–1.64 (4H, m).

Description 10

(5-Bromo-2-methylpentane-2-sulfonyl)benzene

A solution of n-butyllithium in cyclohexanes (1.82M, 18 ml, 32.8 mmol) was added dropwise to a stirred solution of phenyl i-propyl sulphone (5.55 g, 30.1 mmol) in tetrahydrofuran (60 ml) at −78° C. The mixture was stirred for 30 min. and 1,3-dibromopropane (6 ml, 58.7 mmol) was added via syringe over 30 seconds. The mixture was allowed to warm to 0° C. over 3 hours, then quenched with satd. aqueous NH$_4$Cl and extracted into 1:1 mixture of i-hexane-diethyl ether. The combined organic extracts were dried (Na$_2$SO$_4$) and concentrated. The residue was purified on silica (i-hexane-diethyl ether) to give the title product (5.7 g, 62%) as a white solid.

δ$_H$ (400 MHz, CDCl$_3$): 7.88 (2H, m), 7.67 (1H, m), 7.57 (2H, m), 3.39 (2H, t, J 6.6 Hz), 2.03–1.94 (2H, m), 1.88–1.84 (2H, m), 1.31 (6H, s).

Description 11

[1-(3-Bromopropyl)cyclopropane-1-sulfonyl]benzene

The title compound was prepared as described in Description 10 from the product of Description 2.

δ$_H$ (400 MHz, CDCl$_3$): 7.89–7.87 (2H, m), 7.68–7.63 (1H, m), 7.59–7.55 (2H, m), 3.36 (2H, t, J 6.2 Hz), 2.05–1.99 (2H, m), 1.73–1.67 (2H, m), 1.65–1.61 (2H, m), 0.91–0.88 (2H, m).

Description 12

1-[1-(3-Bromopropyl)-cyclobutanesulfonyl]naphthalene

The title compound was prepared as described in Description 10 from the product of Description 4.

$\delta_H$ (400 MHz, CDCl$_3$): 8.90 (1H, d, J 8.8 Hz), 8.29 (1H, dd, J 1.4 and 7.6 Hz), 8.13 (1H, d, J 8.4 Hz), 7.94 (1H, dd, J 1.4 and 7.4 Hz), 7.70–7.56 (3H, m), 3.29 (2H, t, J 6.3 Hz), 2.94 (2H, m), 2.12–1.82 (8H, m).

Description 13

1-[1-(3-Bromopropyl)-cyclobutanesulfonyl]-3-methylbenzene

The title compound was prepared as described in Description 10 from the product of Description 5 to give a 1:1 mixture of starting 1-cyclobutanesulfonyl-3-methyl-benzene and the title product that was used in the next step without further purification.

Description 14

1-[1-(3-Bromopropyl)cyclobutanesulfonyl]-2,4,5-trichlorobenzene

The title compound was prepared as described in Description 10 from the product of Description 6.

$\delta_H$ (400 MHz, CDCl$_3$): 8.17 (1H, s), 7.65 (1H, s), 3.36 (2H, t, J 8.1 Hz), 3.01 (2H, m), 2.14–1.85 (8H, m).

Description 15

3-Benzenesulfonyl-3-methyl-butan-1-ol

A solution of n-butyllithium in cyclohexanes (1.8M, 35.1 ml; 63.18 mmol) was added dropwise to a stirred solution of isopropyl phenyl sulphone (9.95 g, 54 mmol) in tetrahydrofuran (100 ml) keeping the temperature of the mixture below –60° C. The mixture was stirred for 30 min. and ethylene oxide was passed through the reaction mixture for 10 min. The mixture was warmed up to –40° C. for 30 min., then quenched with sat. aqueous NH$_4$Cl and extracted into ethyl acetate. The combined organic extracts were dried (Na$_2$SO$_4$) and concentrated. The residue was purified on silica gel (i-hexane:ethyl acetate) to give the title compound (12.3 g, 99%).

$\delta_H$ (400 MHz, CDCl$_3$): 7.89 (2H, m), 7.67 (1H, m), 7.57 (2H, m), 3.84 (2H, t, J 6.7 Hz), 2.06 (1H, br), 2.01 (2H, t, J 6.7 Hz), 1.36 (6H, s).

Description 16

Methanesulfonic acid 3-benzenesulfonyl-3-methylbutyl ester

A solution of 3-benzenesulfonyl-3-methyl-butan-1-ol (2.17 g, 9.5 mmol), triethylamine (2.0 ml, 14.25 mmol), methanesulphonyl chloride (0.9 ml, 11.78 mmol) and 4-N,N-dimethylaminopyridine (12 mg, 0.01 mmol) was stirred at 0° C. for 45 min. After quenching with satd. NaHCO$_3$, the mixture was extracted into dichloromethane. The combined organic extracts were dried (Na$_2$SO$_4$) and concentrated to give the title product (3.0 g).

$\delta_H$ (400 MHz, CDCl$_3$): 7.88 (2H, m), 7.69 (1H, m), 7.59 (2H, m), 4.48 (2H, t, J 7.0 Hz), 3.03 (3H, m), 2.21 (2H, t, J 7.0 Hz), 1.37 (6H, s).

Description 17

(4-Chlorobut-2-ene-1-sulphonyl)benzene

A solution of benzenethiol sodium salt (896 μL, 8.02 mmol) in N,N-dimethylformamide (10 ml) was added dropwise to trans-1,4-dichloro-2-butene (5.01 g, 40.1 mmol) in N,N-dimethylformamide (10 ml) at –5° C. The mixture was allowed to warm to room temperature then diluted with water and extracted with ethyl acetate. The combined organic layers were dried (MgSO$_4$) and concentrated in vacuo. The residue was dissolved in methanol (10 ml) and treated with Oxone™ (7.4 g, 12.03 mmol). The reaction was stirred at room temperature for 48 hours. The mixture was diluted with water and extracted with ethyl acetate. The combined organic layers were dried (MgSO$_4$) and concentrated in vacuo. The residue was purified by flash column chromatography on silica, eluting with 25% ethyl acetate/i-hexane, to give the title compound as a clear oil (733 mg, 40%).

$\delta_H$ (400 MHz, CDCl$_3$): 7.89–7.86 (2H, m), 7.69–7.65 (1H, m), 7.59–7.55 (2H, m), 5.82–5.74 (1H, m), 5.71–5.64 (1H, m), 3.99–3.96 (2H, m), 3.82–3.80 (2H, m).

Description 18

2-(4-Benzenesulphonylbutoxy)tetrahydropyran

A mixture of thiophenol (5.02 ml, 49 mmol), 4-chloro-1-butanol (7.33 ml, 73.5 mmol) and potassium carbonate (20.32 g, 147 mmol) in acetonitrile (5 ml) was stirred at 60° C. for 18 hours. The cooled mixture was diluted with water and extracted with ethyl acetate. The combined organic layers were concentrated in vacuo. The residue was dissolved in methanol (10 ml) and water (2 ml) and treated with Oxone™ (45.2 g, 73.5 mmol). The reaction was stirred at room temperature for 24 hours, then filtered and concentrated in vacuo. The residue was partitioned between ethyl acetate and water. The organic layer was concentrated to give an oil which was dissolved in dichloromethane (10 ml), treated with pyridinium p-toluenesulfonate (3.69 g, 14.7 mmol) and 3,4-dihydro-2H-pyran (13.35 ml, 147 mmol) and stirred at room temperature for 18 hours. The mixture was diluted with water and the layers separated. The organic layer was washed with saturated aqueous sodium hydrogen carbonate solution and concentrated in vacuo. The residue was purified by flash column chromatography on silica gel, eluting with 25% ethyl acetate/i-hexane, to yield the title compound as a clear oil (3.5 g, 24%).

$\delta_H$ (360 MHz, CDCl$_3$): 7.93–7.90 (2H, m), 7.68–7.64 (1H, m), 7.59–7.55 (2H, m), 4.52 (1H, t, J 3.6 Hz), 3.80–3.65 (2H, m), 3.50–3.44 (1H, m), 3.39–3.32 (1H, m), 3.18–3.12 (2H, m), 1.88–1.74 (6H, m), 1.71–1.46 (4H, m).

Description 19

3-(1-Benzenesulphonylcyclopent-3-enyl)propan-1-ol

A solution of 2-(4-benzenesulphonylbutoxy)tetrahydropyran (3.4 g, 11.4 mmol) in tetrahydrofuran (15 ml) was cooled to –78° C., treated with butyl lithium (1.6M in hexanes, 15 ml, 23.9 mmol) and stirred for 10 minutes. Allyl bromide (2.12 ml, 25.08 mmol) was added and the mixture allowed to warm to room temperature, then diluted with water and extracted with ethyl acetate. The organic layers were dried (MgSO$_4$) and concentrated in vacuo to give a clear oil (3.1 g, contaminated with mono-allylated compound). 1.14 g of this was dissolved in dichloromethane (100 ml) and treated with bis(tricyclohexylphosphine)benzylidene-ruthenium (IV) dichloride (260 mg, 0.32 mmol). The reaction was stirred for 3 hours at room temperature then concentrated in vacuo and purified by flash column chromatography on silica, eluting with 20% ethyl acetate/i-hexane to yield the cyclopentenyl compound (762 mg, contaminated with mono-allylated compound). This was dissolved in methanol (5 ml). p-Toluenesulphonic acid monohydrate (50 mg, 0.26 mmol) was added and the reaction stirred at room temperature for 5 hours. The mixture was diluted with water and concentrated in vacuo to remove the methanol. The mixture was then extracted with ethyl acetate and the combined organic layers dried (MgSO$_4$) and concentrated in vacuo. The residue was purified by flash column chromatography using a Jones Personal Flashmaster, eluting with 25% ethyl acetate/i-hexane, to yield the title compound as a white crystalline solid (56 mg, 5%).

$\delta_H$ (400 MHz, CDCl$_3$): 7.93–7.90 (2H, m), 7.67–7.63 (1H, m), 7.57–7.53 (2H, m), 5.55 (2H, s), 3.64–3.60 (2H, m), 3.25 (2H, d, J 15 Hz), 2.33 (2H, d, J 15 Hz), 1.86–1.82 (2H, m), 1.59–1.50 (2H, m).

Description 20

1-(5-Bromo-2-methylpentane-2-sulphonyl)-2-methylbenzene

The title compound was prepared from the product of Description 3 by the method in Description 10, to give a 1:1 mixture of title compound and dibromopropane which was used crude.

$\delta_H$ (360 MHz, CDCl$_3$): 7.90–7.86 (1H, m), 7.53–7.49 (1H, m), 7.38–7.32 (2H, m), 3.40 (2H, t, J 6.3 Hz), 2.73 (3H, s), 1.98–1.95 (2H, m), 1.93–1.88 (2H, m), 1.31 (6H, s).

Description 21

(3R*,4R*)-4-Benzenesulfonyl-3-methylpentan-1-ol.

A solution of n-butyllithium in hexanes (7.48 ml, 11.22 mmol) was added dropwise to a stirred solution of ethyl phenyl sulphone (1.87 g, 11 mmol) in THF (25 ml) at −78° C. The mixture was stirred for 30 min. and 1,3-dimethyl-3,4,5,6-tetrahydro-2(1H)-pyrimidinone (1.5 ml, 12.43 mmol) was added followed by methyl crotonate (2.0 ml, 18.7 mmol). The reaction mixture was stirred for 90 min., quenched with sat. aqueous NH$_4$Cl and extracted into ethyl acetate. The organic extract was dried (Na$_2$SO$_4$) and concentrated to give 4-benzenesulfonyl-3-methylpentanoic acid methyl ester as a 8:1 mixture of diastereoisomers that was dissolved in dichloromethane (20 ml) and cooled using a ice-bath. A solution of diisobutyl aluminium hydride in dichloromethane (50.0 ml, 50.0 mmol) was added and the reaction mixture was stirred at room temperature for 30 min. Ethyl acetate (10 ml) was added and the resulting mixture was poured into dichloromethane (200 ml) and cooled with an ice-bath. Water (4 ml) was added dropwise and the mixture was stirred for 30 min. dried over Na$_2$SO$_4$ for 30 min. filtered through a pad of Celite and concentrated. The residue was purified on silica gel (i-hexane-ethyl acetate) to give the title product.

$\delta_H$ (360 MHz, CDCl$_3$): 7.90 (2H, d, J 7.0 Hz), 7.65 (1H, t, J 7.0 Hz), 7.57 (2H, t, J 7.0 Hz), 3.76 (1H, m), 3.65 (1H, m), 3.03 (1H, dq, J 2.5 and 7.0 Hz), 2.49 (1H, m), 2.14 (1H, m), 1.78 (1H, br), 1.39 (1H, ddd, J 5.6, 10.9 and 15.8 Hz), 1.26 (3H, d, J 7.0 Hz), 1.03 (3H, d, J 7.0 Hz).

Description 22

(3R*,4S*)-4-Benzenesulfonyl-3-methylpentan-1-ol n-Butyllithium in hexanes (0.165 ml, 0.25 mmol) was added dropwise to a stirred solution of (3R*,4R*)-4-benzenesulfonyl-3-methylpentan-1-ol (286 mg, 1.2 mmol) in THF (5 ml) at −78° C. The mixture was warmed to 0° C. over 30 min. and quenched with satd. aqueous NH$_4$Cl and extracted with dichloromethane. The combined organic extracts were dried (Na$_2$SO$_4$) and concentrated to give a mixture syn:anti diastereoisomeric sulfones in a 6:1 ratio respectively.

$\delta_H$ (400 MHz, CDCl$_3$): 7.89 (2H, m), 7.65 (1H, m), 7.56 (2H, m), 3.76 (1H, m), 3.65 (2H, m), 3.14 (1H, dq, J 2.4 and 7.0 Hz), 2.54 (1H, ddq, J 2.4, 7.0 and 13.7 Hz), 1.59 (1H, br), 1.55 (1H, m), 1.22 (3H, d, J 7.0 Hz), 1.05 (3H, d, J 7.0 Hz).

Description 23

Methanesulfonic acid (3R*,4S*)-4-benzenesulfonyl-3-methylpentyl ester

Methanesulphonyl chloride (0.077 ml, 1 mmol) was added to an ice-bath cooled and stirred solution of (3R*,4S*)-4-benzenesulfonyl-3-methylpentan-1-ol (55.7 mg, 0.23 mmol) and triethylamine (0.2 ml, 1.43 mmol) in dichloromethane (1 ml). The mixture was stirred for 30 min., then quenched with satd. aqueous NaHCO$_3$ and extracted with dichloromethane. The combined organic extracts were dried (Na$_2$SO$_4$) and concentrated to give crude mesylate that was used in the next step without purification.

Description 24

2,2-Dimethylpent-4-en-1-ol

A solution of lithium aluminium hydride in diethyl ether (1M, 15.75 ml) was added dropwise to an ice-bath cooled and stirred solution of 2,2-dimethyl-4-pentenal (3.528 g, 31.5 mmol) in diethyl ether (20 ml). The mixture was stirred for 30 min. and carefully quenched with 4M NaOH (30 ml). The mixture was extracted into diethyl ether. The combined organic extracts were dried (Na$_2$SO$_4$) and concentrated to give the title product (3.2 g, 89%).

$\delta_H$ (400 MHz, CDCl$_3$): 5.85 (1H, m), 5.05 (2H, m), 3.33 (2H, s), 3.65 (2H, m), 2.02 (2H, d, J 7.4 Hz), 1.47 (1H, br), 0.89 (6H, s).

Description 25

(2,2-Dimethylpent-4-ene-1-sulfonyl)benzene

Diethyl azodicarboxylate (3.8 ml, 23.8 mmol) was added to an ice-bath cooled and stirred solution of benzenethiol (2.63 ml, 25.5 mmol) and triphenylphosphine (6.24 g, 23.8 mmol) in tetrahydrofuran (20 ml). The mixture was stirred at 48° C. for 4 days. Water (0.2 ml) was added and the mixture was concentrated in vacuo. The residue was purified on silica gel to give thioether that was dissolved in methanol (70 ml) and a solution of Oxone™ (33 g, 54.4 mmol) in water (150 ml) was added over 15 min. The resulting mixture was stirred for 2 hours, treated with water (250 ml) and extracted into dichloromethane (3×50 ml). The combined organic extracts were dried ($Na_2SO_4$) and concentrated. The residue was purified on silica gel (i-hexane-ethyl acetate 0–15%) to give the title product (2.04 g, 50%).

$\delta_H$ (400 MHz, $CDCl_3$): 7.91 (2H, m), 7.63 (1H, m), 7.55 (2H, m), 5.59 (1H, ddt, J 7.4, 10.6 and 16.4 Hz), 5.12 (1H, m), 5.09 (1H, m), 3.01 (2H, s), 2.25 (2H, dt, J 1.2 and 7.4 Hz), 1.19 (6H, s).

Description 26

4-Benzenesulphonyl-3-methylbutan-1-ol

A solution of methanesulphonylbenzene (2.17 g, 13.9 mmol) in tetrahydrofuran (10 ml) was cooled to −78° C. and treated with butyllithium (1.6M in hexanes, 8.7 ml, 13.9 mmol) followed by 1,3-dimethyl-3,4,5,6-tetrahydro-2(1H)-pyrimidinone (1.68 ml, 13.9 mmol). The reaction was stirred at −78° C. for 15 minutes then methyl crotonate (7.36 ml, 69.5 mmol) added. The reaction was allowed to warm to room temperature and quenched with water. The mixture was extracted with ethyl acetate and the combined organic layers dried ($MgSO_4$) and concentrated in vacuo. The residue was dissolved in dichloromethane (10 ml) and cooled to −5° C. A solution of diisobutylaluminium hydride in dichloromethane (1M, 27.8 ml, 27.8 mmol) was added and the reaction allowed to warm to room temperature. The mixture was diluted with aqueous ammonium carbonate solution and extracted with ethyl acetate. The combined organic layers were dried ($MgSO_4$) and concentrated in vacuo. A portion of the residue was purified by preparative thin layer chromatography, eluting with 5% methanol/dichloromethane, to give the title compound.

$\delta_H$ (360 MHz, $CDCl_3$): 7.95–7.88 (2H, m), 7.70–7.62 (1H, m), 7.60–7.55 (2H, m), 3.73–3.61 (2H, m), 3.25–3.20 (1H, m), 3.02–2.96 (1H, m), 2.35–2.28 (1H, m), 1.96–1.55 (2H, m), 1.09 (3H, d, J 6.8 Hz).

Description 27

1-Methyl-3-(2-methylbut-3-enylsulfanyl)benzene

A mixture of 3-methylbenzenethiol (1.80 ml, 23.82 mmol), 2-methyl-3-buten-1-ol (2.73 ml, 26.47 mmol) and triphenylphosphine (6.94 g, 26.47 mmol) in dichloromethane (10 ml) was treated with diethyl azodicarboxylate (4.59 ml, 29.12 mmol) at room temperature. The mixture was concentrated in vacuo and dissolved in diethyl ether to remove triphenylphosphine oxide. The organic phase was purified by flash column chromatography on silica, eluting with hexane, to afford the title compound as a clear oil (1.01 g, 20%).

$\delta_H$ (400 MHz, $CDCl_3$): 7.20–7.11 (3H, m), 6.98–6.96 (1H, m), 5.85–5.76 (1H, m), 5.08–5.00 (2H, m), 2.98–2.92 (1H, m), 2.85–2.80 (1H, m), 2.47–2.40 (1H, m), 2.32 (3H, s), 1.14 (3H, d, J 6.7 Hz).

Description 28

1-Methyl-3-(2-methylbut-3-ene-1-sulphonyl)benzene

Prepared from 1-methyl-3-(2-methylbut-3-enylsulfanyl) benzene by the method in Description 2.

$\delta_H$ (400 MHz, $CDCl_3$): 7.74–7.67 (2H, m), 7.48–7.42 (2H, m), 5.73 (1H, ddd, J 7.0, 10.2 and 17.2 Hz), 5.01 (1H, dt, J 1.6 and 17.2 Hz), 4.97 (1H, dt, J 1.6 and 10.2 Hz), 3.15 (1H, dd, J 5.9 and 14.1 Hz)), 3.03 (1H, dd, J 7.0 and 14.1 Hz), 2.80 (1H, m), 2.45 (3H, s), 1.18 (3H, d, J 6.7 Hz).

Description 29

3-Methyl-4-(3-methylbenzenesulphonyl)pentan-1-ol

1-Methyl-3-(2-methylbut-3-ene-1-sulphonyl)benzene (444 mg, 1.96 mmol) was dissolved in tetrahydrofuran (5 ml) and cooled to −78° C. n-Butyllithium (1.6M in hexanes, 1.96 mmol) was added. The reaction was treated with methyl iodide (130 μL, 2.16 mmol) and allowed to warm to room temperature. The mixture was quenched with saturated aqueous ammonium chloride solution and extracted with ethyl acetate. The combined organic layers were dried ($MgSO_4$) and concentrated in vacuo to give a 1:1 mixture of dimethyl diastereoisomers containing approximately 28% monomethyl starting material. This crude mixture (265 mg, 1.12 mmol) was dissolved in tetrahydrofuran (3 ml) at 0° C. and treated with borane-tetrahydrofuran complex (1.0M in tetrahydrofuran, 4.5 ml, 4.5 mmol) then allowed to warm to room temperature and stirred for 6 hours. The reaction was treated cautiously with pre-mixed hydrogen peroxide 35% w/w (5 ml) and water (5 ml) and stirred for 18 hours. The reaction mixture was extracted with ethyl acetate and the combined organic layers were concentrated in vacuo to give a clear oil which was purified by preparative thin layer chromatography, eluting with 25% ethyl acetate/i-hexane to give a 1:1 mixture of diastereoisomers that was used in the next step.

Description 30

1-Methyl-3-(propane-2-sulphonyl)benzene

Prepared from 3-methylbenzenethiol by the method in Description 3.

$\delta_H$ (400 MHz, $CDCl_3$): 7.71–7.65 (2H, m), 7.47–7.42 (2H, m), 3.19 (1H, pentet, J 6.6 Hz), 2.45 (3H, s), 1.29 (6H, d, J 7.0 Hz).

Description 31

2-[4-(3-Methylbenzenesulfonyl)butoxy]tetrahydropyran

Prepared from 3-methylbenzenethiol by the method in Description 18.

$\delta_H$ (360 MHz, $CDCl_3$): 7.75–7.66 (2H, m), 7.48–7.41 (2H, m), 4.52 (1H, t, J 3.5 Hz), 3.81–3.67 (2H, m), 3.47 (1H, m), 3.36 (1H, dt, J 5.9 and 10.2 Hz), 3.14 (2H, m), 2.45 (3H, s), 1.88–1.44 (10H, m).

Description 32

4-Methyl-4-(3-methylbenzenesulfonyl)pentan-1-ol

The product of Description 31 (430 mg, 1.39 mmol) was dissolved in tetrahydrofuran (3 ml) and cooled to −78° C. n-Butyllithium (1.6M in hexanes, 1.74 ml, 2.78 mmol) was added and the reaction stirred for 20 minutes. Methyl iodide (0.2 ml, 3.0 mmol) was added and the mixture allowed to warm to room temperature The mixture was diluted with saturated ammonium chloride and the organics extracted with ethyl acetate. The organics were separated, dried (magnesium sulfate) and concentrated in vacuo. The residue was treated with methanol (6 ml) and p-toluenesulphonic acid (50 mg, 0.3 mmol) and stirred at room temperature overnight. The mixture was diluted with water and the organics extracted into dichloromethane. The organics were dried (magnesium sulfate) and concentrated in vacuo. The residue was purified by flash column chromatography eluting with 50% i-hexane/ethyl acetate (180 mg, 50%).

$\delta_H$ (400 MHz, CDCl$_3$): 7.72–7.65 (2H, m), 7.47–7.41 (2H, m), 3.65 (1H, t, J 6.3 Hz), 2.45 (3H, s), 1.87–1.60 (5H, m), 1.30 (6H, s).

Description 33

1-Methyl-4-(propane-2-sulfonyl)benzene

Prepared from 4-methylbenzenethiol by the method in Description 3.

$\delta_H$ (360 MHz, CDCl$_3$): 7.76 (2H, d, J 8.4 Hz), 7.35 (2H, d, J 8.1 Hz), 3.17 (1H, pentet, J 6.7 Hz), 2.45 (3H, s), 1.29 (6H, d, J 6.7 Hz).

Description 34

1-(5-Bromo-2-methylpentane-2-sulfonyl)-4-methyl-benzene

Prepared from 1-methyl-4-(propane-2-sulfonyl)-benzene by the method in Description 10.

$\delta_H$ (360 MHz, CDCl$_3$): 7.74 (2H, m), 7.35 (2H, m), 3.56 (1H, t, J 6.3 Hz), 2.46 (3H, s), 2.08–1.50 (4H, m), 1.29 (6H, s).

Description 35

4-Isopropylsulfanylpyridine

A mixture of 4-mercaptopyridine (7 g, 63 mmol), 2-bromopropane (7.0 ml, 75.6 mmol), and potassium carbonate (10.2 g, 73.7 mmol) was stirred at room temperature for 6 hours and left overnight. The solid was filtered off and the filtrate was concentrated in vacuo. The residue was purified by chromatography on silica gel (i-hexane:ethyl acetate) to give the title product (7.4 g, 63%). The hydrochloride salt was prepared by treatment of the title compound with ethereal HCl.

$\delta_H$ (360 MHz, CDCl$_3$): 8.40 (2H, d, J 5.9 Hz), 7.12 (2H, d, J 6.3 Hz), 3.60 (1H, heptet, J 6.7 Hz), 1.39 (6H, d, J 6.7 Hz); m/z (ES$^+$) 154 (M+H)$^+$.

Description 36

4-(Propane-2-sulfonyl)pyridine

Oxone™ (4.8 g, 7.9 mmol) was added in batches (ca. 1 g) to a stirred mixture of 4-ipropylsulfanylpyridine hydrochloride (870 mg, 4.57 mmol), grade IV alumina (5 g) and chloroform (20 ml) at +40° C. After completion, the mixture was filtered and the filtrate was concentrated in vacuo at low temperature (<25° C.). The residue was treated with 2M ammonia in methanol, concentrated and purified by chromatography on silica (dichloromethane:methanol) to give the title product (150 mg, 15%).

$\delta_H$ (400 MHz, CDCl$_3$): 8.93 (2H, m), 7.77 (2H, m), 3.26 (1H, heptet, J 7.0 Hz), 1.32 (6H, d, J 7.0 Hz).

Description 37

4-(5-Bromo-2-methylpentane-2-sulfonyl)pyridine

A solution of n-butyllithium in hexanes (1.6M, 0.81 ml; 1.3 mmol) was added to a stirred solution of 2,2,6,6,-tetramethylpiperidine (0.23 ml, 1.37 mmol) in tetrahydrofuran (3 ml) at −20° C. The mixture was stirred for 30 min. and cooled to −78° C. A solution of product of Description 36 in tetrahydrofuran (3 ml) was added. The mixture was stirred for 15 min. and 1,3-dibromopropane (0.4 ml) was added. The mixture was warm up slowly to 0° C. over 2 hours and quenched with sat. aqueous NH$_4$Cl. The mixture was extracted into dichloromethane, dried (Na$_2$SO$_4$) and concentrated. The residue was purified by chromatography on silica (i-hexane:ethyl acetate 1:1) to give the title product (120 mg, 48%).

$\delta_H$ (400 MHz, CDCl$_3$): 8.92 (2H, m), 7.75 (2H, m), 3.41 (2H, t, J 6.7 Hz), 2.05–1.94 (2H, m), 1.86 (2H, m), 1.33 (6H, s).

Description 38

4-Chloro-2-(propane-2-sulphonyl)benzene

The title compound was prepared as described in Description 3 from 4-chlorobenzenethiol.

$\delta_H$ (400 MHz, CDCl$_3$): 7.82 (2H, m), 7.55 (2H, m), 3.40 (1H, pentet, J 7 Hz), 1.30 (6H, d, J 7 Hz).

Description 39

1-(5-Bromo-2-methylpentane-2-sulphonyl)-4-chlorobenzene

The title compound was prepared as described in Description 10 from 4-chloro-2-(propane-2-sulphonyl)benzene.

$\delta_H$ (400 MHz, CDCl$_3$): 7.82 (2H, dd, J 1.8 and 6.7 Hz), 7.55 (2H, dd, J 1.8 and 6.7 Hz), 3.40 (2H, t, J 6.4 Hz), 2.01–1.95 (2H, m), 1.85–1.82 (2H, m), 1.30 (6H, s).

Description 40

3-Cyclopentylpyridine

3-Bromopyridine (3.9 ml, 40 mmol) and [1,2-bis(diphenylphosphino)ethane]dichloronickel(II) (160 mg, 0.3 mmol) were dissolved in dry tetrahydrofuran (25 ml) and cooled to −5° C. Cyclopentylmagnesium chloride (2.0M in diethyl ether, 20 ml, 40 mmol) was added dropwise over 5–10 minutes and the reaction was allowed to warm slowly to room temperature. Further cyclopentylmagnesium chloride (2.0M in diethyl ether, 5 ml, 10 mmol) was added. The reaction was quenched by the addition of saturated aqueous ammonium chloride solution. The mixture was partitioned between water and ethyl acetate. The organic layer was dried (MgSO$_4$) and concentrated in vacuo. The residue was purified by flash column chromatography on silica, eluting with 20–35% ethyl acetate/i-hexane, to give the title compound (1.74 g, 30%).

$\delta_H$ (400 MHz, CDCl$_3$): 8.50 (1H, d, J 2.3 Hz), 8.42 (1H, dd, J 1.6, 4.8 Hz), 7.55–7.52 (1H, m), 7.22–7.18 (1H, m), 3.02–2.96 (1H, m), 2.14–2.06 (2H, m), 1.86–1.79 (2H, m), 1.1.77–1.68 (2H, m), 1.64–1.54 (2H, m); m/z (ES+) 148 (M+H)$^+$.

Description 41

3-Cyclopentylpiperidine

Platinum oxide (0.2 g, 0.82 mmol) was added as a slurry in ethanol to a solution of 3-cyclopentylpyridine (1 g, 6.8 mmol) in ethanol (15 ml) and concentrated hydrochloric acid (1 ml). The mixture was hydrogenated in a Parr apparatus at 50 psi for 18 hours then filtered through Celite. The filtrate was concentrated in vacuo and the residue partitioned between 10% aqueous sodium carbonate solution and ethyl acetate. The organic layer was dried (MgSO$_4$) and concentrated in vacuo to give the title compound (0.87 g, 84%).

$\delta_H$ (400 MHz, CDCl$_3$): 3.09–3.06 (1H, m), 2.30–2.97 (1H, m), 2.52 (1H, dt, J 3, 12 Hz), 2.29–2.24 (1H, m), 1.88–1.83 (1H, m), 1.79–1.70 (2H, m), 1.66–1.53 (3H, m), 1.51–1.39 (4H, m), 1.20–0.99 (4H, m); m/z (ES$^+$) 153 (M+H)$^+$.

Description 42

1-(tert-Butoxycarbonyl)-3-formylpiperidine

Dimethylsulphoxide (1.35 ml, 18.8 mmol) was added dropwise to a solution of oxalyl chloride (1.65 ml, 18.8 mmol) in dichloromethane (20 ml) at −78° C. When the addition was complete, the reaction was stirred for a further 15 minutes at −78° C. 1-(tert-Butoxycarbonyl)-3-(hydroxymethyl)piperidine (2.7 g, 12.6 mmol) was added and the reaction warmed to −20° C. and stirred at this temperature for 20 minutes. Triethylamine (5.25 ml, 37.6 mmol) was added and the reaction allowed to warm to room temperature and stirred for 1 hour. The mixture was diluted with dichloromethane and washed with water (×2). The organic layer was dried (MgSO$_4$) and concentrated in vacuo. The residue was taken up in tetrahydrofuran and filtered through cotton wool. The filtrate was evaporated in vacuo to give the title compound (2.32 g, 89%).

$\delta_H$ (400 MHz, CDCl$_3$): 9.70 (1H, s), 3.95–3.90 (1H, m), 3.66–3.63 (1H, m), 3.35–3.30 (1H, m), 3.12–3.06 (1H, m), 2.44–2.40 (1H, m), 1.97–1.93 (1H, m), 1.72–1.63 (3H, m), 1.46 (9H, s); m/z (ES$^+$) 158 (M−tBu)$^+$.

Description 43

1-(tert-Butoxycarbonyl)-3-ethynylpiperidine

The product of Description 42 (2.3 g, 10.8 mmol), potassium carbonate (3.9 g, 28 mmol) and dimethyl (1-diazo-2-oxopropyl)phosphonate (5.2 g, 27 mmol) were combined in methanol (15 ml) and stirred at room temperature for 3 hours. The mixture was concentrated in vacuo and the residue partitioned between ethyl acetate and brine. The organic layer was dried (MgSO$_4$) and concentrated in vacuo. The residue was purified by flash column chromatography on silica, eluting with 2–5% ethyl acetate/i-hexane, to give the title compound (1.77 g, 79%).

$\delta_H$ (400 MHz, CDCl$_3$): 3.89–3.78 (1H, m), 3.68–3.63 (1H, m), 2.95–2.90 (2H, m), 2.39–2.34 (1H, m), 1.99 (1H, d, J 2.3 Hz), 1.93–1.88 (1H, m), 1.66–1.61 (1H, m), 1.55–1.49 (1H, m), 1.39 (9H, s), 1.39–1.33 (1H, m).

Description 44

3-Ethynylpiperidine 1-(tert-Butoxycarbonyl)-3-ethynylpiperidine (0.5 g, 2.4 mmol) was dissolved in 10% trifluoroacetic acid/dichloromethane (11 ml) and stirred at room temperature for 1 hour. The solvent was evaporated in vacuo to give the title compound as the trifluoroacetate salt (0.53 g, 100%).

$\delta_H$ (400 MHz, CDCl$_3$): 7.92–7.70 (1H, m), 3.43–3.40 (1H, m), 3.28–3.26 (1H, m), 3.18–3.11 (2H, m), 2.98–2.93 (1H, m), 2.27 (1H, d, J 2.4 Hz), 2.13–1.99 (2H, m), 1.90–1.74 (2H, m); m/z (ES+) 110 (M+H)$^+$.

Example 1

1-[3-(1-Benzenesulfonyl)cyclobutyl)propyl]-4-phenylpiperazine hydrochloride

A mixture of [1-(3-bromopropyl)cyclobutanesulfonyl] benzene (75 mg, 0.24 mmol), potassium carbonate (100 mg, 0.72 mmol), N-phenylpiperazine (0.1 ml, 0.62 mmol) and acetonitrile (1 ml) was stirred at 65° C. After completion, the mixture was purified on silica gel (dichloromethane:methanol) to give the title product (75 mg, 78%). The hydrochloride salt was prepared by treatment with ethereal HCl.

$\delta_H$ (360 MHz, MeOH-d$_4$): 7.93 (2H, m), 7.78 (1H, m), 7.67 (2H, t, J 7.9 Hz), 7.29 (2H, m), 7.04 (2H, d, J 7.9 Hz), 6.95 (1H, t, J 7.4 Hz), 3.85 (2H, br d, J 12.6 Hz), 3.68 (2H, br d, J 10.5 Hz), 3.34–3.00 (6H, m), 2.79 (2H, m), 2.17–1.75 (8H, m); m/z (ES$^+$) 399 (M+H)$^+$.

Example 2

1-[3-(1-Benzenesulphonylcyclopent-3-enyl)propyl]-4,5-dimethyl-1,2,3,6-tetrahydropyridine A solution of 3-(1-benzenesulphonylcyclopent-3-enyl) propan-1-ol (56 mg, 0.21 mmol) and triethylamine (41 μL, 0.29 mmol) in dichloromethane (5 ml) was cooled to 0° C. and treated with methanesulphonyl chloride (21 μL, 0.27 mmol). The mixture was allowed to warm to room temperature and stirred for 30 minutes, then diluted with water and extracted with ethyl acetate. The combined organic layers were dried (MgSO$_4$) and concentrated in vacuo. The residue was dissolved in acetonitrile (5 ml), treated with 3,4-dimethyl-1,2,5,6-tetrahydropyridine (397 mg, 0.32 mmol) and potassium carbonate (58 mg, 0.42 mmol) and heated at 60° C. for 3 hours. The mixture was diluted with water and extracted with ethyl acetate. The combined organic layers were dried (MgSO$_4$) and concentrated in vacuo. The residue was purified by preparative thin layer chromatography, eluting with 5% methanol/dichloromethane, to give the title compound.

$\delta_H$ (400 MHz, CDCl$_3$): 7.90–7.87 (2H, m), 7.67–7.63 (1H, m), 7.59–7.55 (2H, m), 3.87 (1H, br m), 3.00–2.25 (12H, m), 1.90–1.82 (1H, m), 1.62–1.56 (8H, m); m/z (ES$^+$) 360 (M+H)$^+$.

Compounds listed in the Table 1 were prepared by the method in Example 1 or Example 2 from appropriate chlorides, bromides and mesylates and relevant amines.

TABLE 1

| Example No. | Structure | m/z (ES⁺) (M,M + H)⁺ |
|---|---|---|
| 3 | 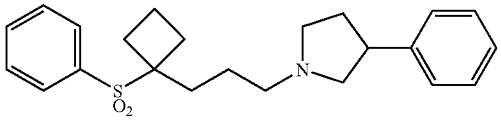 | 384 |
| 4 | 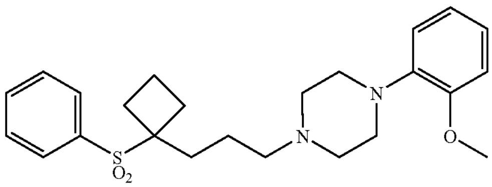 | 429 |
| 5 | 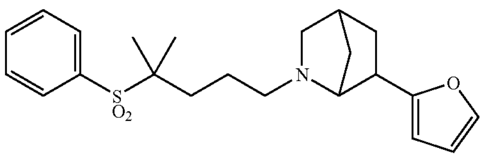 | 388 |
| 6 | 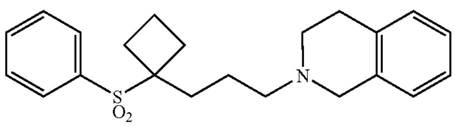 | 370 |
| 7 | 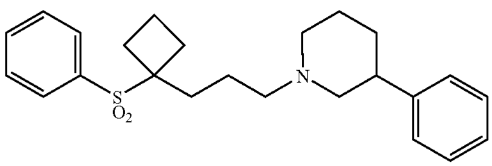 | 398 |
| 8 | 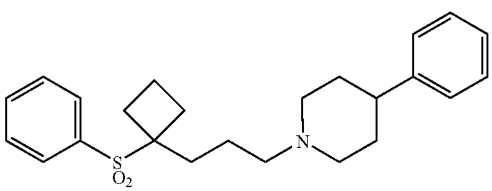 | 398 |
| 9 | 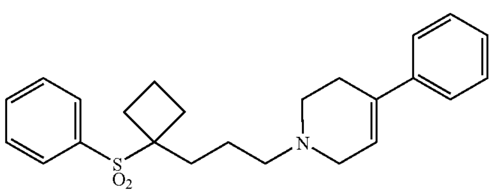 | 396 |
| 10 | 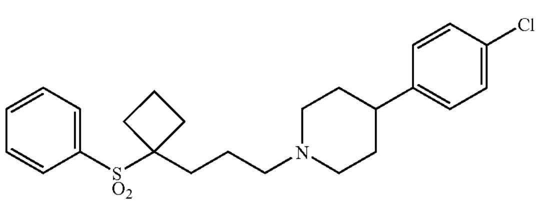 | 429,430,431 |
| 11 | 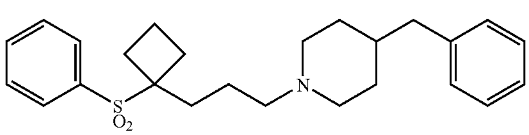 | 412 |

TABLE 1-continued

| Example No. | Structure | m/z (ES+) (M,M + H)+ |
|---|---|---|
| 12 | 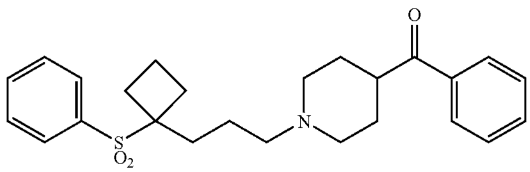 | 426 |
| 13 | 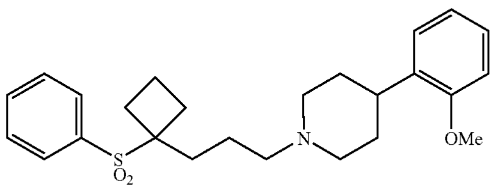 | 428 |
| 14 | 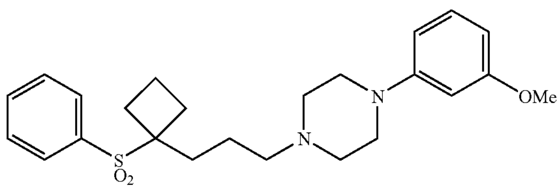 | 429 |
| 15 | 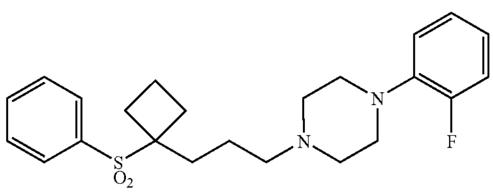 | 417 |
| 16 | 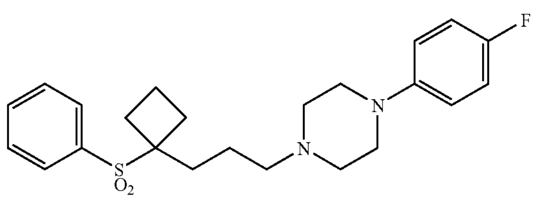 | 417 |
| 17 | 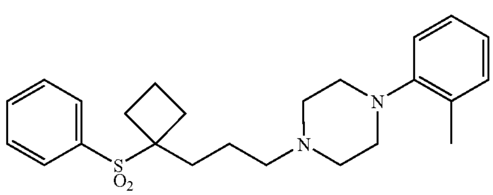 | 413 |
| 18 | 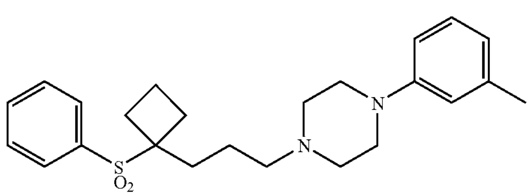 | 413 |
| 19 | 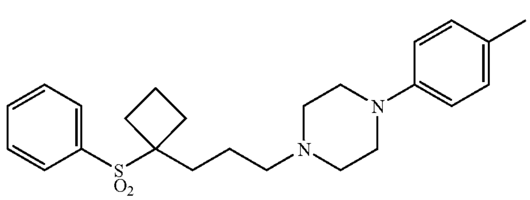 | 413 |

TABLE 1-continued

| Example No. | Structure | m/z (ES+) (M, M + H)+ |
|---|---|---|
| 20 | 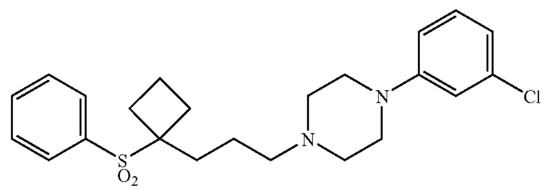 | 432, 433, 434, 435 |
| 21 | 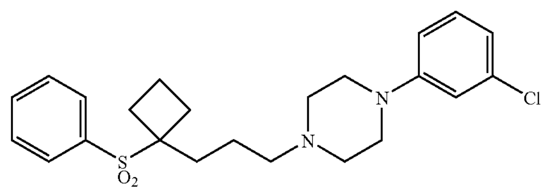 | 433, 434, 435 |
| 22 | 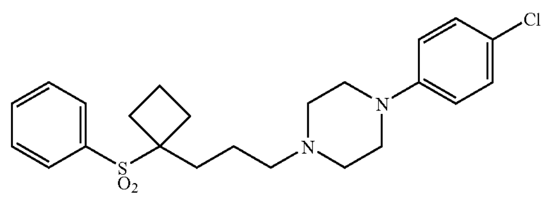 | 432, 433, 434, 435 |
| 23 | 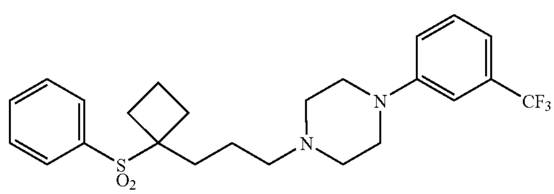 | 466, 467 |
| 24 | 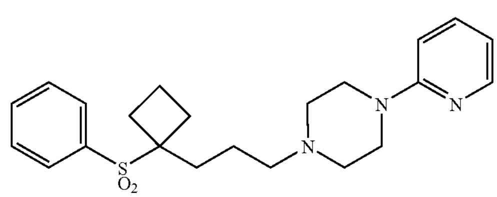 | 400 |
| 25 | 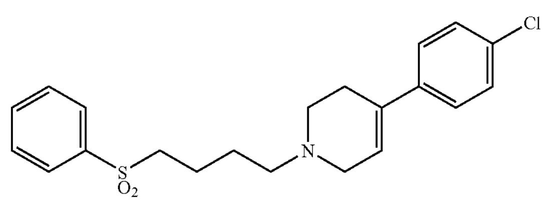 | 390 |
| 26 | 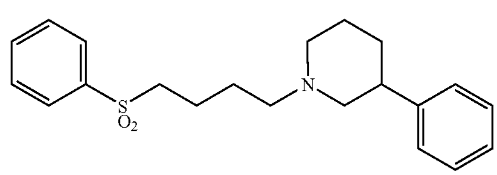 | 358 |
| 27 | 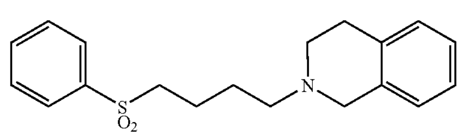 | 330 |

TABLE 1-continued
| Example No. | Structure | m/z (ES+) (M,M + H)+ |
|---|---|---|
| 28 | 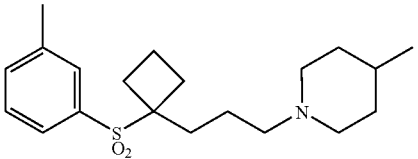 | 350 |
| 29 | 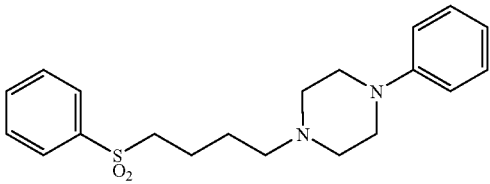 | 359 |
| 30 | 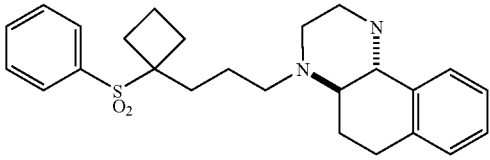 | 426 |
| 31 | 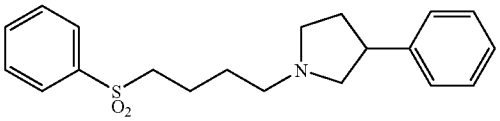 | 344 |
| 32 | 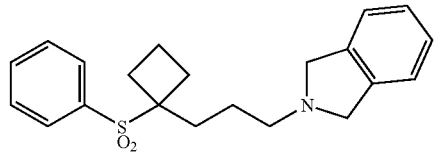 | 356 |
| 33 | 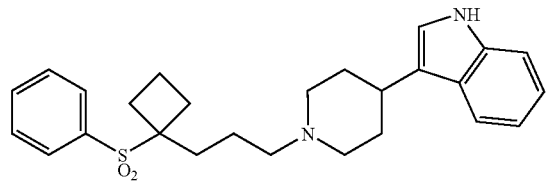 | 437 |
| 34 | 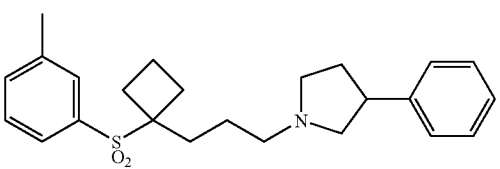 | 398 |
| 35 | 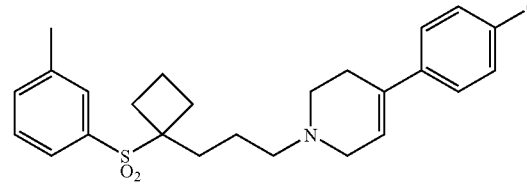 | 444,445,446 |

TABLE 1-continued
| Example No. | Structure | m/z (ES+) (M,M + H)+ |
|---|---|---|
| 36 | 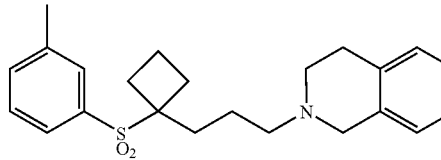 | 384 |
| 37 | 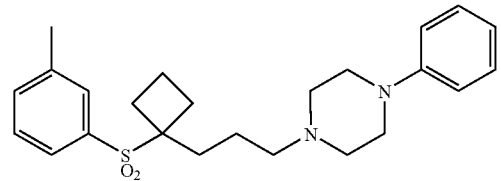 | 413 |
| 38 | 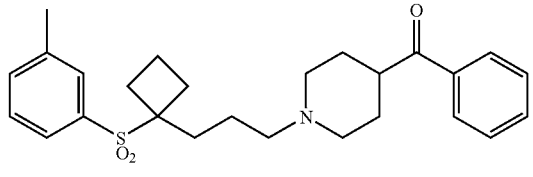 | 440 |
| 39 | 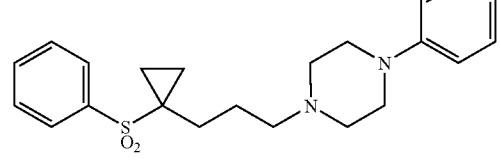 | 385 |
| 40 | 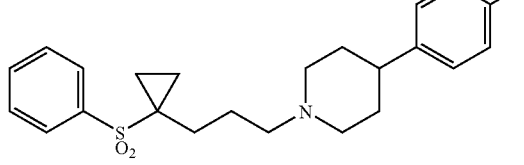 | 415,416,417 |
| 41 | 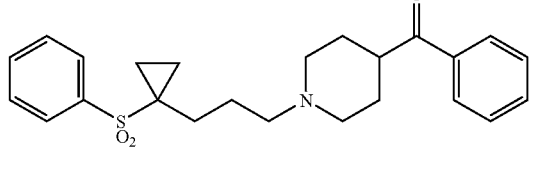 | 412 |
| 42 | 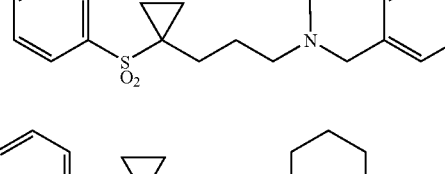 | 356 |
| 43 | 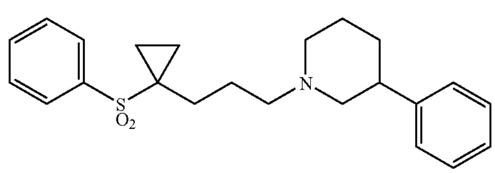 | 384 |

TABLE 1-continued
| Example No. | Structure | m/z (ES+) (M,M + H)+ |
|---|---|---|
| 44 | 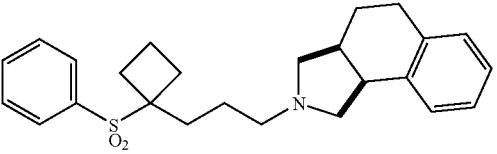 | 410 |
| 45 | 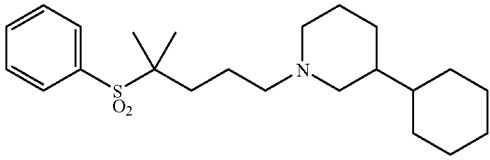 | 392 |
| 46 | 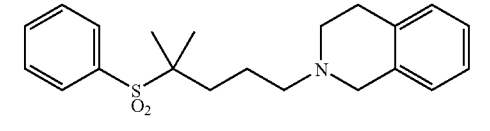 | 358 |
| 47 | 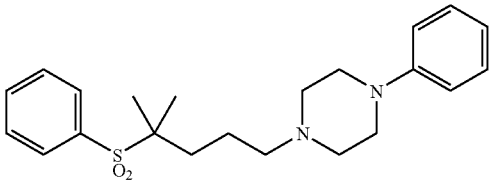 | 387 |
| 48 | 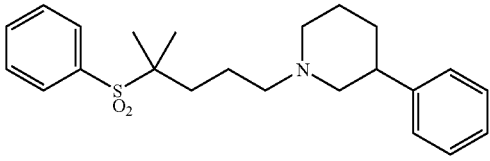 | 386 |
| 49 | 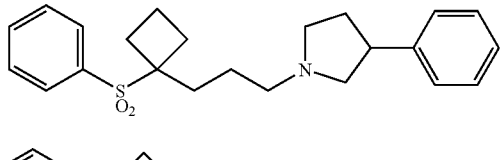 | 398 |
| 50 | 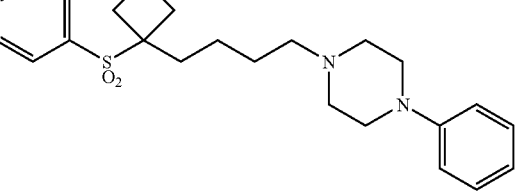 | 413 |
| 51 | 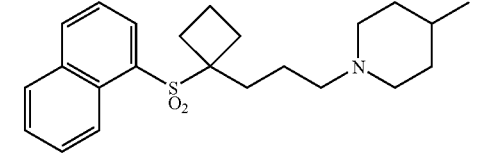 | 386 |
| 52 | 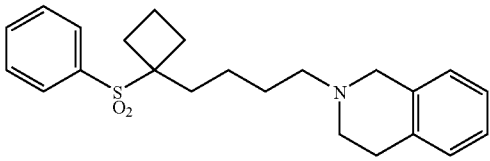 | 384 |

TABLE 1-continued

| Example No. | Structure | m/z (ES+) (M,M + H)+ |
|---|---|---|
| 53 | 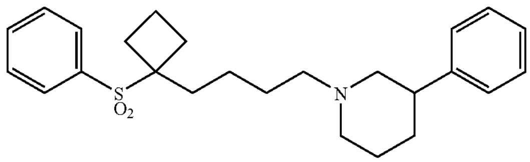 | 412 |
| 54 | 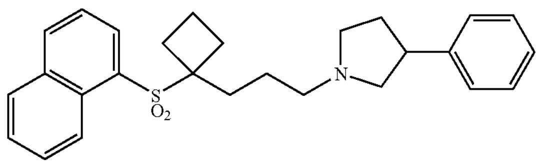 | 434 |
| 55 | 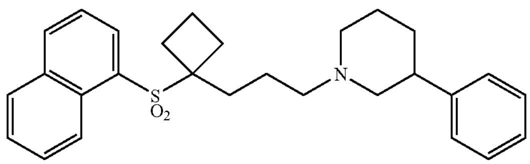 | 448 |
| 56 | 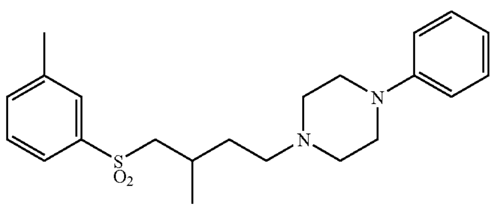 | 387 |
| 57 | 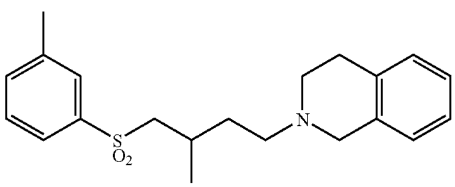 | 358 |
| 58 | 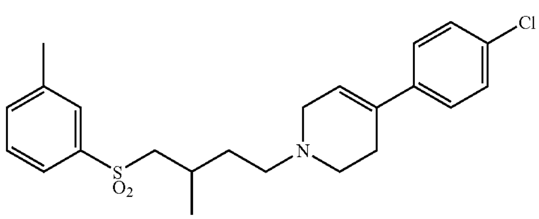 | 418,420 |
| 59 | 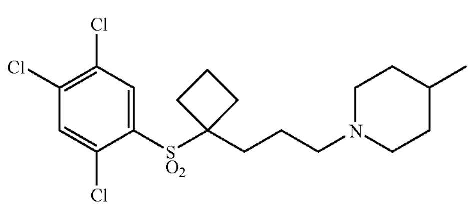 | 438,440,442 |
| 60 | 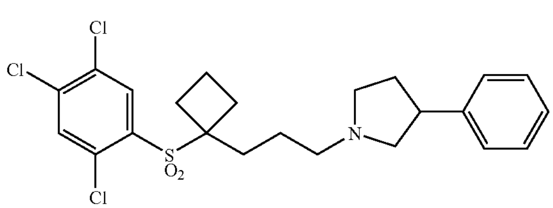 | 486,488,490 |

TABLE 1-continued

| Example No. | Structure | m/z (ES+) (M,M + H)+ |
|---|---|---|
| 61 | 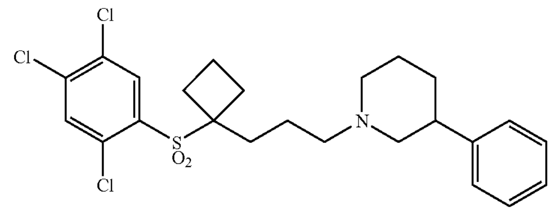 | 500,502,504 |
| 62 | 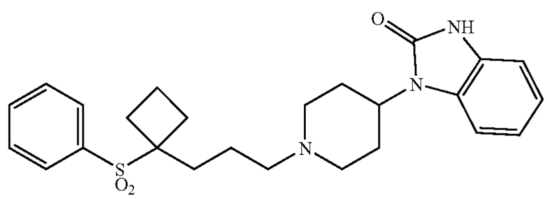 | 454 |
| 63 | 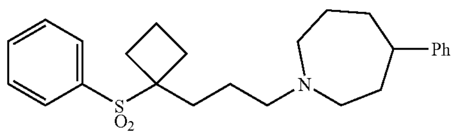 | 411 |
| 64 | | 411 |
| 65 | 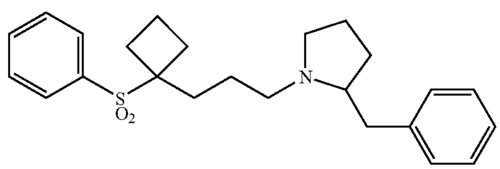 | 397 |
| 66 | 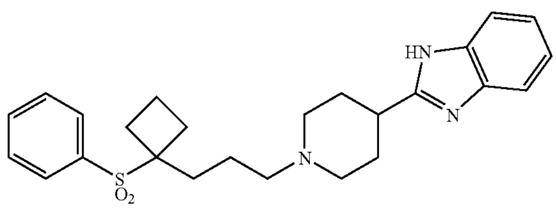 | 438 |
| 67 | 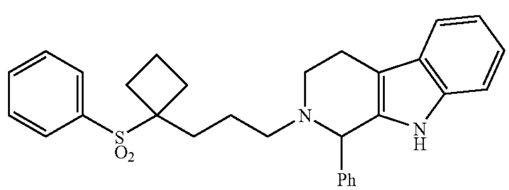 | 484 |
| 68 | 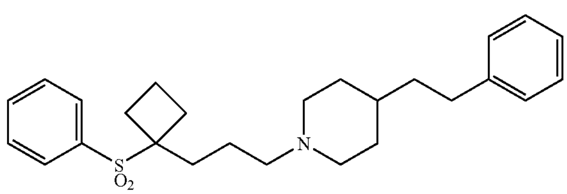 | 425 |
| 69 | 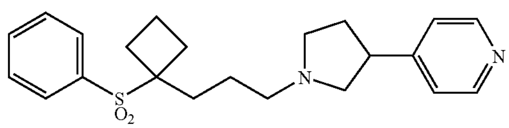 | 384 |

TABLE 1-continued

| Example No. | Structure | m/z (ES+) (M, M + H)+ |
|---|---|---|
| 70 | 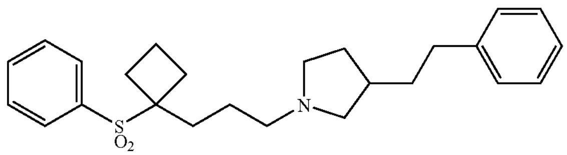 | 411 |
| 71 | 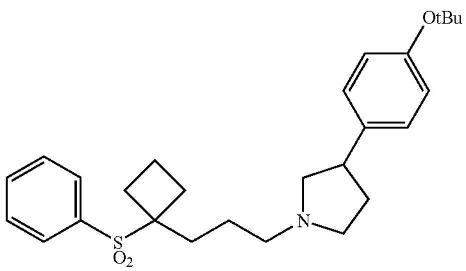 | 455 |
| 72 | 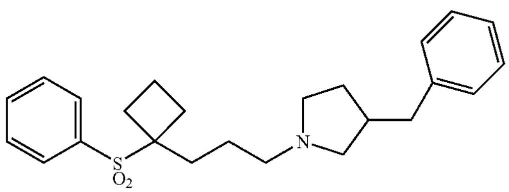 | 397 |
| 73 | 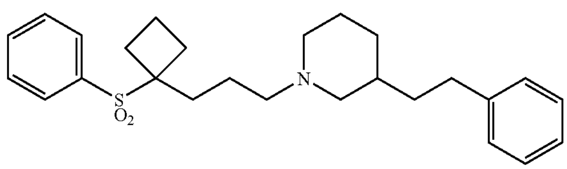 | 425 |
| 74 | 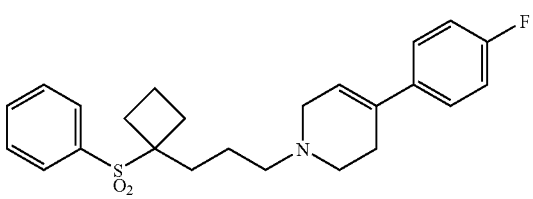 | 413 |
| 75 | 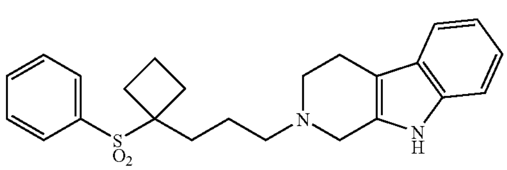 | 408 |
| 76 | 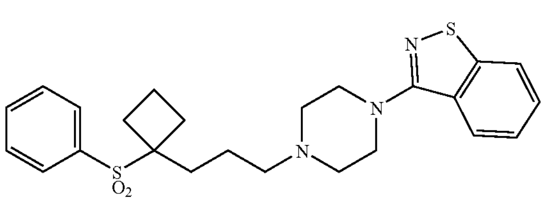 | 455 |

TABLE 1-continued

| Example No. | Structure | m/z (ES+) (M,M + H)+ |
|---|---|---|
| 77 | 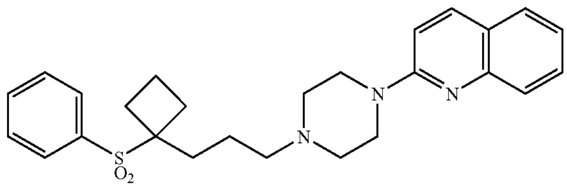 | 449 |
| 78 | 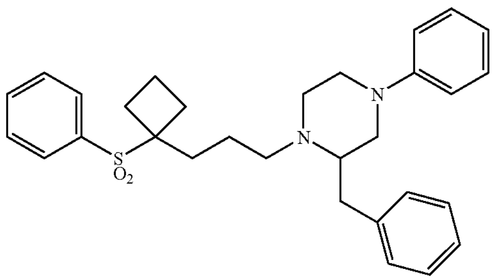 | 488 |
| 79 | 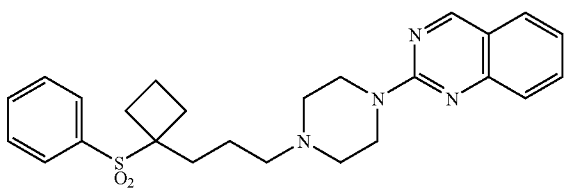 | 450 |
| 80 | 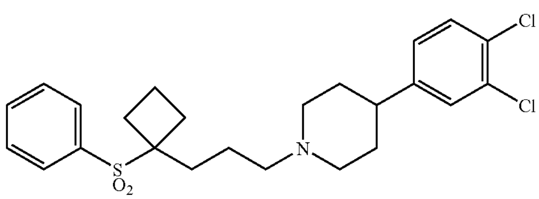 | 466 |
| 81 | 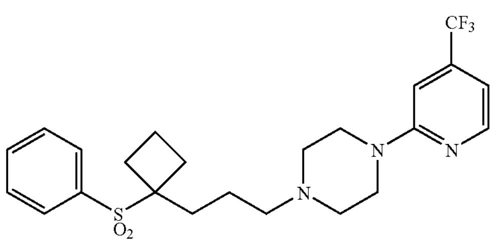 | 467 |
| 82 | 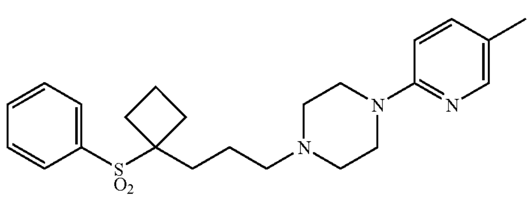 | 413 |
| 83 | 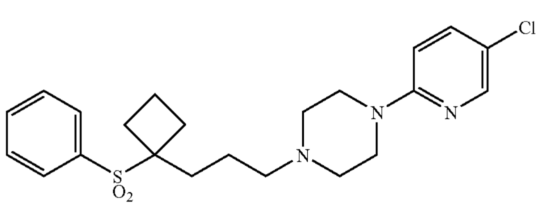 | 433 |

TABLE 1-continued

| Example No. | Structure | m/z (ES+) (M,M + H)+ |
|---|---|---|
| 84 | [structure: phenylsulfonyl-cyclobutyl-propyl-piperazine-(2,4-difluorophenyl)] | 434 |
| 85 | [structure: phenylsulfonyl-cyclobutyl-propyl-piperazine-(2-cyanophenyl)] | 423 |
| 86 | [structure: phenylsulfonyl-cyclobutyl-propyl-piperazine-(6-chloropyridin-2-yl)] | 433 |
| 87 | [structure: phenylsulfonyl-cyclobutyl-propyl-piperazine-(2-nitrophenyl)] | 443 |
| 88 | [structure: phenylsulfonyl-cyclobutyl-propyl-piperazine-(4-chloropyridin-2-yl)] | 433 |
| 89 | [structure: phenylsulfonyl-cyclobutyl-propyl-piperidine-fluorenylidene] | 509 |
| 90 | [structure: phenylsulfonyl-cyclobutyl-propyl-(7-methoxy-tetrahydroisoquinoline)] | 399 |

TABLE 1-continued
| Example No. | Structure | m/z (ES+) (M,M + H)+ |
|---|---|---|
| 91 | 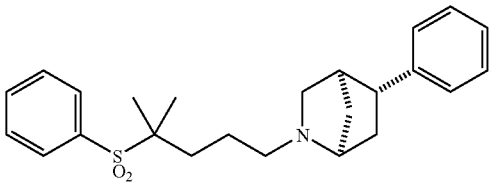 | 398 |
| 92 | 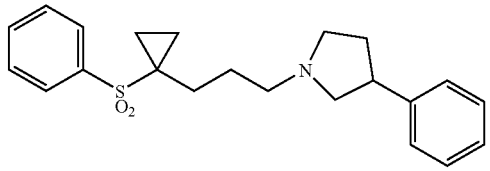 | 370 |
| 93 | | 370 |
| 94 | 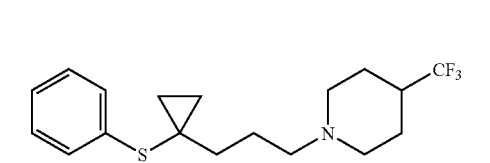 | 376 |
| 95 | 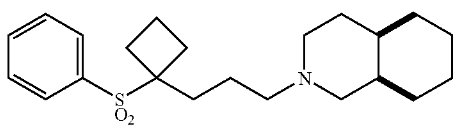 | 376 |
| 96 | 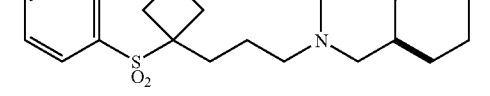 | 376 |
| 97 | 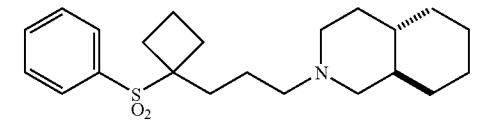 | 389 |
| 98 | 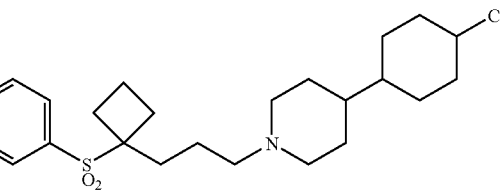 | 337 |
| 99 | 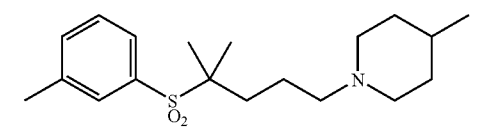 | 371 |
| 100 | 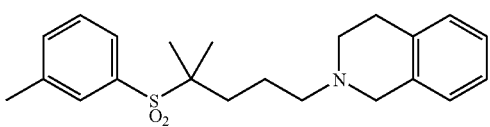 | 399 |

TABLE 1-continued

| Example No. | Structure | m/z (ES+) (M,M + H)+ |
|---|---|---|
| 101 | 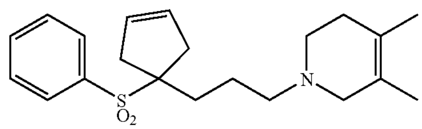 | 360 |
| 102 | 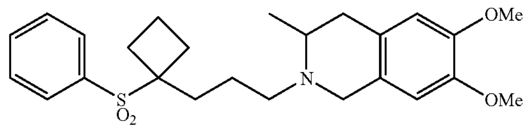 | 443 |
| 103 | 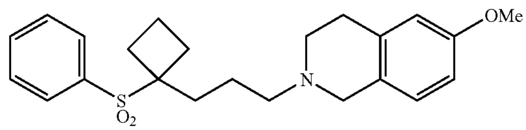 | 399 |
| 104 | 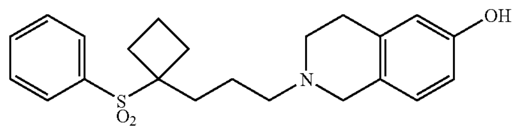 | 385 |
| 105 | 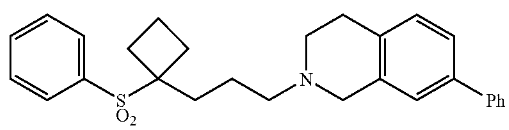 | 445 |
| 106 | 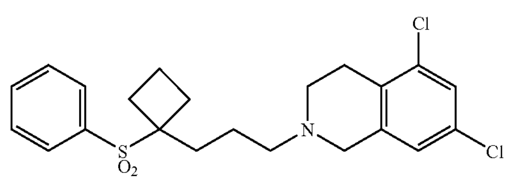 | 437 |
| 107 | 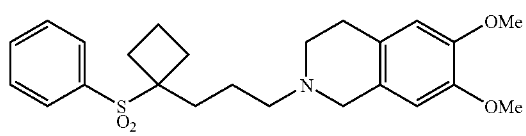 | 429 |
| 108 | 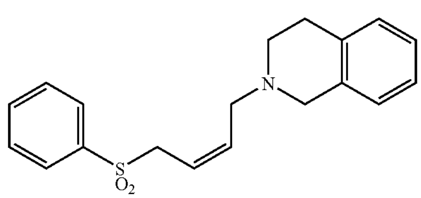 | 328 |
| 109 | 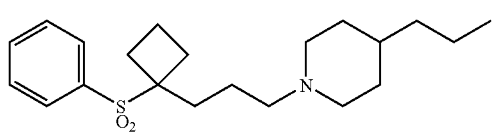 | 363 |
| 110 | 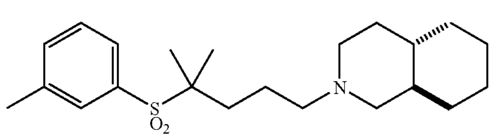 | 378 |

TABLE 1-continued
| Example No. | Structure | m/z (ES⁺) (M,M + H)⁺ |
|---|---|---|
| 111 | 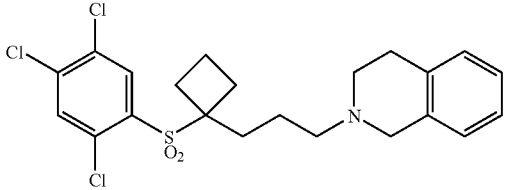 | 472,474,476 |
| 112 | 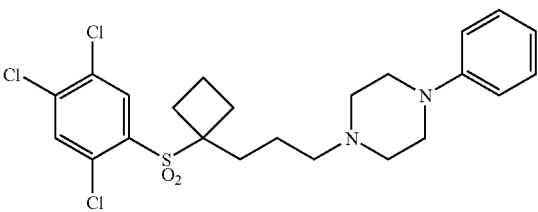 | 501,503,505 |
| 113 | 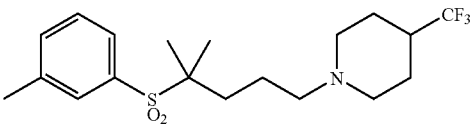 | 392 |
| 114 | 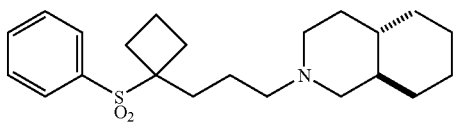<br>chiral | 376 |
| 115 | 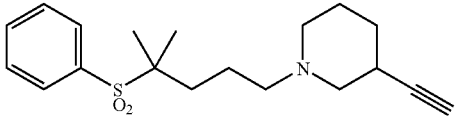 | 334 |
| 116 | 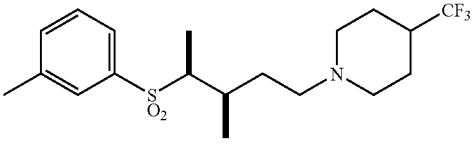 | 392 |
| 117 | | 378 |
| 118 | 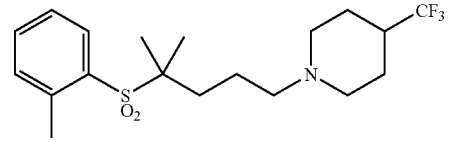 | 392 |
| 119 | 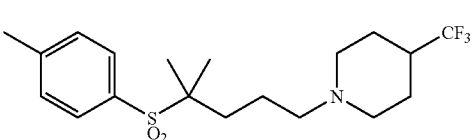 | 392 |
| 120 | 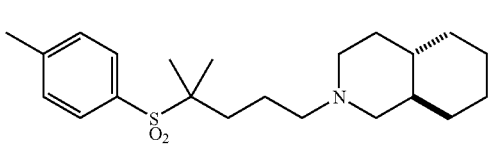 | 378 |

TABLE 1-continued

| Example No. | Structure | m/z (ES+) (M,M + H)+ |
|---|---|---|
| 121 | 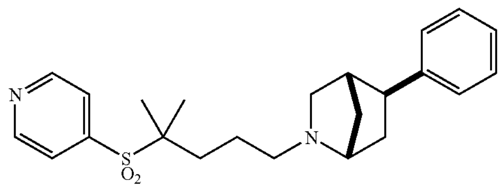 | 399 |
| 122 | 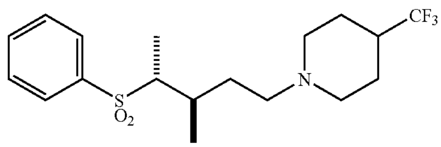 | 378 |
| 123 | 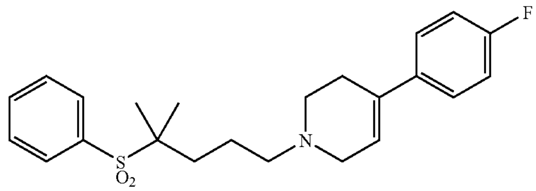 | 402 |
| 124 | 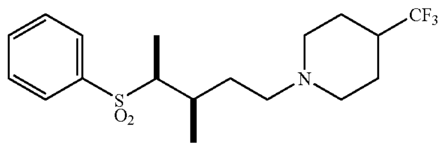 | 378 |
| 125 | | 392 |
| 126 | 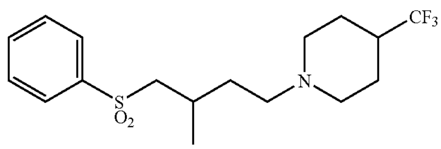 | 364 |
| 127 | 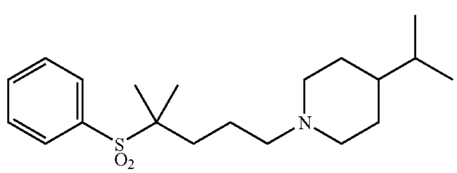 | 352 |
| 128 | 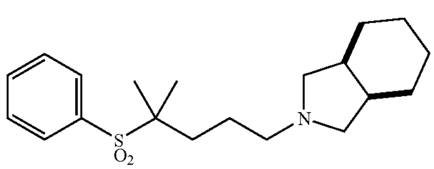 | 350 |
| 129 | 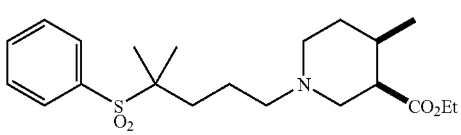 | 396 |
| 130 | 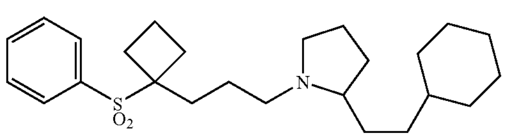 | 418 |

TABLE 1-continued

| Example No. | Structure | m/z (ES+) (M,M + H)+ |
|---|---|---|
| 131 | 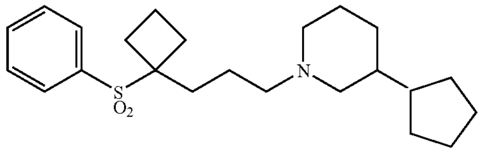 | 390 |
| 132 | 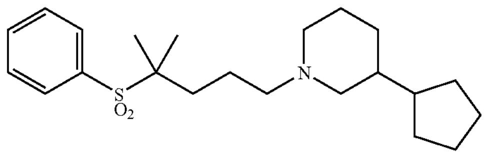 | 378 |
| 133 | 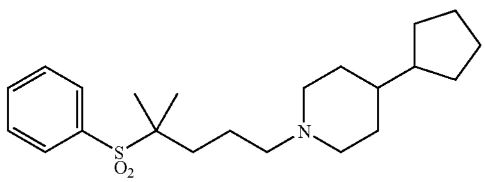 | 378 |
| 134 | 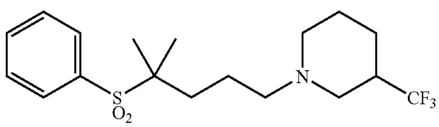 | 378 |
| 135 | 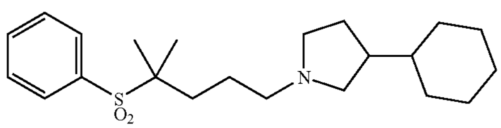 | 390 |
| 136 | 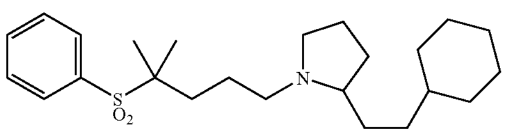 | 406 |
| 137 | 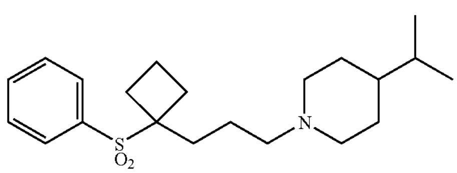 | 364 |
| 138 | 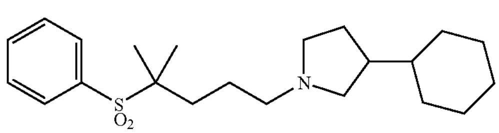 | 378 |
| 139 | 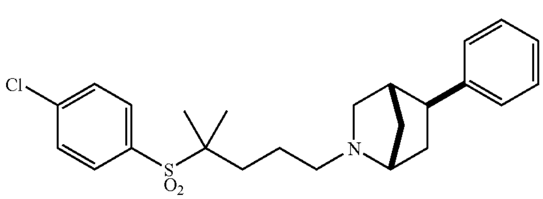 | 432,434 |

TABLE 1-continued

| Example No. | Structure | m/z (ES+) (M,M + H)+ |
|---|---|---|
| 140 | 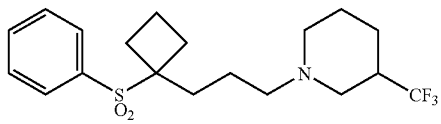 | 390 |
| 141 | 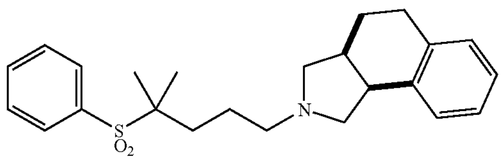 | 398 |
| 142 | 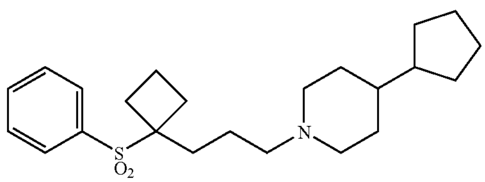 | 390 |
| 143 | 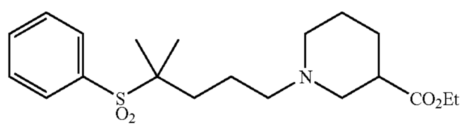 | 382 |
| 144 | 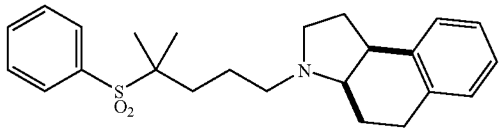 | 398 |
| 145 | 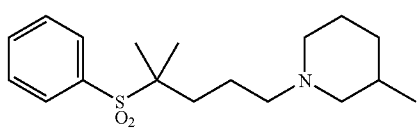 | 324 |
| 146 | 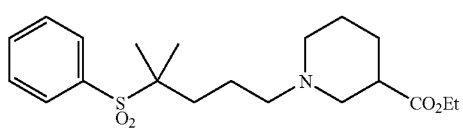 | 382 |
| 147 | 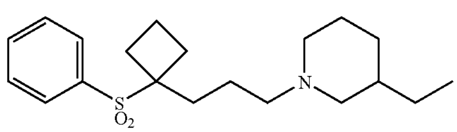 | 350 |
| 148 | 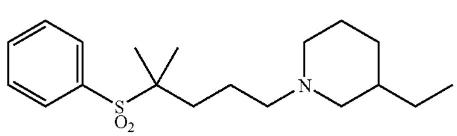 | 338 |
| 149 | 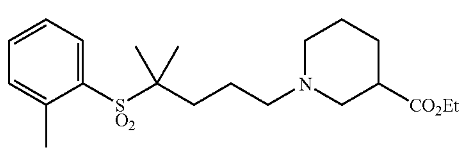 | 396 |

TABLE 1-continued

| Example No. | Structure | m/z (ES+) (M,M + H)+ |
|---|---|---|
| 150 | 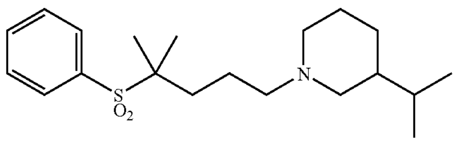 | 351 |
| 151 | 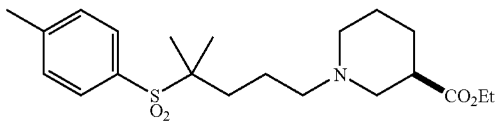 | 396 |
| 152 | 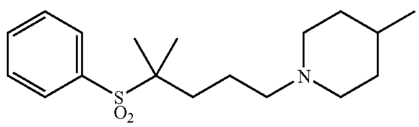 | 324 |
| 153 | 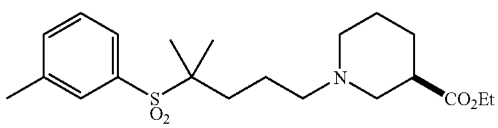 | 396 |
| 154 | 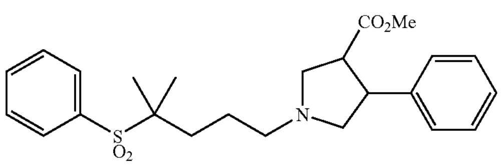 | 430 |
| 155 | 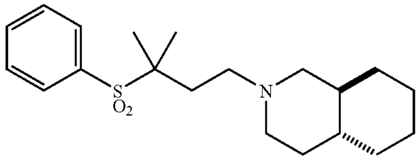 | 350 |
| 156 | 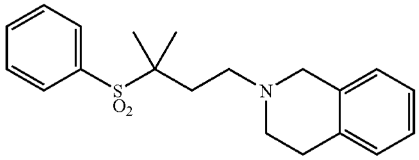 | 344 |
| 157 | 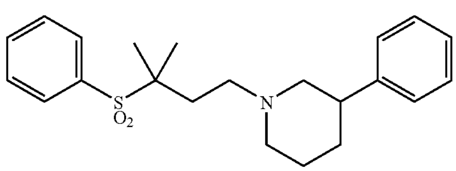 | 372 |
| 158 | 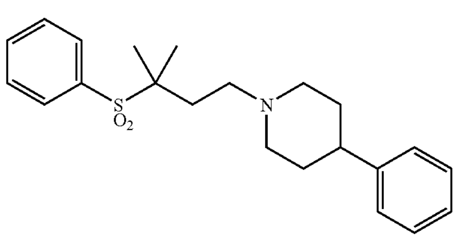 | 372 |

TABLE 1-continued

| Example No. | Structure | m/z (ES⁺) (M,M + H)⁺ |
|---|---|---|
| 159 | 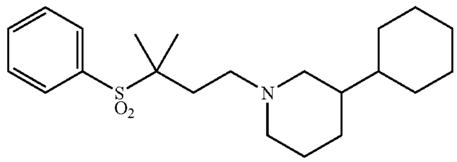 | 378 |
| 160 | 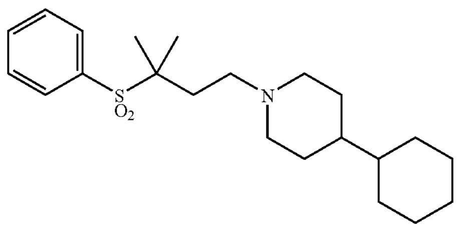 | 378 |
| 161 | 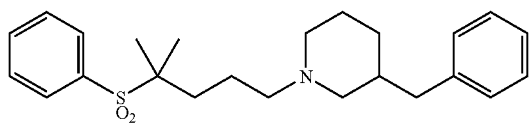 | 400 |
| 162 | 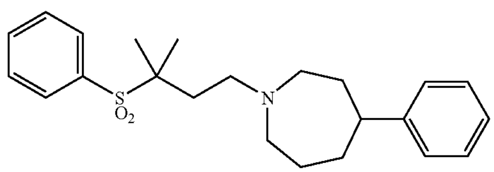 | 386 |
| 163 | 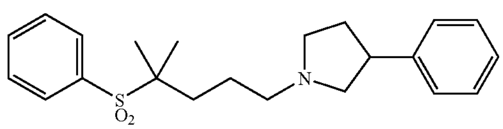 | 372 |
| 164 | 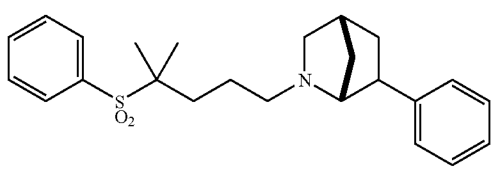 | |
| 165 | 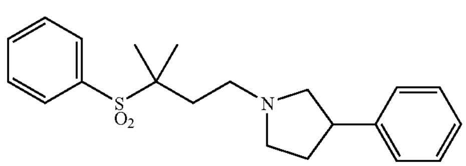 | 358 |
| 166 | 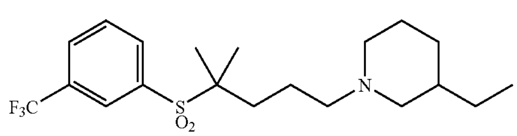 | 406 |
| 167 | 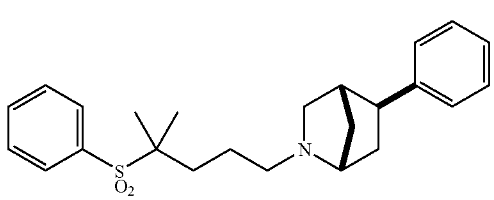 | 398 |

TABLE 1-continued

| Example No. | Structure | m/z (ES+) (M, M + H)+ |
|---|---|---|
| 168 | 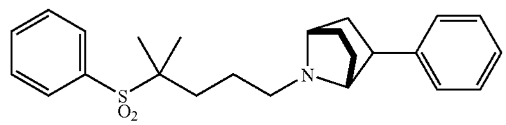 | 398 |
| 169 | 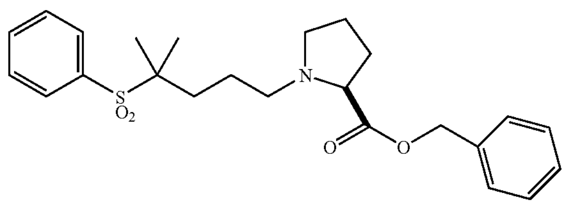 | 430 |
| 170 | 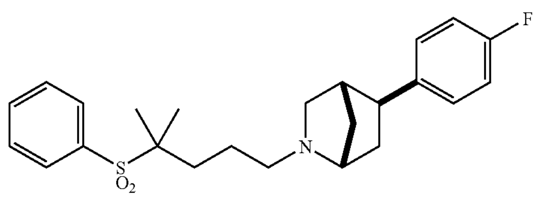 | 416 |
| 171 | 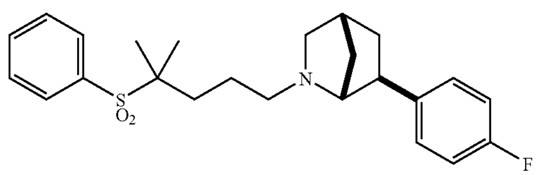 | 416 |
| 172 | 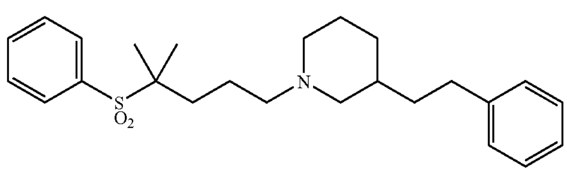 | 414 |
| 173 | 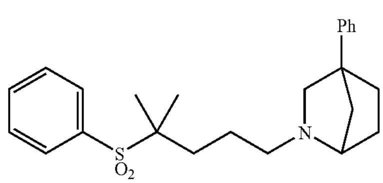 | 398 |
| 174 | 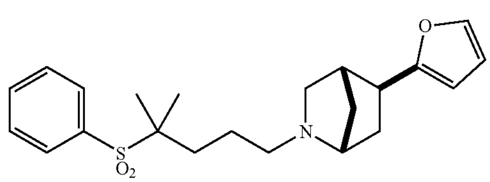 | 388 |
| 175 | 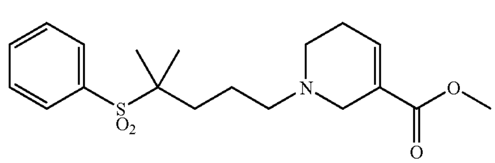 | 366 |

TABLE 1-continued

| Example No. | Structure | m/z (ES+) (M,M + H)+ |
|---|---|---|
| 176 | 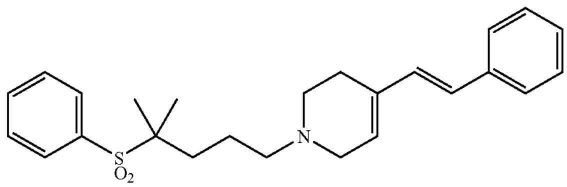 | 416 |

Description 45

6-exo-Hydroxy-2-[4-methyl-4-(phenylsulfonyl)pentyl]-2-azabicyclo[2.2.1]heptane 6-Hydroxy-2-azabicyclo[2.2.1]heptane (2.1 g, 14 mmol), (5-bromo-2-methylpentane-2-sulphonyl)benzene (5.56 g, 18 mmol) and sodium bicarbonate (7.0 g, 83 mmol) in acetonitrile (70 ml) were heated at 60° C. for 2 hours. The reaction mixture was diluted with dichloromethane (100 ml) and filtered to remove inorganic material. The solvent was concentrated in vacuo, the residue was dispersed between water and ethyl acetate. The combined organic extracts were washed with brine, dried (MgSO$_4$) and evaporated in vacuo. The residue was purified by column chromatography on alumina (grade III), using a gradient elution of 10–100% ethyl acetate in i-hexane, to give the product (4 g, 85%).

$\delta_H$ (400 MHz, CDCl$_3$): 7.88 (2H, dd, J 1.0, 8.4 Hz), 7.67–7.63 (1H, m), 7.57–7.53 (2H, m), 3.99 (1H, d, J 6.7 Hz), 2.99 (1H, s), 2.35–2.54 (4H, m), 2.21 (1H, d, J 8.6 Hz), 1.79–1.70 (3H, m), 1.53 (2H, d, J 9.0 Hz), 1.50–1.44 (3H, m), 1.33 (1H, q, J 2.2 Hz), 1.29 (6H, s); m/z (ES+) 338 (MH+).

Example 177

6-Cyano-2-[4-methyl-4-(phenylsulfonyl)pentyl]-2-azabicyclo[2.2.1]heptane

6-Hydroxy-2-[4-methyl-4-(phenylsulfonyl)pentyl]-2-azabicyclo[2.2.1]heptane (1 g, 2.97 mmol), potassium cyanide (386 mg, 6 mmol) and 18-crown-6 (78 mg, cat.) were suspended in acetonitrile and the mixture was cooled in ice-water. Tri-n-butylphosphine (1.2 ml, 5 mmol) was added followed by dropwise addition of carbon tetrachloride (0.57 ml, 6 mmol). The mixture was allowed to stir at room temperature for 12 h. The combined organic extracts were washed with brine, dried (MgSO$_4$) and evaporated in vacuo. The residue was purified by column chromatography on silica using a gradient elution of 10–100% ethyl acetate in i-hexane, to give the product (600 mg, 58%) as an oil which crystallised on standing.

$\delta_H$ (400 MHz, CDCl$_3$): 7.88–7.86 (2H, m), 7.68–7.64 (1H, m), 7.58–7.54 (2H, m), 3.44 (1H, s), 2.79–2.76 (2H, m), 2.47–2.35 (3H, m), 2.14 (1H, d, J 9.0 Hz), 1.86–1.71 (5H, m), 1.65 (1H, d), 1.51–1.43 (2H, m), 1.28 (6H, s); m/z (ES+) 347 (MH+).

Description 46

2-(1-Benzenesulfanyl)cyclopropyloxyethanol

Silver(I) tetrafluoroborate (975 mg, 5 mmol) was added to a suspension of ethane-1,2-diol (1.24 g, 20 mmol) and 1-iodo-1-phenylthiocyclopropane (1.61 g, 4.7 mmol) in toluene (15 ml) and tetrahydrofuran (10 ml) and the mixture stirred for 4 hours before being filtered. The residue remaining on concentration of the filtrate was dissolved in ethyl acetate (30 ml) and the solution washed with water (10 ml) and brine (10 ml), dried (MgSO$_4$), concentrated, and the residue subjected to chromatography over silica gel (2:1 i-hexane/ethyl acetate) to afford the product as a colourless oil (602 mg, 67%).

$\delta_H$ (360 MHz, CDCl$_3$): 7.50 (2H, m), 7.30 (2H, m), 7.21 (1H, m), 3.84–3.76 (2H, m), 3.75–3.66 (2H, m), 1.72 (1H, br t, J 5.6 Hz), 1.26 (2H, m), 1.11 (2H, m).

Description 47

2-(1-Benzenesulfonyl)cyclopropyloxyethanol

To a cooled (ice-bath) solution of the product of Description 46 (600 mg, 3.1 mmol) in methanol (15 ml) was added Oxone™ in water (30 ml) and the resulting suspension stirred for 1 h before removing the cooling bath and resuming stirring for a further 2.5 h. Following addition of water (20 ml), the mixture was extracted with ethyl acetate (3×10 ml), the combined extracts washed with brine (20 ml), dried (MgSO$_4$), and evaporated to leave the product as a gum (636 mg, 91%), which was used without further purification.

$\delta_H$ (360 MHz, CDCl$_3$): 7.95 (2H, m), 7.68 (1H, m), 7.58 (2H, m), 4.03 (2H, m, J 4.2 Hz), 3.71 (2H, t, J 4.2 Hz), 1.83 (1H, br), 1.68 (2H, m), 1.26 (2H, m).

Description 48

2-(1-Benzenesulfonyl)cyclopropyloxyacetaldehyde

Oxalyl chloride (444 mg, 3.5 mmol) was added to a stirred solution of DMSO (312 mg, 4 mmmol) in dichloromethane (30 ml) with cooling from a dry ice/acetone bath, followed after 10 min by a solution of 2-(1-benzenesulfonyl)cyclopropyloxyethanol (625 mg, 2.8 mmol) in dichloromethane (5 ml). The resulting thick suspension was stirred a further 15 min prior to adding triethylamine (505 mg, 5 mmol), removing the cooling bath and stirring a further 1 h. The solution was then washed sequentially with water (15 ml), 10% aqueous citric acid (15 ml), saturated aqueous sodium hydrogen carbonate (15 ml), and brine (15 ml), before being dried (MgSO$_4$), and evaporated to leave the product as a gum (585 mg), which was used without further purification.

Example 178

2-[2-(1-Benzenesulfonylcyclopropoxy)ethyl]-1,2,3, 4-tetrahydroisoquinoline

To a solution of the product of Description 48 (105 mg, 0.47 mmol) in dichloromethane (4 ml) was added 1,2,3,4-tetrahydroisoquinoline (73 mg, 0.55 mmol) and acetic acid (0.06 ml), followed after 5 min by sodium triacetoxyborohydride (148 mg, 0.7 mmol). After 0.75 h, the reaction mixture was diluted with dichloromethane (15 ml) and washed with saturated aqueous sodium carbonate (10 ml) and brine (10 ml), before being dried (MgSO$_4$), and evaporated. The residue was chromatographed over silica gel (3:2 i-hexane/ethyl acetate) to give the product as a colourless gum (91 mg), which was converted to the hydrochloride salt and recrystallised (MeOH/Et$_2$O) to leave a white solid.

$\delta_H$ (400 MHz, MeOH-d$_4$): 7.98 (2H, m), 7.75 (1H, m), 7.41 (2H, m), 7.35–7.22 (3H, m), 7.13 (1H, d, J 7.0 Hz), 4.36 (2H, m, J 4.2 Hz), 3.49 (2H, t, J 4.4 Hz), 3.13 (2H, m, J 5.9 Hz), 1.69 (2H, m), 1.46 (2H, m); m/z (ES$^+$) 358 (M+H)$^+$.

Example 179

2-[2-(1-Benzenesulfonylcyclopropoxy)ethyl]-decahydroisoquinoline

The title compound was prepared by the method in Example 178 from product of Description 48 and perhydroisoquinoline.

$\delta_H$ (400 MHz, MeOH-d$_4$): 7.98 (2H, m), 7.78 (1H, m), 7.67 (2H, m), 4.26 (2H, t, J 5.0 Hz), 3.45 (1H, m), 2.91 (1H, m), 2.61 (1H, t, J 11.7 Hz), 1.87–0.91 (18H, m); m/z (ES$^+$) 364 (M+H)$^+$.

Description 49

2-(1-Benzenesulphonylcyclopropylmethyl)oxirane

A solution of cyclopropanesulphonylbenzene (2.32 g, 12.75 mmol) in tetrahydrofuran (5 ml) was treated with n-butyllithium (1.6M in hexanes, 9.6 ml, 15.3 mmol) at −78° C. and stirred for 10 minutes. Epichlorohydrin (2.0 ml, 25.5 mmol) was added in one portion and the mixture allowed to warm to room temperature then diluted with water and extracted with ethyl acetate. The combined organic layers were dried (MgSO$_4$) and concentrated in vacuo to give the epoxide as an oil.

$\delta_H$ (400 MHz, CDCl$_3$): 7.91–7.88 (2H, m), 7.69–7.64 (1H, m), 7.60–7.56 (2H, m), 2.99–2.94 (1H, m), 2.70–2.68 (1H, m), 2.36–2.34 (1H, m), 2.08 (1H, dd, J 4.6, 15.5 Hz), 1.74–1.60 (3H, m), 1.21–1.16 (1H, m), 1.03–0.98 (1H, m).

Example 180

1-(1-Benzenesulphonylcyclopropyl)-3-(4,5-dimethyl-3,6-dihydro-2H-pyridin-1-yl)propan-2-ol Crude 2-(1-benzenesulphonylcyclopropylmethyl)oxirane (500 mg, 2.1 mmol), potassium carbonate (580 mg, 4.2 mmol) and 3,4-dimethyl-1,2,5,6-tetrahydropyridine (470 mg, 4.2 mmol) in acetonitrile (3 ml) were heated at 60° C. for 18 hours. The mixture was purified by preparative thin layer chromatography, eluting with 5% methanol/dichloromethane, to give the title compound.

$\delta_H$ (400 MHz, CDCl$_3$): 7.90–7.87 (2H, m), 7.67–7.63 (1H, m), 7.59–7.55 (2H, m), 3.87 (1H, br m), 3.00–2.25 (12H, m), 1.90–1.82 (1H, m), 1.62–1.56 (8H, m); m/z (ES$^+$) 350 (M+H)$^+$.

Description 50

4-Benzenesulfonyl-3,3-dimethylbutyraldehyde

Ozone was passed through a solution of product of Description 25 (0.75 g, 3.13 mmol) in dichloromethane (20 ml) until the blue colour persisted. Methanol (2 ml) was added followed by dimethyl sulphide (2.5 ml). The mixture was warmed to room temperature and left overnight then concentrated in vacuo to give the crude title product that was used in the next step without purification.

Example 181

1-(4-Benzenesulfonyl-3,3-dimethylbutyl)-4-trifluoromethylpiperidine

Sodium cyanoborohydride (78 mg, 1.2 mmol) was added to a stirred solution of the crude 4-benzenesulfonyl-3,3-dimethyl-butyraldehyde (240 mg, 1 mmol) and 4-trifluoromethylpiperidine (321 mg, 2.1 mmol) in methanol (4 ml). The mixture was stirred for 1 hour, quenched with sat. aqueous NaHCO$_3$ and extracted into dichloromethane. The combined organic extracts were dried (Na$_2$SO$_4$) and concentrated. The residue was purified on silica (dichloromethane:methanol) to give the title product.

$\delta_H$ (360 MHz, CDCl$_3$): 7.91 (2H, m), 7.64 (1H, m), 7.56 (2H, m), 3.11 (2H, s), 3.00 (2H, br d, J 11.9 Hz), 2.38 (2H, m), 2.07 (5H, m), 1.72 (2H, m), 1.66–1.50 (2H, m), 1.20 (6H, s); m/z (ES$^+$) 378 (M+H)$^+$.

Example 182

1-(4-Benzenesulfonyl-3,3-dimethylpentyl)-4-trifluoromethylpiperidine hydrochloride A solution of n-butyllithium (1.5M, 0.13 ml, 0.2 mmol) in hexanes was added to a stirred solution of 1-(4-benzenesulfonyl-3,3-dimethyl-butyl)-4-trifluoromethylpiperidine (40 mg, 0.11 mmol) in tetrahydrofuran (2 ml) at −78° C. The mixture was stirred for 30 min. and methyl iodide (0.34 ml) was added. After 1 hour, the reaction mixture was quenched with one drop of water and concentrated in vacuo. The residue was purified on silica gel (dichloromethane:methanol) to give 1-(4-benzenesulfonyl-3,3-dimethyl-pentyl)-4-trifluoromethyl-piperidine. The title product was prepared by treatment of the amine with 1M ethereal HCl.

$\delta_H$ (360 MHz, MeOH-d$_4$): 7.92 (2H, m), 7.74 (1H, m), 7.48 (2H, m), 3.11 (2H, s), 3.00 (2H, br d, J 11.9 Hz), 2.38 (2H, m), 2.07 (5H, m), 1.72 (2H, m), 1.66–1.50 (2H, m), 1.20 (6H, s); m/z (ES$^+$) 392 (M+H)$^+$.

Description 51

2-Benzenesulfonyl-5-bromo-2-methyl-pentanoic acid methyl ester

A solution of lithium bis(trimethylsilyl)amide in tetrahydrofuran (1M, 6.6 ml, 6.6 mmol) was added dropwise to a stirred solution of 2-benzenesulfonylpropionic acid methyl ester (1.38 g, 5.7 mmol) in tetrahydrofuran at −78° C. The mixture was stirred for 30 min. and 1,3-dibromopropane (3.17 ml, 31.2 mmol) was added. The mixture was slowly warmed to room temperature and stirred for 4 days. After quenching with satd. aqueous NH$_4$Cl, the mixture was extracted into dichloromethane. The combined organic extracts were dried (Na$_2$SO$_4$) and concentrated. The residue was purified on silica gel (i-hexane-ethyl acetate 5–20%) to give the title product (330 mg, 15%).

$\delta_H$ (360 MHz, CDCl$_3$): 7.84 (2H, m), 7.69 (1H, m), 7.57 (2H, m), 3.69 (3H, s), 3.43–3.00 (2H, m), 2.32 (1H, dt, J 4.3 and 12.9 Hz), 2.06 (1H, dt, J 4.7 and 12.1 Hz), 1.95 (1H, m), 1.74 (1H, m), 1.59 (3H, s).

Example 183 and 184

2-Benzenesulfonyl-5-(4,5-dimethyl-3,6-dihydro-2H-pyridin-1-yl)-2-methylpentanoic acid methyl ester hydrochloride (example 183) and 1-(4-benzenesulfonylpentyl)-4,5-dimethyl-1,2,3,6-tetrahydropyridine hydrochloride (example 184)

A mixture of product of the Description 51 and 3,4-lutidine (1 ml) was stirred at 100° C. for 30 min. 3,4-lutidine was removed under reduced pressure. The residue was treated with methanol (10 ml). Solid sodium borohydride (180 mg, 4.68 mmol) was added. After completion, the reaction was quenched with sat. aqueous NaHCO$_3$ and extracted into dichloromethane. The combined organic extracts were dried (Na$_2$SO$_4$) and concentrated. The residue was purified on silica gel (dichloromethane-methanol) to give both title products. The hydrochlorides were prepared by treatment of the title amines with 1M ethereal HCl.

2-Benzenesulfonyl-5-(4,5-dimethyl-3,6-dihydro-2H-pyridin-1-yl)-2-methylpentanoic acid methyl ester hydrochloride (example 183):

$\delta_H$ (400 MHz, MeOH-d$_4$): 7.84 (2H, m), 7.78 (1H, m), 7.65 (2H, m), 3.65 (3H, s), 3.58 (3H, br), 3.18 (3H, m), 2.51–2.18 (2H, m), 2.07–1.85 (2H, m), 1.78–1.61 (2H, m), 1.74 (3H, s), 1.68 (3H, s), 1.59 (3H, s); m/z (ES$^+$) 380 (M+H)$^+$.

1-(4-Benzenesulfonyl-pentyl)-4,5-dimethyl-1,2,3,6-tetrahydropyridine hydrochloride (example 184):

$\delta_H$ (400 MHz, MeOH-d$_4$): 7.91 (2H, m), 7.76 (1H, m), 7.66 (2H, m), 3.66 (1H, m), 3.51 (2H, m), 3.23–3.03 (3H, m), 2.49 (1H, m), 2.25 (1H, br d, J 17.8 Hz), 2.07–1.79 (3H, m), 1.74 (3H, s), 1.69 (3H, s), 1.57 (1H, m), 1.25 (3H, d, J 6.7 Hz); m/z (ES$^+$) 322 (M+H)$^+$.

Example 185

3-Benzenesulfonyl-6-(4,5-dimethyl-3,6-dihydro-2H-pyridin-1-yl)-3-methylhexan-2-one hydrochloride A solution of methylmagnesium bromide in tetrahydrofuran (3M, 0.43 ml, 1.3 mmol) was added to the compound of Example 183 (40 mg, 0.1 mmol) in tetrahydrofuran (2 ml) at room temperature. The mixture was stirred overnight and quenched with sat. aqueous NH$_4$Cl and extracted into dichloromethane. The combined organic extracts were dried (Na$_2$SO$_4$) and concentrated. The residue was purified on silica (dichloromethane-methanol) to give 3-benzenesulfonyl-6-(4,5-dimethyl-3,6-dihydro-2H-pyridin-1-yl)-3-methylhexan-2-one. The hydrochloride was prepared by treatment of the title amine with 1M ethereal HCl.

$\delta_H$ (360 MHz, MeOH-d$_4$): 7.83–7.73 (2H, m), 7.76 (1H, m), 7.66 (2H, m), 3.64 (1H, d, J 15.8 Hz), 3.49 (2H, m), 3.19–3.02 (3H, m), 2.43 (3H, s), 2.30–2.13 (2H, m), 1.90–1.72 (2H, m), 1.73 (3H, s), 1.67 (3H, s), 1.64 (3H, s), 1.49 (1H, m); m/z (ES$^+$) 364 (M+H)$^+$.

Example 186

2-Benzenesulfonyl-5-(4,5-dimethyl-3,6-dihydro-2H-pyridin-1-yl)-2-methylpentan-1-ol A solution of diisobutylaluminium hydride in toluene (1.0M, 6 ml, 0.6 mmol) was added to a stirred solution of 2-benzenesulfonyl-5-(4,5-dimethyl-3,6-dihydro-2H-pyridin-1-yl)-2-methyl-pentanoic acid methyl ester hydrochloride (60 mg, 0.15 mmol) in dichloromethane at 5° C. The mixture was stirred for 30 min., diluted with dichloromethane (15 ml) and quenched with water (3 drops). The resulting mixture was stirred for 30 min. and solid Na$_2$SO$_4$ was added. The mixture was filtered through a pad of Celite and concentrated. The residue was purified on silica gel (dichloromethane:methanol) to give the title product.

$\delta_H$ (360 MHz, CDCl$_3$): 7.88 (H, m), 7.67 (1H, m), 7.57 (2H, m), 3.94 (1H, d, J 12.9 Hz), 3.57 (1H, d, J 12.9 Hz), 2.82 (2H, br s), 2.64–2.33 (4H, m), 2.07 (2H, br s), 2.00 (1H, m), 1.80–1.63 (3H, m), 1.61 (3H, s), 1.56 (3H, s), 1.20 (3H, s); m/z (ES$^+$) 352 (M+H)$^+$.

Description 52

1-(4-Benzenesulfonylbutyl)-4-trifluoromethylpiperidine

Prepared from (4-bromobutane-1-sulfonyl)benzene and 4-trifluoromethylpiperidine by the method in Example 1.

$\delta_H$ (400 MHz, MeOH-d$_4$): 7.94 (2H, m), 7.75 (1H, m), 7.66 (2H, m), 3.66 (2H, m), 3.13 (2H, m), 3.01 (2H, m), 2.61 (1H, m), 2.18 (2H, m), 1.96–73 (6H, m).

Example 187

1-(4-Benzenesulfonyl-4-ethylhexyl)-4-trifluoromethylpiperidine

The product of Description 52 (45 mg, 0.13 mmol) was dissolved in tetrahydrofuran (5 ml) and cooled to −78° C. n-Butyllithium (1.6M in hexanes, 0.244 µL, 0.39 mmol) was added and the reaction stirred for 20 minutes. Bromoethane (21 µL, 0.29 mmol) was added and the mixture allowed to warm to room temperature before being diluted with water and extracted with ethyl acetate. The combined organic layers were concentrated in vacuo and the residue purified by preparative thin layer chromatography, eluting with 5% methanol/dichloromethane, followed by crystallisation from ethyl acetate to give the title compound as the hydrochloride salt.

$\delta_H$ (400 MHz, MeOH-d$_4$): 7.89 (2H, m), 7.77 (1H, m), 7.66 (2H, m), 3.17–2.94 (4H, m), 2.63 (1H, m), 2.20 (2H, m), 2.09–1.97 (2H, m), 1.93–1.71 (4H, m), 1.77 (4H, q, J 7.3 Hz), 0.98 (6H, t, J 7.3 Hz).

Example 188

1-(4-Benzenesulfonyl-3,4-dimethylpentyl)-4-trifluoromethylpiperidine

Prepared from 1-(4-benzenesulfonyl-3-methylpentyl)-4-trifluoromethylpiperidine (example 126) and methyl iodide by the method of Example 187.

$\delta_H$ (400 MHz, MeOH-$d_4$): 7.89 (2H, m), 7.76 (1H, m), 7.66 (2H, m), 3.72 (2H, m), 3.23 (2H, m), 3.06 (2H, m), 2.62 (2H, m), 2.18 (3H, m), 1.85 (2H, m), 1.63 (1H, m), 1.30 (3H, s), 1.19 (3H, s), 1.10 (3H, d, J 6.7 Hz); m/z (ES$^+$) 392 (M+H)$^+$.

Example 189

1-(4-Benzenesulfonylpentyl)-4-trifluoromethylpiperidine

Prepared from the product of Description 52 and methyl iodide by the method in Example 187.

$\delta_H$ (400 MHz, MeOH-$d_4$): 7.91 (2H, m), 7.76 (1H, m), 7.66 (2H, m), 3.65 (2H, m), 3.12 (2H, m), 3.00 (2H, m), 2.60 (1H, m), 2.17 (2H, br d, J 13.7 Hz), 2.04–1.74 (5H, m), 1.58 (1H, m), 1.24 (3H, d, J 7.0 Hz).

Example 190

1-(4-Benzenesulfonyl-4-methylpentyl)-piperidine-3-carboxylic acid diethylamide Diethylamine (0.034 ml; 0.33 mmol) followed by i-propylmagnesium chloride (0.66 ml; 1.3 mmol) was added to a stirred solution of Example 142 (0.05 g; 0.13 mmol) in THF (1 ml). The yellow solution was stirred for 30 mins at room temperature then quenched with saturated ammonium chloride solution. The aqueous phase was extracted twice with dichloromethane and the combined organic phase evaporated. The residue was purified by preparative HPLC to afford the title compound as the TFA salt (6 mg, 18%).

$\delta_H$ (360 MHz, DMSO-$d_6$): 9.5 (1H, br s), 8.8 (1H, br s), 7.87–7.76 (3H, m), 7.71–7.65 (2H, m), 3.60–2.82 (11H, m), 1.91–1.41 (6H, m), 1.25–0.98 (12H, m); MS, CI$^+$ m/z 409 (M+H)$^+$.

Compounds listed in Table 2 below were prepared by the method in Example 190 from the appropriate amine.

TABLE 2

Amides

| Example No. | Structure | m/z(ES$^+$) (M, M + H)$^+$ |
|---|---|---|
| 191 | 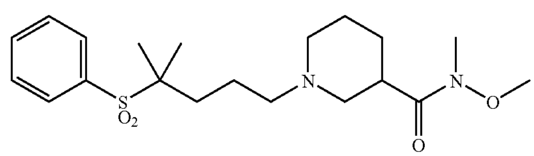 | 397 |
| 192 | 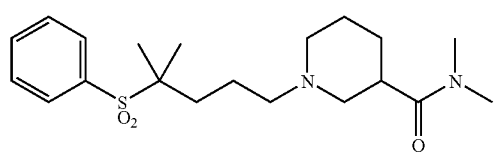 | 381 |
| 193 | 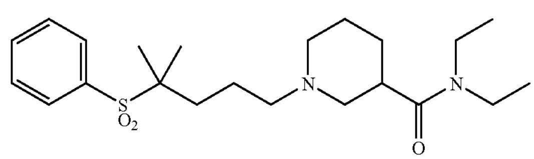 | 409 |
| 194 | 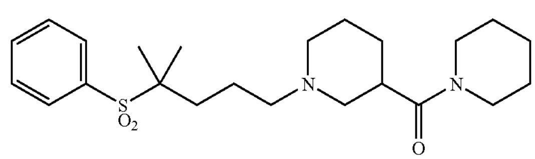 | 421 |
| 195 | 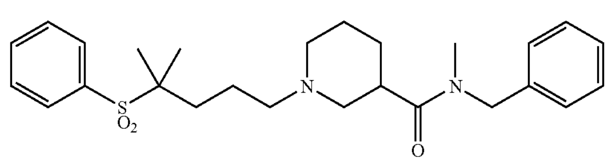 | 457 |

TABLE 2-continued

Amides

| Example No. | Structure | m/z(ES⁺) (M,M + H)⁺ |
|---|---|---|
| 196 | 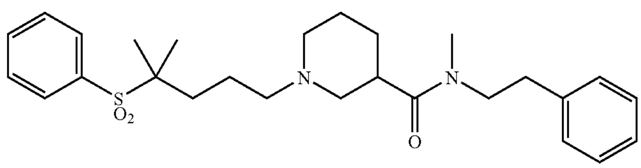 | 471 |
| 197 | 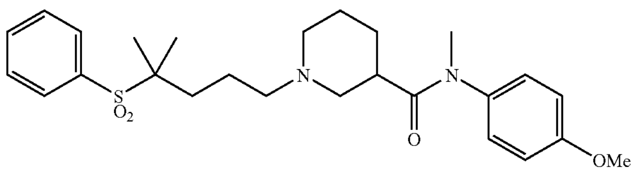 | 473 |
| 198 | 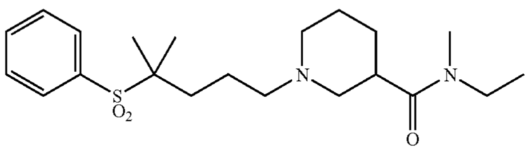 | 395 |
| 199 | 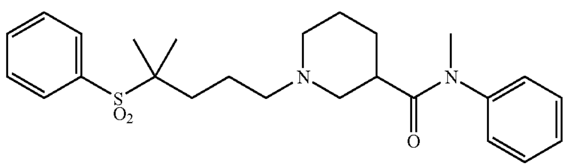 | 443 |
| 200 | 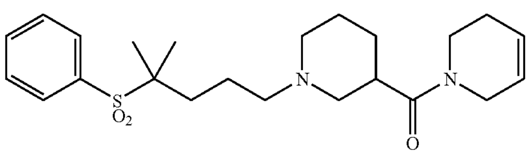 | 419 |
| 201 | 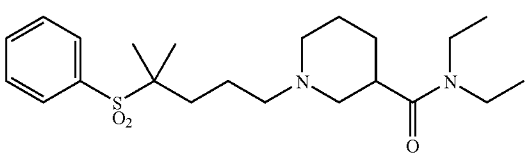 | 409 |

Example 202

1-[1-(4-Benzenesulfonyl-4-methylpentyl)-piperidin-3-yl]-but-2-yn-1-one

A solution of 1-propynylmagnesium bromide in tetrahydrofuran (0.5M, 5 ml, 2.5 mmol) was added to a stirred slurry of Example 142 (50 mg, 0.14 mmol), N,O-dimethylhydroxylamine hydrochloride (40 mg, 0.42 mmol) and tetrahydrofuran at 0° C. The mixture was stirred at 0° C. for 1 hour and at room temperature overnight. The reaction mixture was quenched with satd. aqueous NH₄Cl and extracted into dichloromethane. The organic phase was dried (Na₂SO₄) and concentrated. The residue was purified on silica gel (dichloromethane:methanol) to give the title compound (25 mg, 47%).

$\delta_H$ (400 MHz, CDCl₃): 7.88 (2H, m), 7.66 (1H, m), 7.56 (2H, m), 2.99 (1H, br d, J 11.0 Hz), 2.71 (1H, m), 2.59 (1H, m), 2.34 (2H, t, J 7.4 Hz), 2.20 (1H, br t, J 11.0 Hz), 2.03 (3H, s), 1.99 (2H, m), 1.78–1.66 (3H, m), 1.63–1.50 (3H, m), 1.45 (1H, m), 1.29 (6H, s); m/z (ES⁺) 376 (M+H)⁺.

Example 203

1-[1-(4-Benzenesulfonyl-4-methylpentyl)-piperidin-3-yl]-butan-1-one

A solution of n-propylmagnesium chloride in diethylether (2M, 0.494 ml, 0.988 mmol) was added to a stirred solution of Example 191 in tetrahydrofuran and stirred for 1.5 h. The reaction mixture was quenched with satd. aqueous ammonium chloride and extracted into dichloromethane. The organic phase was dried (Na₂SO₄) and concentrated and purified on silica gel (dichloromethane-methanol) to give the title product.

$\delta_H$ (400 MHz, CDCl₃): 7.87 (2H, m), 7.66 (1H, m), 7.55 (2H, m), 2.92 (1H, m), 2.80 (1H, m), 2.59 (1H, m), 2.42 (2H, dt, J 1.2 and 6.3 Hz), 2.33 (2H, m), 2.04 (1H, t, J 11.0 Hz), 1.97–1.85 (2H, m), 1.76–1.66 (3H, m), 1.64–1.50 (5H, m), 1.32 (1H, m), 1.29 (6H, s), 0.90 (3H, t, J 7.4 Hz); m/z (ES$^+$) 380 (M+H)$^+$.

Compounds listed in Table 3 below were prepared by the method in Example 202 or 203.

mixture of diastereoisomers which was repurified using reverse phase HPLC (acetonitrile:0.1% aqueous trifluoroacetic acid).

$\delta_H$ (400 MHz, MeOH-d$_4$): 7.88 (4H, m), 7.76 (2H, m), 7.66 (4H, m), 3.65 (1H, br d, J 12.0 Hz), 3.55 (2H, br d, J

TABLE 3

Ketones

| Example No. | Structure | m/z (ES$^+$) (M,M + H)$^+$ |
|---|---|---|
| 204 | | 366 |
| 205 | | 394 |
| 206 | | 352 |

Description 53

1-(4-Benzenesulfonyl-4-methylpentyl)-piperidine-3-carbaldehyde

A solution of diisobutylaluminium hydride in dichloromethane (1.0M, 1.27 ml; 1.27 mmol) was added to a stirred solution of Example 191 (210 mg, 0.53 mmol) in dichloromethane at −78° C. The mixture was stirred for 1 hour and quenched with water (4 drops) and diluted with dichloromethane (30 ml). The resulting mixture was stirred vigourously for 1 hours, dried over Na$_2$SO$_4$ and filtered through a pad of Celite. The filtrate was concentrated in vacuo the crude title aldehyde that was used in the next step without purification.

Description 54

1-[1-(4-Benzenesulfonyl-4-methylpentyl)-piperidin-3-yl]-2-methylpropan-1-ol trifluoroacetate A solution of i-propyl magnesium chloride in tetrahydrofuran (2M, 0.5 ml, 1 mmol) was added to a stirred solution of product of Description 53 (100 mg, 0.29 mmol) in THF (2 ml) at 0° C. The mixture was stirred for 30 min., then quenched with sat. aqueous NH$_4$Cl and extracted into dichloromethane. The organic phase was dried (Na$_2$SO$_4$) and concentrated. The residue was purified on silica gel (i-hexane:ethyl acetate) to give the title product as a 1:1

12.0 Hz), 3.40 (1H, br d, J 12.0 Hz), 3.17–3.01 (6H, m), 2.93–2.65 (4H, m), 2.07–1.64 (18H, m), 1.38 (2H, m), 1.30 (12H, s), 0.98 (3H, d, J 6.4 Hz), 0.96 (3H, d, J 6.7 Hz), 0.91 (3H, d, J 4.4 Hz), 0.90 (3H, d, J 4.7 Hz); m/z (ES$^+$) (M+H)$^+$.

Example 207

1-[1-(4-Benzenesulfonyl-4-methylpentyl)-piperidin-3-yl]-2-methylpropan-1-one trifluoroacetate Dess-Martin periodinane (0.55 g, 1.3 mmol) was added to a mixture of product of Description 54 (230 mg, 0.46 mmol). The mixture was stirred at room temperature for 30 min. and 10% aqueous Na$_2$S$_2$O$_3$ (4 ml) and sat. aqueous NaHCO$_3$ (4 ml) were added. The resulting mixture was vigorously stirred for 30 min. and then extracted into dichloromethane. The organic phase was dried (Na$_2$SO$_4$) and concentrated. The residue was purified using reverse phase HPLC (acetonitrile:0.1% aqueous trifluoroacatic acid) to give the title product.

$\delta_H$ (400 MHz, MeOH-d$_4$, 4:1 mixture of rotamers): 7.88 (2H, m), 7.76 (1H, m), 7.66 (2H, m), 3.71 (0.4H, br d, J 12.9 Hz), 3.58 (1.6H, br d, J 12.0 Hz), 3.35 (0.4H, m), 3.21–2.78 (5.6H, m), 2.26–1.70 (7H, m), 1.43 (1H, m), 1.30 (6H, s), 1.14 (0.6H, d, J 7.0 Hz), 1.12 (2.4H, d, J 7.0 Hz), 1.10 (0.6H, d, J 7.0 Hz), 1.07 (2.4H, d, J 7.0 Hz); m/z (ES$^+$) 380 (M+H)$^+$.

Description 55

1-[1-(4-Benzenesulfonyl-4-methylpentyl)-piperidin-3-yl]-2,2-dimethylpropan-1-ol trifluoroacetate A solution of t-butyl magnesium chloride in diethyl ether (2M, 0.5 ml, 1 mmol) was added to a stirred solution of product of Description 54 (100 mg, 0.29 mmol) in tetrahydrofuran (2 ml) at 0° C. The mixture was stirred for 30 min., then quenched with sat. aqueous NH$_4$Cl and extracted into dichloromethane. The organic phase was dried (Na$_2$SO$_4$) and concentrated. The residue purified on silica gel (i-hexane:ethyl acetate) to give the title alcohol as a 1:1 mixture of diastereoisomers which were separated using reverse phase HPLC (acetonitrile:0.1% aqueous trifluoroacatic acid).

Isomer A: $\delta_H$ (360 MHz, MeOH-d$_4$): 7.89 (2H, m), 7.76 (1H, m), 7.65 (2H, m), 3.66–3.46 (2H, m), 3.45–3.26 (1H, m), 3.20–2.72 (4H, m), 2.17–1.52 (8H, m), 1.30 (6H, s), 0.94 (9H, s); m/z (ES$^+$) 396 (M+H)$^+$.

Isomer B: $\delta_H$ (400 MHz, MeOH-d$_4$): 7.88 (2H, m), 7.76 (1H, m), 7.66 (2H, m), 3.53 (1H, br d, J 12.0 Hz), 3.35 (1H, br m, J 12.3 Hz), 3.12–3.04 (3H, m), 2.89 (1H, t, J 12.3 Hz), 2.79 (1H, dt, J 2.9 and 13.2 Hz), 2.11 (1H, m), 2.03–1.85 (4H, m), 1.80–1.70 (3H, m), 1.55 (1H, dq, J 2.9 and 12.3 Hz), 1.31 (6H, s), 0.96 (9H, s); m/z (ES$^+$) 396 (M+H)$^+$.

Example 208

1-[1-(4-Benzenesulfonyl-4-methylpentyl)-piperidin-3-yl]-2,2-dimethylpropan-1-one trifluoroacetate Dess-Martin periodinane (40 mg, 0.1 mmol) was added to a mixture of product of Description 55 (10 mg, 0.02 mmol). The mixture was stirred at room temperature for 30 min. and 10% aqueous Na$_2$S$_2$O$_3$ (4 ml) and sat. aqueous NaHCO$_3$ (4 ml) were added. The resulting mixture was vigourously stirred for 30 min. and then extracted into dichloromethane. The organic phase was dried (Na$_2$SO$_4$) and concentrated. The residue was purified using reverse phase HPLC (acetonitrile:0.1% aqueous trifluoroacetic acid) to give the title product (6 mg, 59%).

$\delta_H$ (400 MHz, MeOH-d$_4$): 7.88 (2H, m), 7.76 (1H, m), 7.65 (2H, m), 3.69–3.34 (3H, m) 3.11 (2H, t, J 7.6 Hz), 3.00 (1H, t, J 11.9 Hz), 2.93 (1H, td, J 2.6 and 12.3 Hz), 2.09–1.70 (8H, m), 1.52 (1H, m), 1.30 (6H, s), 1.8 (9H, s); m/z (ES$^+$) 394 (M+H)$^+$.

Example 209 and 210

1-[1-(4-Benzenesulphonyl-4-methylpentyl)-piperidin-3-yl]ethanone trans-O-methyloxime and 1-[1-(4-benzenesulphonyl-4-methylpentyl)-piperidin-3-yl]ethanone cis-O-methyloxime A solution of Example 191 (519 mg, 1.31 mmol) in tetrahydrofuran (10 ml) was cooled to 0° C. and treated with methyl magnesium iodide (1.0M in tetrahydrofuran, 1.97 ml, 1.97 mmol). The reaction was stirred for 1 hour then quenched with saturated aqueous ammonium chloride solution. The mixture was extracted with ethyl acetate and the combined organic layers dried (MgSO$_4$) and concentrated in vacuo. The residue was dissolved in ethanol (5 ml) and tetrahydrofuran (3 ml) and treated with methoxylamine hydrochloride (383 mg, 4.59 mmol) and a solution of sodium hydrogen carbonate (385 mg, 4.59 mmol) in water (3 ml). The reaction was stirred at 50° C. for 3 hours. The mixture was concentrated in vacuo and the residue partitioned between ethyl acetate and water. The organic layer was concentrated in vacuo and the residue purified by preparative thin layer chromatography, eluting with 5% methanol/dichloromethane, to give two diastereoisomers.

Example 209: $\delta_H$ (400 MHz, CDCl$_3$): 7.88 (2H, m), 7.65 (1H, m), 7.55 (2H, m), 3.79 (3H, s), 3.30 (1H, m), 3.01–2.85 (2H, m), 2.41 (1H, m), 2.36 (2H, t, J 7.4 Hz), 2.03–1.82 (3H, m), 1.80 (3H, s), 1.77–1.46 (8H, m), 1.29 (6H, s), 1.25 (1H, m); m/z (ES$^+$) 381 (M+H)$^+$.

Example 210: $\delta_H$ (400 MHz, CDCl$_3$): 7.87 (2H, m), 7.65 (1H, m), 7.56 (2H, m), 3.82 (3H, s), 3.30 (1H, m), 2.83 (2H, m), 2.29 (2H, t, J 7.4 Hz), 1.92–1.79 (2H, m), 1.78 (3H, s), 1.77–1.61 (6H, m), 1.29 (6H, s), 1.26 (1H, m); m/z (ES$^+$) 381 (M+H)$^+$.

Compounds listed in Table 4 below were prepared by the method in Example 209 and 210 from the appropriate O-alkyl hydroxylamines.

TABLE 4

Oximes

| Example No. | Structure | m/z(ES$^+$) (M, M + H)$^+$ |
|---|---|---|
| 211 | 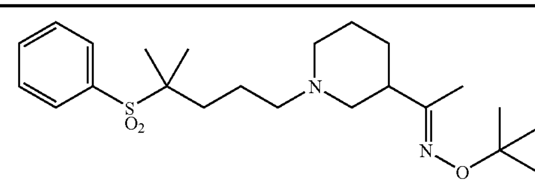 | 423 |
| 212 | 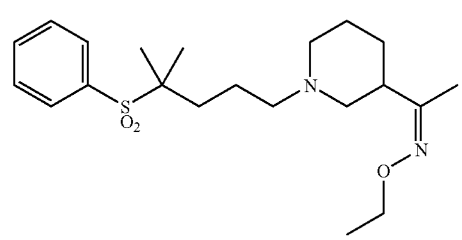 | 395 |

TABLE 4-continued

Oximes

| Example No. | Structure | m/z(ES⁺) (M, M + H)⁺ |
|---|---|---|
| 213 | 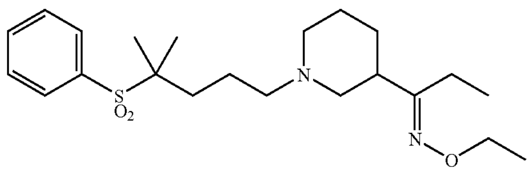 | 395 |
| 214 | 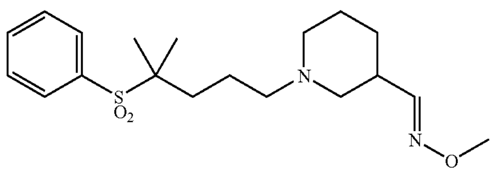 | 367 |

Compounds listed in Table 5 below were prepared by the method in Example 183 from appropriate bromides and pyridine derivatives.

TABLE 5

Olefins-1

| Example No. | Structure | m/z(ES⁺) (M,M + H)⁺ |
|---|---|---|
| 215 | 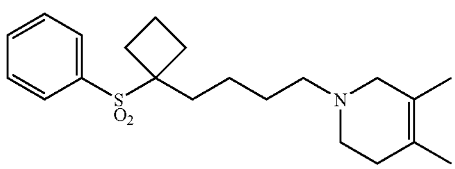 | 362 |
| 216 | 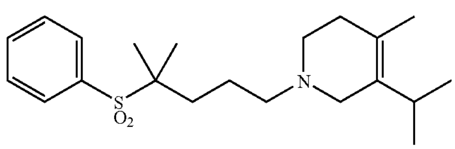 | 364 |
| 217 | 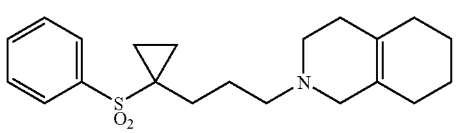 | 360 |
| 218 | 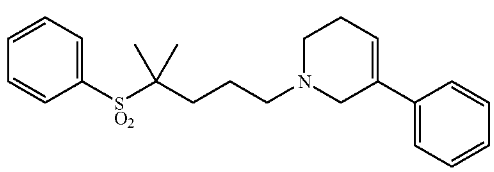 | 384 |
| 219 | 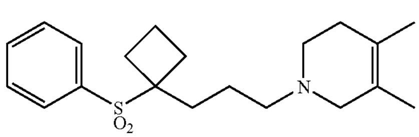 | 348 |

TABLE 5-continued

Olefins-1

| Example No. | Structure | m/z(ES+) (M,M + H)+ |
|---|---|---|
| 220 | 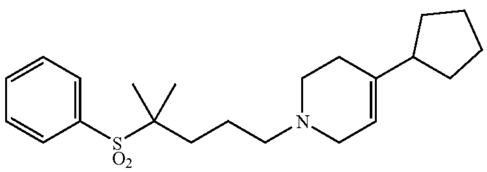 | 376 |
| 221 | 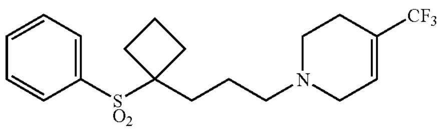 | 388 |
| 222 | 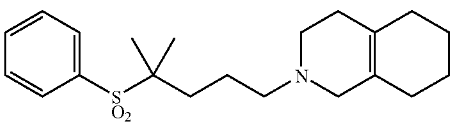 | 362 |
| 223 | 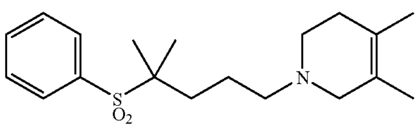 | 336 |
| 224 | 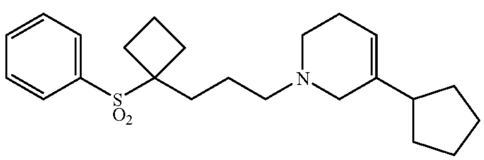 | 388 |
| 225 | 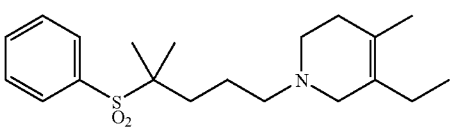 | 350 |
| 226 | 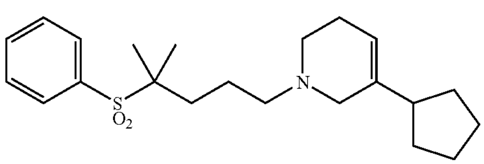 | 376 |
| 227 | 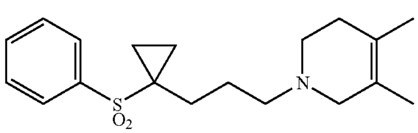 | 334 |
| 228 | 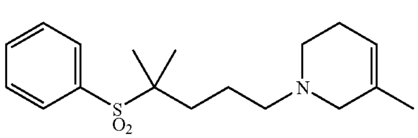 | 322 |

Example 229

1-(4-Benzenesulfonyl-4-methylpentyl)-5-bromo-1,2,3,6-tetrahydropyridine

3-Bromopyridine (0.32 ml; 3.3 mmol) was added to a solution of 5-bromo-2-methylpentane-2-sulfonyl)benzene (1.0 g; 3.3 mmol) in 2-butanone (20 ml). The solution was stirred for 5 days at reflux then filtered. The solid was washed with acetone and dried in vacuo to give the pyridinium bromide (312 mg) as a beige solid. Sodium borohydride (0.05 g; 1.3 mmol) was added to a solution of the pyridinium bromide (0.31 g; 0.67 mmol) in ethanol (20 ml) and water (2 ml) at room temperature. The mixture was stirred for 24 hr then extracted with ethyl acetate. The organic phase was washed twice with water. The organic phase was dried (MgSO$_4$) and evaporated. Chromatography on silica gel using dichloromethane/methanol as eluent afforded a yellow oil (190 mg, 15%).

$\delta_H$ (400 MHz, CDCl$_3$): 7.88 (2H, m), 7.66 (1H, m), 7.56 (2H, t, J 7.7 Hz), 6.06 (1H, m), 3.16 (2H, d, J 1.8 Hz), 2.58 (2H, t, J 5.6 Hz), 2.43 (2H, t, J 7.2 Hz), 2.21 (2H, m), 1.74 (2H, m), 1.61 (2H, m), 1.30 (6H, s).

Example 230

1-(4-Benzenesulfonyl-4-methylpentyl)-5-(4-methoxyphenyl)-1,2,3,6-tetrahydropyridine 2M Potassium carbonate solution (containing tetra-n-butylammonium hydroxide) (0.25 ml) followed by 4-methoxybenzeneboronic acid (0.056 g; 0.37 mmol) was added to a solution of Example 229 (0.095 g; 0.25 mmol) in 1,4-dioxane (6 ml). The solution was deoxygenated with nitrogen at room temperature for 5 minutes. Tetrakistriphenylphosphine palladium(0) (catalytic) was added and the solution stirred for 30 minutes at 80° C. After cooling to room temperature, ethyl acetate was added and the organic phase separated then washed twice with water. The organic layer was dried (MgSO$_4$) and evaporated in vacuo. Purification using an SCX cartridge eluting with ⅑ NH$_3$/MeOH afforded the title compound as a yellow oil (90 mg, 87%).

$\delta_H$ (360 MHz, CDCl$_3$): 7.87 (2H, dd J 2 and 6.7 Hz), 7.66–7.62 (1H, m), 7.57–7.52 (2H, m), 7.28–7.24 (2H, m), 6.85 (2H, dd J 2 and 6.7 Hz), 6.02–5.98 (1H, m), 3.80 (3H, s), 3.29–3.27 (2H, m), 2.61–2.56 (2H, m), 2.52–2.46 (2H, m), 2.37–2.30 (2H, m), 1.80–1.62 (4H, m), 1.31 (6H, s); MS, CI$^+$ m/z=414 for (M+H)$^+$.

Compounds listed in Table 6 below were prepared using the above protocol from the appropriate arylboronic acid.

TABLE 6

Olefins-2

| Example No. | Structure | m/z(ES$^+$) (M,M + H)$^+$ |
|---|---|---|
| 231 | 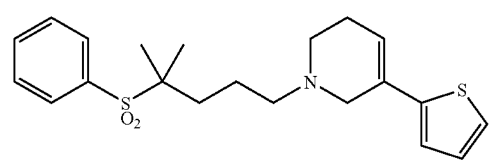 | 390 |
| 232 | 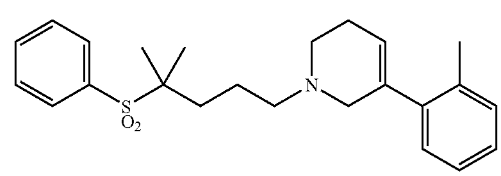 | 398 |
| 233 | 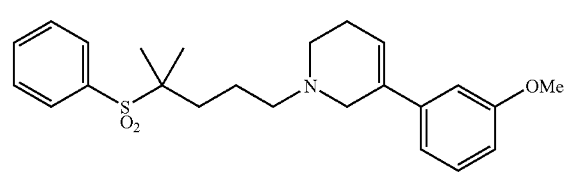 | 414 |
| 234 | 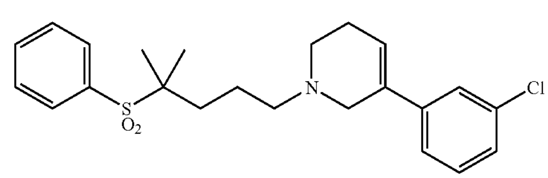 | 418,420 |

TABLE 6-continued

Olefins-2

| Example No. | Structure | m/z(ES+) (M,M + H)+ |
|---|---|---|
| 235 | 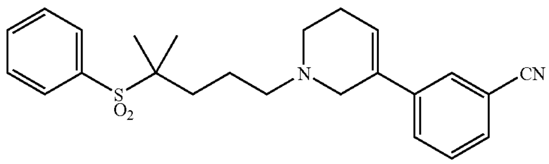 | 409 |
| 236 | 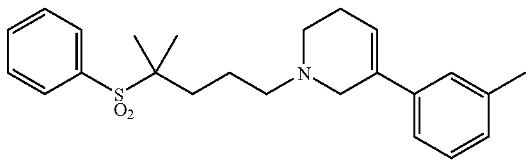 | 398 |
| 237 | 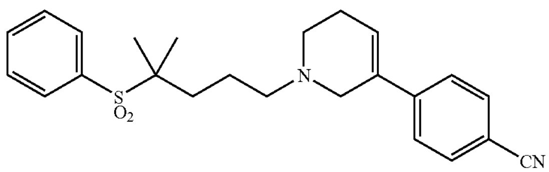 | 409 |
| 238 | 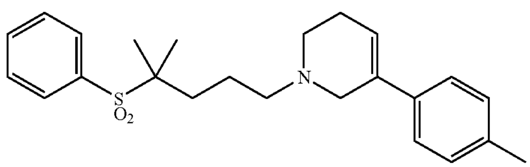 | 398 |
| 239 | 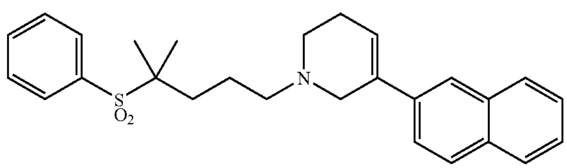 | 434 |
| 240 | 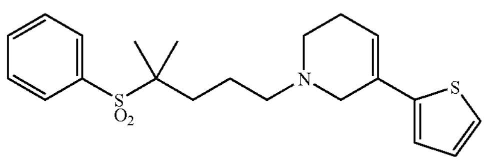 | 390 |
| 241 | 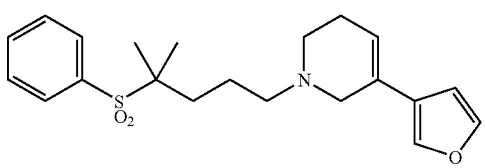 | 374 |
| 242 | 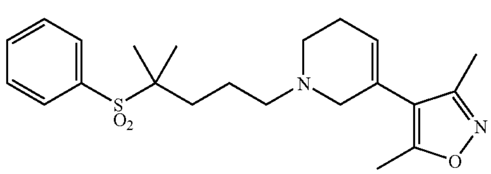 | 403 |

TABLE 6-continued

Olefins-2

| Example No. | Structure | m/z(ES+) (M,M + H)+ |
|---|---|---|
| 243 | 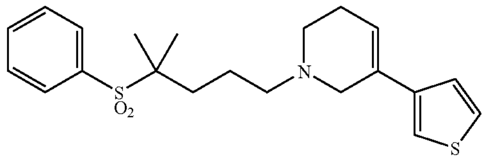 | 390 |

Example 244

1-(4-Benzenesulfonyl-4-methylpentyl)-3-(4-methoxyphenyl)piperidine

Example 230 (0.08 g; 0.2 mmol) was hydrogenated over palladium on carbon in ethanol (5 ml) under an atmosphere of hydrogen for 18 hr. The catalyst was removed and the solvent evaporated. The residue was purified by column chromatography on silica gel using methanol/dichloromethane as eluent to give the title compound (50 mg, 60%). The title compound was converted to the oxalate salt.

$\delta_H$ (360 MHz, DMSO-$d_6$): 7.83 (2H, d, J 7.0 Hz), 7.78 (1H, d, J 7.4 Hz), 7.67 (2H, t, J 7.7 Hz), 7.18 (2H, d, J 8.8 Hz), 6.91 (2H, d, J 8.8 Hz), 4.81 (1H, br s), 3.73 (3H, s), 3.42–3.35 (2H, m), 2.96–2.74 (4H, m), 1.94–1.50 (8H, m), 1.20 (6H, s).; MS, CI+ m/z=416 for (M+H)+.

Compounds listed in Table 7 below were prepared using the above reduction protocol from the appropriate tetrahydropyridine.

TABLE 7

| Example No. | Structure | m/z(ES+) (M,M + H)+ |
|---|---|---|
| 245 | 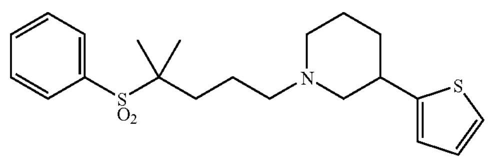 | 392 |
| 246 | 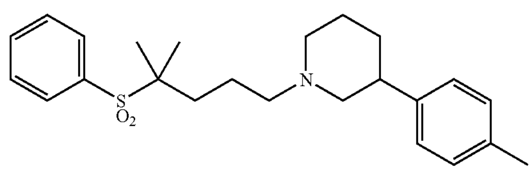 | 400 |
| 247 | 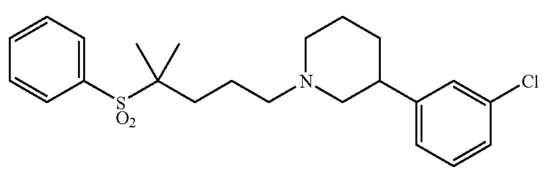 | 420 |
| 248 | 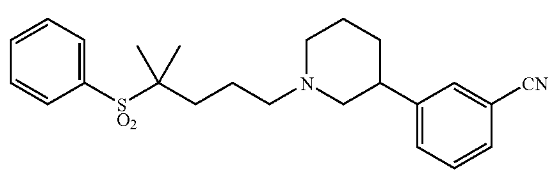 | 411 |
| 249 | 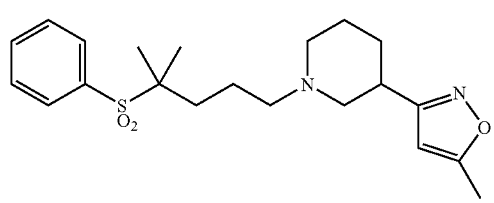 | 391 |

TABLE 7-continued

| Example No. | Structure | m/z(ES+) (M,M + H)+ |
|---|---|---|
| 250 | 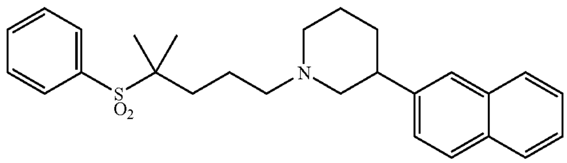 | 436 |
| 251 | 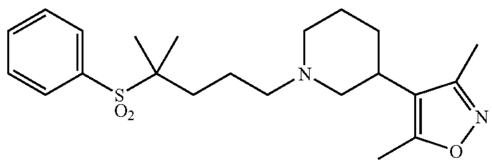 | 405 |
| 252 | 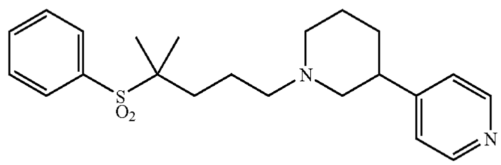 | 397 |
| 253 | 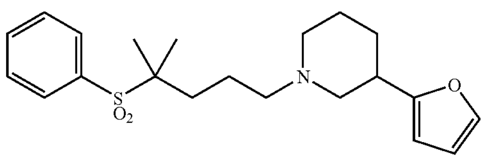 | 376 |
| 254 | 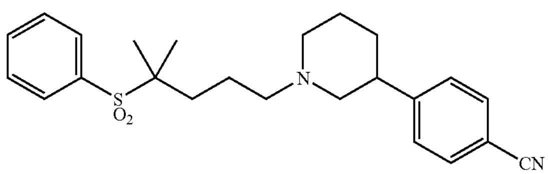 | 411 |
| 255 | 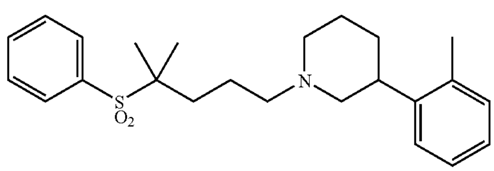 | 400 |
| 256 | 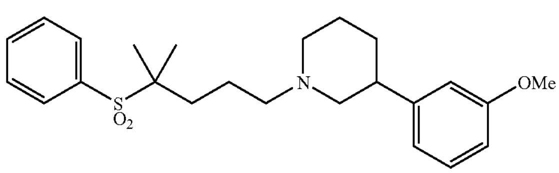 | 416 |
| 257 | 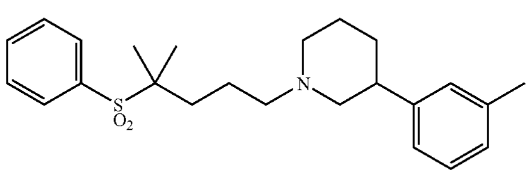 | 400 |
| 258 | 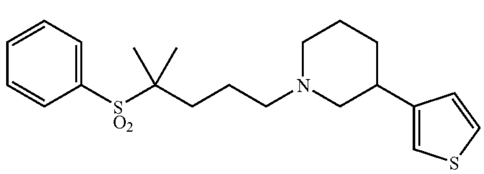 | 392 |

TABLE 7-continued

| Example No. | Structure | m/z(ES⁺) (M,M + H)⁺ |
|---|---|---|
| 259 | 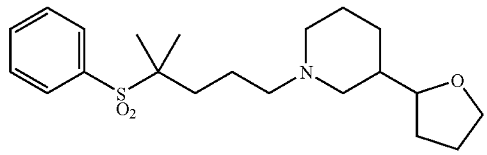 | 380 |
| 260 | 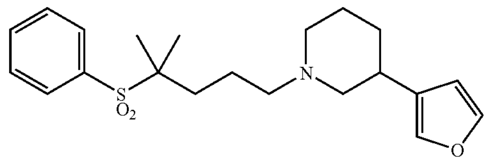 | 376 |
| 261 | 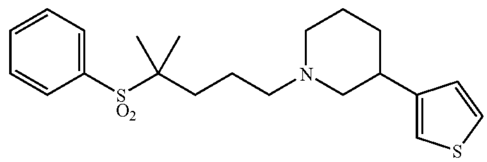 | 392 |
| 262 | 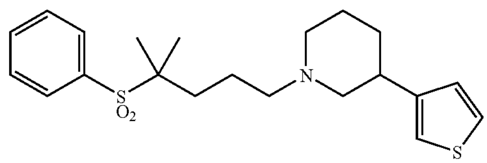 | 392 |

Example 263

1-(4-Benzenesulfonyl-4-methylpentyl)-3-isopropenylpiperidine

A solution of Tebbe Reagent in toluene (0.5M, 1.5 ml, 0.75 mmol) was added to a stirred mixture of Example 206 (90 mg, 0.25 mmol), pyridine (0.2 ml, 2.5 mmol) toluene (1 ml) and tetrahydrofuran (1 ml) at −20° C. The mixture was stirred at −20÷0° C. for 2 hours and carefully quenched with 2M NaOH (10 ml). After extraction with dichloromethane, the organic phase was dried (Na₂SO₄) and concentrated. The residue was purified on silica gel (dichloromethane:methanol) to give the title product.

$\delta_H$ (360 MHz, CDCl₃): 7.88 (2H, m), 7.65 (1H, m), 7.55 (2H, m), 4.74 (1H, m), 4.69 (1H, s), 2.91 (2H, br d, J 10.5 Hz), 2.33 (2H, br t, J 6.7 Hz), 2.17 (1H, m), 1.95–1.50 (9H, m), 1.72 (3H, s), 1.29 (6H, s), 1.16 (1H, dq, J 4.2 and 12.6 Hz).

Example 264

1-(4-Benzenesulfonyl-4-methylpentyl)-3-vinylpiperidine i-Propyl alcohol was added to a stirred solution of triphenylphosphine (270 mg, 1.04 mmol) and Wilkinson's catalyst (30 mg, 0.03 mmol) in tetrahydrofuran (10 ml) followed by a solution of product of Description 53 (270 mg, 0.8 mmol) in tetrahydrofuran (5 ml). A solution of trimethylsilyldiazomethane in hexane (2.0M, 1 ml, 2 mmol) was added at room temperature. The mixture was stirred overnight and concentrated. The residue was purified on silica (dichloromethane:methanol) to give the title product.

$\delta_H$ (360 MHz, CDCl₃): 7.87 (2H, m), 7.65 (1H, m), 7.55 (2H, m), 5.72 (1H, ddd, J 7.4, 10.6 and 17.6 Hz), 5.02 (1H, dt, J 1.6 and 17.6 Hz), 4.96 (1H, d, J 10.6 Hz), 2.82 (2H, br d, J 11.0 Hz), 2.30 (2H, t, J 7.4 Hz), 2.24 (1H, m), 1.87 (1H, dt, J 2.7 and 11.7 Hz), 1.81–1.49 (8H, m), 1.29 (6H, s), 1.07 (1H, ddt, J 4.3 and 12.5 Hz); m/z (ES⁺) 336 (M+H)⁺.

Description 56

1-(4-Benzenesulfonyl-4-methylpentyl)-4-ethoxycarbonylpiperidine

The title compound was prepared by the method in Example 1 from product of Description 10 and ethyl isonipecotate.

$\delta_H$ (400 MHz, CDCl₃): 7.87 (2H, m), 7.65 (1H, m), 7.55 (2H, m), 3.14 (2H, q, J 7.0 Hz), 2.84 (2H, m), 2.32–2.21 (3H, m), 1.98 (2H, m), 1.88 (2H, m), 1.79–1.66 (4H, m), 1.55 (2H, m), 1.29 (6H, s), 1.25 (3H, t, J 7.0 Hz); m/z (ES⁺) 382 (M+H)⁺.

Example 265

1-(4-Benzenesulfonyl-4-methylpentyl)-4-ethynylpiperidine 1-(4-Benzenesulfonyl-4-methylpentyl)-4-ethoxycarbonylpiperidine (0.3 g, 0.79 mmol) was dissolved in dichloromethane (5 ml) and cooled to −78° C. Diisobutylaluminium hydride (1.0M in dichloromethane, 1.0 ml, 1.0 mmol) was added. The reaction was stirred for 30 minutes at −78° C. then quenched by the addition of ethyl acetate (0.5 ml) and water (0.1 ml). The mixture was stirred at room temperature for 10 minutes then filtered through Celite. The filtrate was concentrated in vacuo. The residue was dissolved in methanol (20 ml). Dimethyl (1-diazo-2-oxopropyl) phosphonate (0.3 g, 1.56 mmol) and potassium carbonate (0.23 g, 1.65 mmol) were added and the reaction stirred at room temperature for 1 hour. The mixture was concentrated in vacuo and the residue partitioned between ethyl acetate and brine. The organic layer was dried (MgSO$_4$) and concentrated in vacuo. The residue was purified by flash column chromatography on silica gel, eluting with 2–4% methanol/dichloromethane, to give the title compound (90 mg, 34%). NMR of hydrochloride salt:

$\delta_H$ (400 MHz, MeOD-d$_4$): 7.90–7.86 (2H, m), 7.77–7.75 (1H, m), 7.68–7.64 (2H, m), 3.61–3.47 (2H, m), 3.15–3.07 (2H, m), 3.02–2.93 (1H, m), 2.70–2.63 (1H, m), 2.24–2.14 (1H, m), 2.12–1.97 (2H, m), 1.96–1.88 (4H, m), 1.79–1.74 (2H, m), 1.33–1.31 (1H, m), 1.31 (6H, s); m/z (ES$^+$) 334 (M+H)$^+$.

Description 57

1-(4-Benzenesulfonyl-4-methylpentyl)-3-hydroxypiperidine (5-Bromo-2-methylpentane-2-sulfonyl)benzene (5 g, 16.4 mmol), 3-hydroxypiperidine (2 g, 20 mmol) and potassium carbonate (4.5 g, 33 mmol) in acetonitrile (50 ml) were stirred at 50° C. for 18 hours. The cooled reaction mixture was partitioned between ethyl acetate and brine. The organic layer was dried (MgSO$_4$) and concentrated in vacuo. The residue was purified by flash column chromatography on silica, eluting with 120:8:1 dichloromethane/methanol/ammonia, to give the title compound (5.2 g, 98%).

$\delta_H$ (400 MHz, CDCl$_3$): 7.88–7.86 (2H, m), 7.68–7.64 (1H, m), 7.58–7.54 (2H, m), 3.79 (1H, br s), 2.44–2.41 (3H, m), 2.31 (2H, t, J 7 Hz), 2.28–2.23 (1H, m), 1.78–1.68 (3H, m), 1.61–1.49 (5H, m), 1.29 (6H, s).

Example 266

1-(4-Benzenesulfonyl-4-methylpentyl)-3-methoxypiperidine 1-(4-Benzenesulfonyl-4-methylpentyl)-3-hydroxypiperidine (0.1 g, 0.31 mmol), methyl iodide (22 μL, 0.35 mmol) and sodium hydride (60% dispersion in mineral oil, 15 mg, 0.35 mmol) were combined in tetrahydrofuran (2 ml) and stirred at room temperature for 18 hours. The reaction was quenched by the addition of water and brine and the mixture extracted with ethyl acetate. The combined organic layers were dried (MgSO$_4$) and concentrated in vacuo. The residue was purified by flash column chromatography on silica gel, eluting with 2–5% methanol/dichloromethane, to give the title compound. The hydrochloride salt was obtained by treatment with ethereal hydrogen chloride and crystallisation from ethanol/diethyl ether (77 mg, 74%). NMR of hydrochloride salt:

$\delta_H$ (400 MHz, MeOD-d$_4$): 7.90–7.88 (2H, m), 7.78–7.74 (1H, m), 7.66 (2H, t, J 7.7 Hz), 3.76–3.69 (1H, m), 3.64–3.57 (1H, m), 3.40 (3H, s), 3.09–2.94 (4H, m), 2.13–1.99 (2H, m), 1.96–1.81 (2H, m), 1.80–1.72 (3H, m), 1.63–1.55 (1H, m), 1.31–1.30 (7H, m); m/z (ES$^+$) 340 (M+H)$^+$.

Example 267

1-(4-Benzenesulfonyl-4-methylpentyl)-3-benzyloxypiperidine

The title compound was prepared from 1-(4-benzenesulfonyl-4-methylpentyl)-3-hydroxypiperidine and benzyl bromide.

$\delta_H$ (400 MHz, CDCl$_3$): 7.87 (2H, m), 7.64 (1H, m), 7.54 (2H, m), 7.33 (5H, m), 4.59 (1H, AB, J 11.7 Hz), 4.53 (1H, AB, J 11.7 Hz), 3.47 (1H, m), 2.94 (1H, m), 2.65 (1H, m), 2.32 (2H, m), 2.05–1.92 (3H, m), 1.78–1.65 (3H, m), 1.60–1.42 (3H, m), 1.34–1.25 (1H, m), 1.29 (6H, s); m/z (ES$^+$) 415 (M+H)$^+$.

Example 268

1-(4-Benzenesulfonyl-4-methylpentyl)-3-(1-propoxy)piperidine

The title compound was prepared from 1-(4-benzenesulfonyl-4-methylpentyl)-3-hydroxypiperidine and n-propyl iodide. NMR of hydrochloride salt:

$\delta_H$ (400 MHz, MeOD-d$_4$): 7.90–7.88 (2H, m), 7.78–7.75 (1H, m), 7.66 (2H, t, J 7.7 Hz), 3.85–3.77 (1H, m), 3.62–3.45 (3H, m), 3.10–2.96 (4H, m), 2.10–2.01 (2H, m), 1.99–1.82 (2H, m), 1.79–1.73 (3H, m), 1.65–1.60 (3H, m), 1.31–1.30 (7H, m), 0.96 (3H, t, J 7.4 Hz); m/z (ES$^+$) 368 (M+H)$^+$.

Example 269

1-(4-Benzenesulfonyl-4-methylpentyl)-3-(2-propoxy)piperidine

The title compound was prepared from 1-(4-benzenesulfonyl-4-methylpentyl)-3-hydroxypiperidine and i-propyl iodide.

NMR; m/z (ES+) 368 (M+H)$^+$.

Description 58

[1-(4-Benzenesulfonyl-4-methylpentyl)piperidin-3-yl]methanol hydrochloride

The title compound was prepared as described in Example 1 from the product of Description 10 and piperidin-3-yl-methanol.

NMR of hydrochloride salt:

$\delta_H$ (400 MHz, MeOD-d$_4$): 7.88 (2H, m), 7.74 (1H, m), 7.64 (2H, m), 3.43 (1H, dd, J 5.1 and 11 Hz), 3.28 (1H, dd, J 6.7 and 11 Hz), 3.00 (1H, m), 2.87 (1H, m), 2.36–2.28 (2H, m), 1.93 (1H, dt, J 2.7 and 11.7 Hz), 1.81–1.51 (9H, m), 1.29 (6H, s), 0.95 (1H, m).

Example 270

1-(4-Benzenesulfonyl-4-methylpentyl)-3-ethoxymethylpiperidine

Sodium hydride (55 mg of 60% dispersion in oil) was washed with i-hexane and treated with tetrahydrofuran (3 ml). [1-(4-Benzenesulfonyl-4-methyl-pentyl)-piperidin-3-yl]-methanol (95 mg, 0.28 mmol) was added and the mixture was stirred at room temperature for 10 min. Ethyl iodide (0.5 ml) was added to the mixture that was stirred for 5 hours. The reaction mixture was quenched with 25% ammonia and extracted into dichloromethane. The combined organic extract were dried (Na$_2$SO$_4$) and concentrated. The residue was purified by chromatography on silica gel (dichloromethane:methanol) to give to give the title compound.
NMR of hydrochloride salt:

$\delta_H$ (400 MHz, MeOD-d$_4$): 7.89 (2H, m), 7.76 (1H, m), 7.66 (2H, m), 3.62–3.40 (5H, m), 3.10 (2H, m), 2.85 (1H, m), 2.74 (1H, t, J 12.1 Hz), 2.18–1.71 (8H, m), 1.34 (1H, m), 1.31 (6H, s), 1.17 (3H, t, J 7 Hz): m/z (ES$^+$) 368 (M+H)$^+$.

Description 59

1-(4-Benzenesulfonyl-4-methylpentyl)-3-piperidinone

Dimethylsulphoxide (1.2 ml, 16.6 mmol) was added to a solution of oxalyl chloride (1.5 ml, 16.6 mmol) in dichloromethane (200 ml) at −78° C. and stirred for 15 minutes. 1-(4-Benzenesulfonyl-4-methylpentyl)-3-hydroxypiperidine (3.5 g, 11.0 mmol) in dichloromethane (50 ml) was added and the reaction stirred at −20° C. for 15 minutes. Triethylamine (4.6 ml, 33 mmol) was added and the reaction stirred for 90 minutes, warming slowly to room temperature. The mixture was diluted with dichloromethane and washed with water. The organic layer was dried (MgSO$_4$) and concentrated in vacuo. The residue was purified by flash column chromatography on silica gel, eluting with 5% methanol/dichloromethane to give the title compound (2.8 g, 80%).

$\delta_H$ (400 MHz, CDCl$_3$): 7.88–7.86 (2H, m), 7.66–7.64 (1H, m), 7.58–7.54 (2H, m), 2.97 (2H, s), 2.63 (2H, t, J 5.5 Hz), 2.42–2.33 (4H, m), 1.97–1.91 (2H, m), 1.75–1.71 (2H, m), 1.60–1.52 (2H, m), 1.29 (6H, s); m/z (ES$^+$) 324 (M+H)$^+$.

Example 271

1-(4-Benzenesulfonyl-4-methylpentyl)-(3Z)-3-benzylidenepiperidine

A solution of diethyl benzylphosphonate (0.53 ml, 2.54 mmol) and 1-(4-benzenesulfonyl-4-methylpentyl)-3-piperidinone (0.7 g, 2.17 mmol) in 1,3-dimethylimidazolidin-2-one (5 ml) was added dropwise to a stirred slurry of sodium hydride (60% dispersion in mineral oil, 117 mg, 2.93 mmol) in 1,3-dimethylimidazolidin-2-one (3 ml). The reaction was stirred for 30 minutes then quenched by the addition of water. The mixture was extracted with dichloromethane. The combined organic layers were dried (MgSO$_4$) and concentrated in vacuo. The residue was purified by flash column chromatography on silica gel, eluting with 20–75% ethyl acetate/chloroform, followed by preparative HPLC.

$\delta_H$ (400 MHz, MeOD-d$_4$): 7.86–7.84 (2H, m), 7.77–7.73 (1H, m), 7.66–7.62 (2H, m), 7.40–7.36 (2H, m), 7.32–7.28 (1H, m), 7.22 (2H, d, J 7 Hz), 6.82 (1H, s), 4.29 (1H, d, J 13 Hz), 3.78–3.72 (1H, m), 3.64–3.61 (1H, m), 3.22–3.15 (1H, m), 3.10–3.07 (2H, m), 2.62–2.51 (2H, m), 2.15–2.2.09 (1H, m), 1.96–1.89 (1H, m), 1.83–1.75 (1H, m), 1.70–1.62 (1H, m), 1.35–1.25 (2H, m), 1.20 (6H, d, J 8.7 Hz); m/z (ES$^+$) 398 (M+H)$^+$.

Example 272

1-(4-Benzenesulfonyl-4-methylpentyl)-3-(1-benzyl-1-methylamino)piperidine 1-(4-Benzenesulfonyl-4-methylpentyl)-3-piperidinone (0.88 g, 2.7 mmol), N-benzyl-N-methylamine (0.39 ml, 3.0 mmol), sodium triacetoxyborohydride (0.8 g, 3.8 mmol) and glacial acetic acid (0.18 ml) were combined in 1,2-dichloroethane (10 ml) and stirred at room temperature for 3 hours. The reaction was quenched by the addition of saturated aqueous sodium hydrogen carbonate solution and extracted with dichloromethane. The combined organic layers were dried (MgSO$_4$) and concentrated in vacuo. The residue was purified by flash column chromatography on silica gel, eluting with 150:8:1 dichloromethane:methanol:ammonia, to give the title compound (870 mg, 75%).

$\delta_H$ (400 MHz, CDCl$_3$): 7.88–7.86 (2H, m), 7.66–7.63 (1H, m), 7.57–7.53 (2H, m), 7.30 (4H, d, J 4.3 Hz), 7.25–7.20 (1H, m), 3.59 (2H, s), 3.03–3.00 (1H, m), 2.82–2.79 (1H, m), 2.70–2.63 (1H, m), 2.31 (2H, dt, J 2.5, 7.5 Hz), 2.21 (3H, s), 1.98–1.49 (9H, m), 1.30 (6H, s), 1.33–1.23 (1H, m); m/z (ES$^+$) 429 (M+H)$^+$.

Description 60

1-(4-Benzenesulfonyl-4-methylpentyl)-3-(methylamino)piperidine

A mixture of 1-(4-benzenesulfonyl-4-methylpentyl)-3-(1-benzyl-1-methylamino)piperidine (1 g, 2 mmol) and palladium hydroxide (120 mg) in ethanol (20 ml) and concentrated hydrochloric acid (1 ml) was hydrogenated in a Parr apparatus at 50–55 psi for 3 hours. The mixture was filtered through Celite and the filtrate concentrated in vacuo. The residue was partitioned between saturated aqueous sodium hydrogen carbonate solution and dichloromethane. The aqueous layer was extracted with dichloromethane. The combined organic layers were dried (MgSO$_4$) and concentrated in vacuo. The residue was purified by flash column chromatograhpy on silica gel, eluting with 120:8:1 dichloromethane:methanol:ammonia, to give the title compound (35 mg, 5%).

$\delta_H$ (360 MHz, CDCl$_3$): 7.89–7.86 (2H, m), 7.68–7.64 (1H, m), 7.56 (2H, t, J 7.6 Hz), 2.81–2.77 (1H, m), 2.63–2.57 (2H, m), 2.45 (3H, s), 2.33–2.29 (2H, m), 2.12–1.80 (3H, m), 1.73–1.67 (3H, m), 1.59–1.51 (3H, m), 1.29 (6H, s), 1.29–1.25 (1H, m); m/z (ES$^+$) 339 (M+H)$^+$.

Example 273

1-(4-Benzenesulfonyl-4-methylpentyl)-3-(1-methyl-1-benzenesulfonylamino)piperidine Benzenesulfonyl chloride (90 μL, 0.7 mmol) was added to a solution of 1-(4-benzenesulfonyl-4-methylpentyl)-3-(methylamino)piperidine (0.22 g, 0.65 mmol) and triethylamine (180 μL, 1.3 mmol) in dichloromethane (5 ml). The reaction was stirred at room temperature for 30 minutes. The mixture was diluted with dichloromethane and washed with water (×2). The organic layer was dried (MgSO$_4$) and concentrated in vacuo. The residue was purified by flash column chromatography on silica gel, eluting with 2–5% methanol/dichloromethane, to give the title compound (220 mg, 76%).

$\delta_H$ (400 MHz, CDCl$_3$): 7.89–7.86 (2H, m), 7.83–7.81 (2H, m), 7.68–7.64 (1H, m), 7.59–54 (3H, m), 7.52–7.48 (2H, m), 3.93–3.86 (1H, m), 2.79 (3H, s), 2.76–2.72 (1H, m), 2.65–2.62 (1H, m), 2.31–2.23 (1H, m), 2.20–2.13 (1H, m), 1.82 (1H, t, J 11 Hz), 1.75–1.61 (5H, m), 1.48–1.42 (3H, m), 1.32–1.22 (1H, m), 1.28 (6H, s); m/z (ES$^+$) 479 (M+H)$^+$.

Example 274

N-[1-(4-Benzenesulfonyl-4-methylpentyl)piperidin-3-yl]-N-methylbenzamide

Benzoyl chloride (49 mg, 0.35 mmol) was added to a stirred solution of the product of Description 60 (100 mg, 0.3 mmol) and triethylamine (70 mg, 0.7 mmol) in dichloromethane (10 ml). After twenty minutes the mixture was partitioned between dichloromethane and water. The organic layer was separated, dried and concentrated in vacuo. Chromatography on silica gel eluting with methanol/dichloromethane afforded the title compound (113 mg, 86%).

$\delta_H$ (400 MHz, CDCl$_3$): 8.06–7.27 (10H, m), 3.15–1.41 (18H, m), 1.28 (6H, s); m/z (ES$^+$) 443 (M+H)$^+$.

Example 275

1-(4-Benzenesulfonyl-4-methylpentyl)-3-prop-1-ynylpiperidine n-Butyllithium (0.44 ml, 0.68 mmol) was added to a −78° C. stirred suspension of Example 115 (0.1 g, 0.27 mmol) in tetrahydrofuran (5 ml). After thirty minutes, iodomethane (0.19 g, 1.35 mmol) was added. The reaction mixture was stirred at this temperature for two hours then quenched by addition of a saturated solution of ammonium chloride. The mixture was partitioned between ethyl acetate and water. The organic layer was separated, dried and concentrated in vacuo. Chromatography on silica gel eluting with methanol/dichloromethane afforded the title compound (62 mg, 66%).

$\delta_H$ (400 MHz, CDCl$_3$): 7.87 (2H, m), 7.65 (1H, m), 7.66 (2H, m), 7.55 (2H, m), 2.85 (1H, m), 2.70 (1H, m), 2.44 (1H, m), 2.29 (2H, s), 2.01–1.82 (3H, m), 1.78 (3H, d, J 2.3 Hz), 1.72–1.48 (6H, m), 1.31 (6H, s); m/z (ES$^+$) 348 (M+H)$^+$.

Example 276

1-(4-Benzenesulfonyl-4-methylpentyl)-3-(phenylethynyl)piperidine

A mixture of 1-(4-benzenesulfonyl-4-methylpentyl)-3-ethynylpiperidine (0.33 g, 1.0 mmol), iodobenzene (80 μL, 0.7 mmol), dichlorobis(triphenylphosphine)palladium(II) (35 mg, 0.05 mmol) and copper(I) iodide (6 mg, 0.03 mmol) in diisopropylamine (5 ml) was stirred at 70° C. for 2 hours. The reaction mixture was filtered through Celite, washing with dichloromethane (50 ml). The filtrate was concentrated in vacuo and the residue purified by flash column chromatography on silica gel, eluting with 2% methanol/dichloromethane, followed by an SCX cartridge and finally preparative thin layer chromatography, eluting with 7% methanol/dichloromethane, to give the title compound. The hydrochloride salt (63 mg, 14%) was obtained by treatment with ethereal hydrogen chloride and crystallisation from ethanol/diethyl ether.

$\delta_H$ (400 MHz, CDCl$_3$): 7.89–7.86 (1H, m), 7.70–7.63 (3H, m), 7.57–7.53 (2H, m), 7.49–7.44 (2H, m), 7.40–7.37 (1H, m), 7.28–7.26 (1H, m), 3.01–2.99 (1H, m), 2.78–2.68 (2H, m), 2.35–2.31 (2H, m), 2.09–1.96 (3H, m), 1.73–1.69 (3H, m), 1.59–1.54 (2H, m), 1.46–1.36 (1H, m), 1.30 (6H, s), 1.30–1.25 (1H, m); m/z (ES$^+$) 410 (M+H)$^+$.

Description 61

1-(4-Benzenesulfonyl-4-methylpentyl)piperidine-3-carboxylic acid amide

The title compound was prepared from the product of Description 10 and piperidine-3-carboxylic acid amide as described in Example 1.

$\delta_H$ (400 MHz, CDCl$_3$): 7.87 (2H, m), 7.67 (1H, m), 7.57 (2H, m), 5.36 (2H, br), 2.78 (1H, br), 2.65 (1H, br), 2.49 (1H, m), 2.36 (1H, m), 2.33 (2H, t, J 7.0 Hz), 2.17 (1H, m), 1.93–1.48 (8H, m), 1.30 (3H, s), 1.29 (3H, s); m/z (ES$^+$) 353 (M+H)$^+$.

Example 277

1-(4-Benzenesulfonyl-4-methylpentyl)-3-(4-methyloxazol-2-yl)piperidine hydrochloride A solution of hydrogen chloride in diethyl ether (1M, 1.25 ml, 1.25 mmol) was added to a stirred mixture of the product of Description 61 (147 mg, 0.416 mmol), chloroacetone (1.0 ml, 12.5 mmol) and N,N-dimethylformamide (4 ml). The mixture was stirred at 120° C. overnight. N,N-Dimethylformamide was removed by distillation under vacuum. The residue was purified by chromatography on silica gel (dichloromethane:methanol) to give the title amine. The hydrochloride salt was prepared by treatment of the title amine with ethereal HCl.

$\delta_H$ (400 MHz, MeOH-d$_4$): 7.89 (2H, m), 7.76 (1H, m), 7.66 (3H, m), 4.04–3.82 (1H, m), 3.64 (1H, m), 3.57–3.36 (1H, m), 3.25–3.11 (3H, m), 3.01 (1H, dt, J 3.5 and 12.1 Hz), 2.29 (1H, d, J 13.3 Hz), 2.15 (3H, s), 2.22–1.66 (7H, m), 1.32 (6H, s); m/z (ES$^+$) 391 (M+H)$^+$.

Example 278 and 279

1-(4-Benzenesulfonyl-4-methylpentyl)-3-phenylsulfanylpiperidine hydrochloride and 1-(4-benzenesulfonyl-4-methyl-pentyl)-2-phenylsulfanylmethylpyrrolidine hydrochloride Methanesulphonic anhydride (0.25 g, 1.43 mmol) was added to a stirred mixture of the product of Description 57 (160 mg, 0.49 mmol), triethylamine (0.30 ml, 2.16 mmol) and dichloromethane (3 ml) at 0° C. The mixture was stirred for 1 hour before addition of benzenethiol sodium salt (600 mg, 4.5 mmol) and methanol (1 ml). The mixture was slowly warm up to room temperature and stirred overnight. Solid NH$_4$Cl was added and the resulting mixture was stirred for 30 min. and filtered through a pad of silica (dichloromethane:methanol). The residue was purified by chromatography on silica gel (dichloromethane:methanol) to give the title products. Hydrochlorides were prepared by treatment of the title amines with ethereal HCl.

Example 278

1-(4-Benzenesulfonyl-4-methylpentyl)-3-phenylsulfanylpiperidine hydrochloride $\delta_H$ (400 MHz, MeOH-d$_4$): 7.87 (2H, m), 7.75 (1H, m), 7.65 (2H, m), 7.51 (2H, m), 7.37 (3H, m), 3.58 (2H, m), 3.44 (1H, m), 3.20–3.00 (2H, m), 2.97–2.79 (2H, m), 2.24–1.60 (7H, m), 1.49 (1H, m), 1.27 (6H, s); m/z (ES$^+$) 418 (M+H)$^+$.

Example 279

1-(4-Benzenesulfonyl-4-methylpentyl)-2-phenylsulfanylmethylpyrrolidine hydrochloride $\delta_H$ (400 MHz, MeOH-d$_4$): 7.88 (2H, d, J 7.3 Hz), 7.76 (1H, t, J 7.3 Hz), 7.66 (2H, t, J 7.6 Hz), 7.47 (2H, d, J 7.9 Hz), 7.36 (2H, t, J 7.3 Hz), 7.28 (H, t, J 7.3 Hz), 3.72 (1H, m), 3.57 (1H, m), 3.48 (1H, dd, J 6.7 and 14.0 Hz), 3.31 (1H, m), 3.19 (1H, m), 3.02 (1H, m), 2.37 (1H, m), 2.17–1.61 (7H, m), 1.26 (6H, s); m/z (ES$^+$) 418 (M+H)$^+$.

Example 280

N-[1-(4-Benzenesulfonyl-4-methylpentyl)piperidin-3-ylmethyl]-N-methyl-benzeneamine Sodium triacetoxyborohydride (104 mg, 0.5 mmol) was added to a stirred mixture of the product of Description 53 and N-methylaniline (140 mg, 0.14 ml, 1.3 mmol) and dichloromethane (2 ml) at room temperature. The mixture was stirred overnight and quenched with sat. aqueous NaHCO$_3$. The organic phase was extracted into dichloromethane, dried (Na$_2$SO$_4$) and concentrated. The residue was purified by chromatography on silica gel (dichloromethane:methanol) to give the title product.

$\delta_H$ (400 MHz, CDCl$_3$): 7.86 (2H, m), 7.63 (1H, m), 7.53 (2H, m), 7.20 (2H, m), 6.67 (3H, m), 3.21 (1H, dd, J 7.8 and 14.4 Hz), 3.12 (1H, dd, J 6.7 and 14.4 Hz), 2.91 (3H, s), 2.76 (2H, m), 2.28 (2H, br t, J 7.0 Hz), 2.06 (1H, m), 1.96 (1H, br t, J 9.8 Hz), 1.83–1.61 (6H, m), 1.60–1.45 (2H, m), 1.28 (6H, s); m/z (ES$^+$) 429 (M+H)$^+$.

Example 281

N-[1-(4-Benzenesulfonyl-4-methylpentyl)piperidin-3-ylmethyl]-N-benzyl-methylamine trifluoroacetate Sodium triacetoxyborohydride (104 mg, 0.5 mmol) was added to a stirred solution of the product of Description 53 (90 mg, 0.26 mmol) and N-methylbenzylamine (0.15 ml, 1.17 mmol) in dichloromethane (2 ml) at room temperature. The mixture was stirred overnight and quenched with sat. aqueous NaHCO$_3$. The organic phase was extracted into dichloromethane, dried (Na$_2$SO$_4$) and concentrated. The residue was purified by chromatography on silica gel (dichloromethane:methanol) to give the title product (50 mg, 34%). The hydrochloride salt was prepared by treatment of the title amine with ethereal HCl.

$\delta_H$ (400 MHz, MeOH-d$_4$): 7.88 (2H, m), 7.76 (1H, t, J 7.4 Hz), 7.65 (2H, t, J 7.4 Hz), 7.54 (2H, m), 7.49 (3H, m), 3.71 (1H, m), 3.56 (1H, m), 3.39–2.98 (3H, m), 2.94–2.79 (1H, m), 2.86 (3H, s), 2.68 (1H, m), 2.46 (1H, br), 2.04–1.79 (4H, m), 1.78–1.67 (2H, m), 1.30 (6H, s); m/z (ES$^+$) 443 (M+H)$^+$.

Description 62

3-[1-(4-Benzenesulfonyl-4-methylpentyl)piperidin-3-ylmethyl]-indole-1-carboxylic acid tert-butyl ester The title compound was prepared from the product of Description 10 and 3-piperidin-3-ylmethyl-indole-1-carboxylic acid tert-butyl ester as described in Example 1.

$\delta_H$ (400 MHz, MeOH-d$_4$): 8.09 (1H, d, J 8.2 Hz), 7.83 (2H, d, J 7.4 Hz), 7.69 (1H, t, J 7.4 Hz), 7.59 (2H, t, J 8.2 Hz), 7.53 (1H, d, J 7.4 Hz), 7.37 (1H, s), 7.27 (1H, t, J 7.0 Hz), 7.20 (1H, t, J 7.4 Hz), 3.35 (1H, s), 2.85 (2H, m), 2.57 (2H, m), 2.27 (2H, m), 1.93 (2H, m), 1.82–1.44 (7H, m), 1.65 (9H, s), 1.21 (3H, s), 1.19 (3H, s), 0.76 (1H, dq, J 3.5, 12.1 Hz); m/z (ES$^+$) 539 (M+H)$^+$.

Example 282

3-[1-(4-Benzenesulfonyl-4-methylpentyl)piperidin-3-ylmethyl]-1H-indole hydrochloride A mixture of the product of Description 62 (80 mg, 0.15 mmol), dichloromethane (1 ml) and trifluoroacetic acid (0.2 ml) was kept at room temperature overnight and concentrated in vacuo. The residue was treated with 2M ammonia in methanol and purified by chromatography on silica gel (dichloromethane:methanol). The hydrochloride salt was prepared by treatment of the title amine with ethereal HCl.

$\delta_H$ (400 MHz, MeOH-d$_4$): 7.85 (2H, d, J 7.6 Hz), 7.68 (1H, t, J 7.3 Hz), 7.64 (1H, d, J 7.9 Hz), 7.59 (2H, t, J 7.3 Hz), 7.38 (2H, d, J 8.2 Hz), 7.14 (1H, s), 7.11 (2H, t, J 7.9 Hz), 7.03 (1H, t, J 7.3 Hz), 3.62 (2H, m), 3.45 (1H, br t, J 12.0 Hz), 3.02 (2H, br t, J 7.6 Hz), 2.92 (2H, br t, J 11.7 Hz), 2.12 (1H, br d, J 12.6 Hz), 2.04 (2H, m), 2.00–1.66 (3H, m), 1.71 (2H, t, J 7.9 Hz), 1.27 (6H, s); m/z (ES$^+$) 439 (M+H)$^+$.

Description 63

3-[1-(4-Benzenesulfonyl-4-methylpentyl)piperidin-3-yl]-indole-1-carboxylic acid tert-butyl ester The title compound was prepared from the product of Description 10 and 3-piperidin-3-yl-indole-1-carboxylic acid tert-butyl ester oxalate salt as described in Example 1.

$\delta_H$ (400 MHz, MeOH-d$_4$): 8.09 (1H, d, J 8.2 Hz), 7.85 (2H, m), 7.68 (1H, m), 7.59 (2H, m), 7.55 (2H, d, J 7.8 Hz), 7.38 (1H, s), 7.27 (1H, m), 7.20 (1H, m), 3.10 (1H, d, J 11.3 Hz), 3.03 (1H, m), 2.95 (1H, d, J 11.3 Hz), 2.32 (2H, t, J 7.8 Hz), 2.06–1.94 (3H, m), 1.82–1.39 (8H, m), 1.65 (9H, s), 1.26 (3H, s), 1.25 (3H, s); m/z (ES$^+$) 525 (M+H)$^+$.

Example 283

3-[1-(4-Benzenesulfonyl-4-methylpentyl)piperidin-3-yl]-1H-indole

The title compound was prepared from the product of Description 63 as described in Example 282.

$\delta_H$ (400 MHz, MeOH-d$_4$): 7.85 (2H, d, J 7.3 Hz), 7.72 (1H, t, J 7.3 Hz), 7.61 (2H, t, J 7.3 Hz), 7.53 (1H, d, J 7.9 Hz), 7.35 (2H, d, J 8.2 Hz), 7.09 (2H, t, J 7.3 Hz), 7.08 (1H, s), 7.01 (1H, t, J 7.3 Hz), 3.43 (2H, br t, J 14.0 Hz), 2.93 (2H, m), 3.73 (3H, m), 2.58 (2H, t, J 11.7 Hz), 2.21 (1H, br), 1.95–1.56 (7H, m), 1.24 (3H, s), 1.23 (3H, m); m/z (ES$^+$) 425 (M+H)$^+$.

Example 284

1-(4-Benzenesulfonyl-4-methylpentyl)-3-(1,1-difluoroethyl)piperidine

A mixture of Example 206 (150 mg, 0.42 mmol) and diethylaminosulphur trifluoride (0.21 ml, 1.68 mmol) in dichloromethane (2.5 ml) was stirred at room temperature for 20 hours. The reaction mixture was carefully poured onto ice-cold saturated aqueous sodium hydrogen carbonate solution and extracted with ethyl acetate. The combined organic layers were dried (MgSO$_4$) and concentrated in vacuo. The residue was purified by preparative thin layer chromatography, eluting with 5% methanol/dichloromethane, followed by preparative HPLC to give the title compound as the trifluoroacetate salt.

$\delta_H$ (400 MHz, MeOH-d$_4$): 7.89 (2H, m), 7.76 (1H, m), 7.66 (2H, m), 3.71–3.55 (2H, m), 3.15 (2H, m), 2.99–2.83 (2H, m), 2.40 (1H, m), 2.14–1.72 (6H, m), 1.65 (3H, t, J 19.3 Hz), 1.48 (1H, m), 1.31 (6H, s); m/z (ES$^+$) 374 (M+H)$^+$.

Description 64

1-(4-Benzenesulfonyl-4-methylpentyl)piperidine-3-carbaldehyde oxime

The title compound was prepared as described in Example 209 and 210 from hydroxylamine and the product of Description 53.

$\delta_H$ (400 MHz, CDCl$_3$): 7.87 (2H, m), 7.65 (1H, m), 7.47 (2H, m), 2.91–2.65 (2H, m), 2.54–2.42 (2H, m), 2.31 (2H, m), 1.98 (1H, m), 1.77–1.48 (8H, m), 1.29 (6H, s).

Example 285

1-(4-Benzenesulfonyl-4-methylpentyl)-3-(5-methyl-isoxazol-3-yl)piperidine

A solution of the product of Description 64 (151 mg, 0.43 mmol) in N,N-dimethylformamide (10 ml) was cooled to 0° C. N-bromosuccinimide (115 mg, 0.65 mmol) in N,N-dimethylformamide (5 ml) was added dropwise. The reaction was stirred for 1 hour then treated with triethylamine (90 μL, 0.65 mmol). Propyne gas was bubbled through the solution until colour was discharged. The reaction was stirred for 18 hours at room temperature. The mixture was concentrated in vacuo and the residue purified by preparative thin layer chromatography, eluting with 5% methanol/dichloromethane.

$\delta_H$ (400 MHz, CDCl$_3$): 7.87 (2H, m), 7.65 (1H, m), 7.55 (2H, m), 5.86 (1H, s), 3.10–2.78 (3H, m), 2.38 (3H, s), 2.34 (2H, m), 2.16–1.92 (3H, m), 1.42 (1H, dq, J 4.6 and 11.7 Hz), 1.29 (6H, s); m/z (ES$^+$) 391 (M+H)$^+$.

Example 286

1-(4-Benzenesulfonyl-4-methylpentyl)-3-(5,5-dimethyl-4,5-dihydroisoxazol-3-yl)piperidine The title compound was prepared as described in Example 285 from isobutylene and the product of Description 64. m/z (ES$^+$) 407 (M+H)$^+$.

Example 287

1-(4-Benzenesulfonyl-4-methylpentyl)-3-(oxazol-5-yl)piperidine

A solution of the product of Description 53 (67 mg, 0.2 mmol) and (p-tolylsulfonyl)methyl isocyanide (39 mg, 0.2 mmol) in methanol (10 ml) was treated with potassium carbonate (28 mg, 0.2 mmol) and heated at reflux for 18 hours. The reaction mixture was concentrated in vacuo and the residue partitioned between dichloromethane and water. The combined organic layers were purified by preparative thin layer chromatography, eluting with 10% methanol/dichloromethane, followed by crystallisation from acetonitrile/diethyl ether to give the title compound as the hydrochloride salt.

$\delta_H$ (400 MHz, MeOH-d$_4$): 8.18 (1H, s), 7.89 (2H, m), 7.76 (1H, m), 7.66 (2H, m), 7.05 (1H, s), 3.84–3.55 (2H, m), 3.23–2.90 (4H, m), 2.26–1.67 (8H, m), 1.31 (6H, s); m/z (ES$^+$) 377 (M+H)$^+$.

Description 65

1-(4-Benzenesulfonyl-4-methyl-pentyl)piperidine-3-carbonitrile

A solution of product of Description 61 (600 mg, 1.7 mmol) in tetrahydrofuran (15 ml) was treated with pyridine (0.275 ml, 3.4 mmol) followed by trifluoroacetic anhydride (0.285 ml, 2.04 mmol) and stirred for 1 hour. The mixture was diluted with water and extracted with ethyl acetate. The organics were collected, dried (magnesium sulfate) and concentrated in vacuo. The aqueous extracts were basified, extracted with dichloromethane and the organics collected. These were concentrated in vacuo, azeotroping with toluene and the residue was purified by preparative TLC to give the title compound.

$\delta_H$ (400 MHz, CDCl$_3$): 7.87 (2H, m), 7.66 (1H, m), 7.56 (2H, m), 3.01–2.28 (6H, m), 2.02–1.56 (8H, m), 1.29 (6H, s), 1.27 (1H, m); m/z (ES$^+$) 391 (M+H)$^+$.

Example 288

1-(4-Benzenesulfonyl-4-methylpentyl)-3-(2-methyl-2H-tetrazol-5-yl)piperidine

A solution of the product of Description 65 (100 mg, 0.30 mmol) and azidotributyltin (904 μL, 3.3 mmol) in toluene (1 ml) was heated at 80° C. for 36 hours in a sealed tube. The reaction mixture was treated with 6N aqueous hydrochloric acid (8 ml) and tetrahydrofuran (3 ml) and stirred at room temperature for 18 hours. The mixture was extracted with ethyl acetate and the aqueous layer concentrated in vacuo. The residue (60 mg, 0.15 mmol) was treated with potassium carbonate (100 mg, 0.75 mmol) and acetonitrile (5 ml). The mixture was stirred at 60° C. for 18 hours. The reaction mixture was diluted with water and extracted with ethyl acetate. The combined organic layers were concentrated in vacuo and the residue purified by preparative thin layer chromatography, eluting with 5% methanol/dichloromethane, followed by crystallisation from ethyl acetate to give the title compound as the hydrochloride salt.

$\delta_H$ (400 MHz, MeOH-d$_4$): 7.89 (2H, m), 7.77 (1H, m), 7.66 (2H, m), 4.35 (3H, s), 3.97–3.37 (3H, m), 3.26–2.90 (4H, m), 2.38–1.70 (8H, m), 1.31 (6H, s); m/z (ES$^+$) 377 (M+H)$^+$.

Example 289

1-(4-Benzenesulfonyl-4-methylpentyl)-3-(1H-imidazol-2-yl)piperidine

Ammonia was bubbled through the mixture of the product of Description 53 (220 mg, 0.65 mmol) and glyoxal 40% in water (1 ml) and ethanol (10 ml) for 10 minutes. The mixture was stirred at room temperature for 2 hours and concentrated in vacuo. The residue purified by prep. TLC eluting with 5% methanol/dichloromethane. The product was isolated as the dihydrochloride salt.

$\delta_H$ (400 MHz, MeOH-d$_4$): 7.89 (2H, m), 7.76 (1H, m), 7.66 (2H, m), 7.53 (2H, m), 5.86 (1H, s), 3.89–3.56 (3H, m), 3.28–2.96 (4H, s), 2.35–1.69 (8H, m), 1.31 (6H, s); m/z (ES$^+$) 376 (M+H)$^+$.

Example 290

1-(4-Benzenesulfonyl-4-methylpentyl)-3-ethynyl-4-methylpiperidine

A solution of Example 129 (0.35 g, 0.85 mmol) in dichloromethane (20 ml) was cooled to −78° C. and treated with diisobutylaluminium hydride (1M in dichloromethane, 2.125 ml, 2.125 mmol) dropwise. The mixture was quenched with 0.4 ml of water at this temperature and the mixture was filtered through the pad of Celite. The mixture was concentrated in vacuo. The residue was dissolved in methanol (15 ml) and treated with potassium carbonate (586 mg, 4.25 mmol) and stirred for 1 hour. The mixture was treated with (1-diazo-2-oxopropyl)phosphonate (410 mg, 2.1 mmol) and left overnight, concentrated in vacuo and purified by prep TLC to give the title compound.

$\delta_H$ (400 MHz, CDCl$_3$): 7.87 (2H, m), 7.65 (1H, m), 7.66 (2H, m), 7.55 (2H, m), 3.02 (1H, m), 2.83 (1H, m), 2.11 (1H, m), 3.89–3.56 (3H, m), 2.07 (1H, t, J 2.3 Hz), 1.93 (2H, t, J 11.0 Hz), 1.73–1.62 (3H, m), 1.59–1.48 (2H, m), 1.29 (6H, s), 1.22 (1H, m), 1.08 (3H, d, J 6.3 Hz); m/z (ES$^+$) 348 (M+H)$^+$.

Description 66

4-Methyl-4-(phenylsulfonyl)butyne (Phenylsulfonyl)propyne (0.82 g, 4.5 mmol), cesium carbonate (4.4 g, 13.5 mmol) and methyl iodide (1.4 ml) were suspended in acetonitrile (20 ml) and stirred for 12 h. Additional aliquots of methyl iodide (3×1.4 ml) and cesium carbonate (2×4.4 g) were added and the mixture was stirred for an additional 12 h. The mixture was diluted with ethyl acetate and filtered to remove inorganics. The filtrate was concentrated and purified on silica gel using 10–25% ethyl acetate in i-hexane as eluant. This afforded the product as a white crystalline solid (400 mg, 43%).

$\delta_H$ (400 MHz, CDCl$_3$): 8.01–7.98 (2H, m), 7.70–7.60 (1H, m), 7.59–7.54 (2H, m), 2.45 (1H, s), 1.62 (6H, s).

Example 291

2-[4-Methyl-4-(phenylsulfonyl)pent-2-ynyl]-5-phenyl-2-azabicyclo[2.2.1]heptane A solution of 4-methyl-4-(phenylsulphonyl)butyne (208 mg, 1 mmol), 5-phenyl-2-azabicyclo[2.2.1]heptane (207 mg, 1.2 mmol), and paraformaldehyde (36 mg, 1.2 mmol) in dioxane (3 ml) was degassed three times. Cuprous chloride (10 mg) was added and the mixture was heated under reflux conditions for 1 h. The mixture was cooled and evaporated in vacuo. The residue was purified by chromatography on silica using 1–7% methanol in dichloromethane. The resulting brown oil was re-purified on alumina (grade III) using 25–50% ethyl acetate in i-hexane as eluant. The resulting oil was dissolved in ethyl acetate and ethereal hydrogen chloride added dropwise to give a white crystalline solid.

$\delta_H$ (400 MHz, MeOH-d$_4$): 8.02–8.00 (2H, m), 7.85–7.80 (1H, m), 7.73–7.69 (2H, m), 7.35–7.26 (4H, m), 7.25–7.21 (1H, m), 4.22 (1H, d, J 16.5 Hz), 4.19 (1H, s), 4.11 (2H, d, J 16.5 Hz), 3.4–3.2 (2H, br m), 3.17 (1H, dd, J 5.8 and 8.8 Hz), 2.85 (1H, s), 2.46 (1H, dd, J 9.4 and 14.3 Hz), 2.01–2.10 (3H, m),1.62 (6H, s); m/z (ES$^+$) 218 ([M-$^t$Bu]H$^+$).

Descriptions 67–70 record the synthesis of various amines used in the synthesis of compounds of the invention.

Description 67

4-Methylpiperidine-3-carboxylic acid ethyl ester hydrochloride

3-Bromo-4-methyl pyridine (10 g, 58.4 mmol), bis(tri-o-tolylphosphine)palladium(II) chloride (2.7 g, 3.5 mmol), triethylamine (3.0 g, 4.1 ml, 29.2 mmol) were stirred at 70° C. and carbon monoxide was continuously bubbled through the mixture for a further 10 hours. The mixture was concentrated in vacuo, and the residue distilled at 75–95° C. (7 mbar). Fraction containing product were combined dissolved in ethanol (5 ml), acidified and treated with platinum oxide (0.67 g, 2.9 mmol) and hydrogenated on the Parr apparatus. The mixture was filtered through Celite and the filtrate treated with excess HCl. This was concentrated in vacuo, to afford the crude product that was crystallised as the HCl salt from ethyl acetate. Solid was filtered and the mother liquors were concentrated to give the title product.

$\delta_H$ (400 MHz, MeOH-d$_4$): 3.38–3.26 (3H, m), 2.97 (2H, dt, J 3.2 and 12.9 Hz), 1.89 (2H, m), 1.72 (1H, m), 1.43–1.30 (2H, m), 1.01 (3H, d, J 6.7 Hz).

Description 68

5-(4-Fluorophenyl)-2-azabicyclo[2.2.1]heptane (isomer B) and 6-(4-fluorophenyl)-2-azabicyclo[2.2.1]heptane (isomer A)

A solution of 2-tert-butoxycarbonyl-2-azabicyclo[2.2.1]hept-5-ene (3.9 g, 0.02 mol), 1-fluoro-4-iodobenzene (4.6 ml, 0.04 mol) and piperidine (7 ml, 0.07 mol) in N,N-dimethylformamide (4 ml) was degassed three times. Tetrakis(triphenylphosphine)palladium(0) (1 g, 0.086 mmol, 4 mol%) was added followed by formic acid (2.3 ml, 0.06 mol) dropwise. The reaction was heated at 70° C. for 4 hours. The cooled reaction mixture was diluted with water (50 ml) and extracted with ethyl acetate. The combined organic layers were washed with brine and evaporated in vacuo. The residue was purified by flash column chromatography on silica gel, eluting with 10–20% ethyl acetate/i-hexane, to give a 1:1 mixture of the Boc-derivatives of the title compounds (4.3 g, 75%), m/z (ES+) 236 ([M-$^t$Bu]+H$^+$).

This mixture was dissolved in methanolic hydrogen chloride (2M) and stirred overnight. The solution was evaporated, basified (Na$_2$CO$_3$), and extracted into ethyl acetate. The organic extract was dried, brine and MgSO$_4$, and evaporated. The mixture was separated on silica gel using 1–10% methanolic ammonia in dichloromethane to elute isomer A and 10–50% methanolic ammonia in dichloromethane to elute isomer B.

Isomer A: $\delta_H$ (400 MHz) 7.17–7.12 (2H, m), 6.97 (2H, t, J 8.7 Hz), 3.53 (1H, s), 3.09 (1H, t, J 7.5 Hz), 2.99 (1H, dt, J 9.6 and 3.2 Hz), 2.75 (1H, d, J 9.6 Hz), 2.57 (1H, br s), 1.93 (1H, m), 1.78 (1H, m), 1.65 (1H, d, J 10.2 Hz), 1.53 (1H, dt, J 10.2, 1.8 Hz); m/z (ES+) 192 (M+H)$^+$.

Isomer B: $\delta_H$ (400 MHz, CDCl$_3$): 7.28 (1H, s), 7.19–7.14 (2H, m), 7.04–6.95 (2H, m), 4.05 (1H, s), 3.22 (1H, dd, J 3.5and 10.6 Hz), 3.13–3.07 (2H, m), 2.73 (1H, d, J 2.3 Hz), 2.51–2.45 (1H, m), 1.90–1.77 (3H, m); m/z (ES+) 192 (M+H)$^+$.

Description 69

(1R,4R,5R)-5-Phenyl-2-azabicyclo[2.2.1]heptane and (1S,4S,6R)-6-phenyl-2-azabicyclo[2.2.1]heptane N-[(R)-2-Hydroxy-1-methoxycarbonylethyl]-(1S,4R)-2-azabicyclo[2.2.1]hept-5-ene (3.5 g, 0.018 mol) and triphenylphosphine (4.7 g, 0.018 mol) were dissolved in dichloromethane (50 ml) and diethyl azodicarboxylate was added dropwise. The mixture was stirred for 3 days. Hydrochloric acid (20 ml, 2M) was added and the acidic phase was washed with ether, then basified with sodium hydroxide (25 ml, 2M) and this was extracted with ether. The ethereal extract was treated with di(t-butyl)dicarbonate (3.9 g, 0.018 mol) and stirred for 12 h. The solution was concentrated in vacuo and the residue was purified by column chromatography on silica gel using 5–10% ether in i-hexane as eluant to afford (1S,4R)-2-tert-butoxycarbonyl-2-azabicyclo[2.2.1]hept-5-ene as a colourless oil (300 mg, 8%) which crystallised in the freezer.

$\delta_H$ (400 MHz, CDCl$_3$): 6.39–6.37 (2H, m), 6.27 (3H, s), 4.71 (0.5H, s), 4.57 (0.5H, br s), 4.57 (0.5H, br s), 3.31 (2H, dd, J 2.9 and 9.2 Hz), 3.15 (1H, s), 2.65–2.56 (1H, m), 1.57–1.52 (2H, m), 1.44 (9H, s).

A solution of the above product (300 mg, 1.5 mmol), iodobenzene (630 mg, 3.0 mmol) and piperidine (0.5 ml, 5.25 mmol) in N,N-dimethylformamide (4 ml) was degassed three times.

Tetrakis(triphenylphosphine)palladium(0) (80 mg, 0.075 mmol) was added followed by formic acid (0.17 ml, 4.5 mmol) dropwise. The reaction was heated at 70° C. for 8 hours. The cooled reaction mixture was diluted with water (50 ml) and extracted with ethyl acetate. The combined organic layers were washed with brine and evaporated in vacuo. The residue was purified by flash column chromatography on silica gel, eluting with 10–20% ethyl acetate/i-hexane, to give the Boc-derivatives of the title compounds as a 1:1 mixture (300 mg, 75%).

m/z (ES$^+$) 218 ([M−$^t$Bu]H$^+$).

This mixture (300 mg, 1.1 mmol) and 2M methanolic hydrochloric acid (50 ml) were stirred for 18 hours at room temperature. The solvent was removed in vacuo. The residue was basified with 2M aqueous sodium hydroxide and extracted with ethyl acetate. The combined organic layers were washed with brine and evaporated in vacuo to give the crude title amines as a brown oil (200 mg) that were used without further purification.

Description 70

6-exo-(2-Furyl)-2-azabicyclo[2.2.1]heptane and 5-exo-(2-furyl)-2-azabicyclo[2.2.1]heptane A solution of 2-tert-butoxycarbonyl-2-azabicyclo[2.2.1]hept-5-ene (Tet. 1998, 54(28) 8047–8054), (1.52 g, 7.8 mmol), 2-bromofuran (2.29 g, 16 mmol) and piperidine (2.7 ml, 27 mmol) in N,N-dimethylformamide (15 ml) was degassed. Tetrakis(triphenylphosphine)palladium(0) (450 mg, 0.39 mmol) was added followed by formic acid (0.9 ml, 23 mmol) dropwise. The reaction was degassed again and heated at 75° C. for 1 h then at 80° C. for 3 hours. The mixture was diluted with ethyl acetate (50 ml) and aqueous sodium hydrogen carbonate solution (150 ml). The aqueous layer was extracted with ethyl acetate and the combined organic layers washed with water (×3), dried (MgSO$_4$) and concentrated in vacuo. The residue was purified by flash column chromatography on silica, eluting with 15% ethyl acetate/i-hexane to afford the N-tert-butoxycarbonyl compounds as a mixture of 5- and 6-furyl isomers (1.52 g, 74%). 1.0 g (3.8 mmol) of this was dissolved in dichloromethane (5 ml) and trifluoroacetic acid (1.47 ml, 19 mmol) was added. The reaction was stirred at room temperature for 18 hours. The mixture was diluted with dichloromethane and basified with saturated aqueous sodium carbonate solution. The aqueous layer was extracted with dichloromethane and the combined organic layers dried (MgSO$_4$) and concentrated in vacuo. The residue was purified by flash column chromatography on silica gel, eluting with 5–25% 2M ammonia in methanol/dichloromethane, to give 6-(2-furyl)-2-azabicyclo[2.2.1]heptane (260 mg, 42%) and 5-(2-furyl)-2-azabicyclo[2.2.1]heptane (400 mg, 64%).

6-(2-Furyl)-2-azabicyclo[2.2.1]heptane:

$\delta_H$ (360 MHz, CDCl$_3$): 7.29 (1H, s), 6.27 (1H, dd, J 2.1, 2.8 Hz), 5.97 (1H, d, J 2.8 Hz), 3.61 (1H, s), 3.08–3.05 (1H, m), 3.00–2.97 (1H, m), 2.74–2.72 (1H, m), 2.69 (1H, s), 2.52 (1H, s), 1.85–1.75 (2H, m), 1.68–1.65 (1H, s), 1.53–1.50 (1H, m).

5-(2-Furyl)-2-azabicyclo[2.2.1]heptane:

$\delta_H$ (360 MHz, CDCl$_3$):7.32 (1H, d, J 1.0 Hz), 6.29 (1H, dd, J 1.9, 3.0 Hz), 6.02 (1H, d, J 3.0 Hz), 3.98 (1H, s), 3.41 (1H, br s), 3.20–3.16 (1H, m), 3.12–3.04 (2H, m), 2.76 (1H, s), 2.35–2.28 (1H, m), 1.95–1.88 (2H, m), 1.77–1.74 (1H, m).

The invention claimed is:
1. A compound of formula (I):

$$\text{Ar—SO}_2\text{—CR}^2\text{R}^3\text{-L-N(R}^1)_2 \qquad \text{I}$$

wherein:
the R$^1$ groups complete a heterocyclic ring system which is an azabicyclo[2.2.1]heptane ring, wherein said system is unsubstituted or substituted with up to 3 substituents selected from halogen, CN, NO$_2$, CF$_3$, R$^4$, OR$^5$, SR$^5$, N(R$^6$)R$^5$, CO$_2$R$^5$, OCOR$^4$, COR$^5$, CON(R$^6$)R$^5$, N(R$^6$)COR$^4$, N(R$^6$)SO$_2$R$^4$, CON(R$^6$)OR$^6$, C(R$^5$)=NOR$^6$ and =X;

X represents N—OR$^6$, or CR$^7$R$^8$;

R$^4$ represents phenyl, naphthyl or heterocyclyl, any of which is unsubstituted or substituted with up to 3 substituents selected from halogen, CN, NO$_2$, CF$_3$, OH, OCF$_3$, C$_{1-6}$alkyl, C$_{1-6}$alkoxy, C$_{1-6}$alkoxycarbonyl, C$_{2-6}$acyl and C$_{2-6}$acyloxy; or R$^4$ represents a nonaromatic hydrocarbon group of up to 10 carbon atoms which is unsubstituted or substituted with up to 3 halogen atoms or with one substituent selected from CN, NO$_2$, CF$_3$, OCF$_3$, C$_{1-6}$alkoxy, C$_{1-6}$alkoxycarbonyl, C$_{2-6}$acyl, C$_{2-6}$acyloxy, N(R$^9$)$_2$ and phenyl, phenoxy, phenylthio, naphthyl or heterocyclyl, any of which is unsubstituted or substituted with up to 3 substituents selected from halogen, CN, NO$_2$, CF$_3$, OH, OCF$_3$, C$_{1-6}$alkyl, C$_{1-6}$alkoxy, C$_{1-6}$alkoxycarbonyl, C$_{2-6}$acyl and C$_{2-6}$acyloxy;

R$^5$ represents H or R$^4$;

R$^6$ represents H or C$_{1-6}$alkyl;

or R$^5$ and R$^6$ bonded to the same nitrogen atom may complete pyrrolidine, piperidine morpholine, piperazine or tetrahydropyridine ring;

R$^7$ and R$^8$ independently represent H or a hydrocarbon group of up to 10 carbon atoms, or together complete a hydrocarbon ring of up to 14 members;

R$^2$ and R$^3$ independently represent H, hydrocarbon of up to 6 carbon atoms, C$_{2-6}$acyl, C$_{1-6}$alkoxycarbonyl or hydroxyC$_{1-6}$alkyl, or together complete a hydrocarbon ring of up to 6 carbon atoms;

L is a linking group selected from:
(a) —CR$^{2a}$R$^{3a}$—(CH$_2$)$_n$—;
(b) —O—CH$_2$CH$_2$—;
(c) —CH$_2$CH(OH)CH$_2$—;
(d) —CH=CH—CH$_2$—; and
(e) —C≡C—CH$_2$—;

R$^{2a}$ and R$^{3a}$ have the same definition as R$^2$ and R$^3$;
n is 1, 2 or 3;
Ar represents phenyl, naphthyl or heteroaryl, any of which is unsubstituted or substituted with up to 3 substituents selected from halogen, CN, NO$_2$, CF$_3$, OCF$_3$, R$^9$, OR$^9$, CO$_2$R$^9$ and COR$^9$; and
R$^9$ represents H or a hydrocarbon group of up to 7 carbon atoms;
or a pharmaceutically acceptable salt or N-oxide thereof.

2. The compound of claim 1 wherein R$^1$ is an azabicyclo[2.2.1]heptane ring which is unsubstituted or substituted with up to 3 substituents selected from: halogen, CN, NO$_2$, CF$_3$, R$^4$, OR$^5$, SR$^5$, N(R$^6$)R$^5$, CO$_2$R$^5$, OCOR$^5$, COR$^5$, CON(R$^6$)R$^5$, N(R$^6$)COR$^5$, N(R$^6$)SO$_2$R$^5$, CON(R$^6$)OR$^6$, C(R$^5$)=NOR$^6$ and =X.

3. The compound of claim 2 wherein R$^1$ is an azabicyclo[2.2.1]heptane ring which is unsubstituted or substituted with up to 3 substituents selected from: CN, CF$_3$, R$^4$, OR$^5$, SR$^5$, N(R$^6$)R$^5$, CO$_2$R$^4$, COR$^4$, CON(R$^6$)R$^5$, N(R$^6$)COR$^5$, N(R$^6$)SO$_2$R$^5$, CON(R$^6$)OR$^6$, C(R$^5$)=NOR$^6$ and =X.

4. The compound of claim 1 wherein R$^4$ is selected from: phenyl, naphthyl, pyridine, quinoline, furan, thiophene, oxazole, imidazole, benzimidazole, benzisoxazole, indole, tetrazole and quinazoline, which is unsubstituted or substituted with up to 3 substituents selected from: halogen, CN, NO$_2$, CF$_3$, OH, OCF$_3$, C$_{1-6}$alkyl, C$_{1-6}$alkoxy, C$_{1-6}$alkoxycarbonyl, C$_{2-6}$acyl and C$_{2-6}$acyloxy.

5. The compound of claim 1 wherein R$^4$ is selected from: 2-naphthyl; phenyl which is unsubstituted or substituted with up to 2 fluorine atoms or chlorine atoms, or with OH, Me, OMe, t-butoxy, CN, NO$_2$ or CF$_3$; 2-, 3- or 4-pyridyl which is unsubstituted or substituted with up to 2 fluorine atoms or chlorine atoms, or with Me, OMe, CN, or CF$_3$; 2-furyl; 3-furyl; 2-thienyl; 3-thienyl; 3-methylisoxazol-5-yl; 5-methylisoxazol-3-yl; 3,5-dimethylisoxazol-4-yl; oxazol-5-yl; 4-methyloxazol-2-yl; indol-3-yl; 2-methyltetrazol-5-yl; imidazol-2-yl; benzimidazol-2-yl; benzisothiazol-3-yl; 2-quinolinyl; and 2-quinoxalinyl.

6. The compound of claim 1 wherein R$^6$ represents H or C$_{1-6}$alkyl, or completes a ring with R$^5$ which is selected from pyrrolidine, piperidine, morpholine, piperazine and tetrahydropyridine.

7. The compound of claim 1 wherein L represents a linking group selected from —CR$^{2a}$R$^{3a}$—(CH$_2$)$_n$—; —O—CH$_2$CH$_2$—; —CH$_2$CH(OH)CH$_2$—; —CH=CH—CH$_2$—; and —C≡C—CH$_2$—; where R$^{2a}$ and R$^{3a}$ are independently selected from H and C$_{1-6}$alkyl.

8. The compound of claim 7 wherein L is selected from: —(CH$_2$)$_2$—; —(CH$_2$)$_3$—; —(CH$_2$)$_4$—; CH(Me)—(CH$_2$)$_2$—; —C(Me)$_2$—(CH$_2$)$_2$—; —O—CH$_2$CH$_2$—; —CH$_2$CH(OH)CH$_2$—; —CH=CH—CH$_2$—; and —C≡C—CH$_2$—.

9. A compound which is selected from the group consisting of:

2-(4-benzenesulfonyl-4-methyl-pentyl)-5-phenyl-2-azabicyclo[2.2.1]heptane;

2-(4-benzenesulfonyl-4-methyl-pentyl)-5-(4-fluoro-phenyl)-2-aza-bicyclo[2.2.1]heptane;

2-(4-benzenesulfonyl-4-methyl-pentyl)-5-phenyl-2-azabicyclo[2.2.1]heptane;

2-(4-benzenesulfonyl-4-methyl-pentyl)-6-furan-2-yl-2-aza-bicyclo[2.2.1]heptane;

2-[4-(4-chloro-benzenesulfonyl)-4-methyl-pentyl]-5-phenyl-2-aza-bicyclo[2.2.1]heptane; and 2-(4-benzenesulfonyl-4-methyl-pentyl)-5-furan-2-yl-2-aza-bicyclo[2.2.1]heptane;

or a pharmaceutically acceptable salt or N-oxide thereof.

10. A pharmaceutical composition comprising a therapeutically effective amount of the compound of claim 1 or a pharmaceutically acceptable salt or N-oxide thereof, and a pharmaceutically acceptable carrier.

11. A method for the treatment of a condition selected from: depression, anxiety, a sleep disorder and schizophrenia, in a subject suffering from such condition, which method comprises administration to the subject of a therapeutically effective amount of the compound of claim 1, or a pharmaceutically acceptable salt or N-oxide thereof.

* * * * *